United States Patent
Dequesne et al.

(10) Patent No.: US 8,715,687 B2
(45) Date of Patent: May 6, 2014

(54) **IMMUNOGENIC COMPOSITION COMPRISING VARIANTS OF *STAPHYLOCOCCAL* CLUMPING FACTOR A**

(75) Inventors: Guy Dequesne, Rixensart (BE); Sophie Marie Jeanne Valentine Germain, Rixensart (BE)

(73) Assignee: GlaxoSmithKline Biologicals S.A., Rixensart (BE)

(*) Notice: Subject to any disclaimer, the term of this patent is extended or adjusted under 35 U.S.C. 154(b) by 0 days.

(21) Appl. No.: 13/388,715

(22) PCT Filed: Aug. 3, 2010

(86) PCT No.: PCT/EP2010/061312
§ 371 (c)(1),
(2), (4) Date: Apr. 13, 2012

(87) PCT Pub. No.: WO2011/015590
PCT Pub. Date: Feb. 10, 2011

(65) Prior Publication Data
US 2012/0189650 A1 Jul. 26, 2012

(30) Foreign Application Priority Data
Aug. 5, 2009 (GB) .................................. 0913680.5

(51) Int. Cl.
*A61K 39/085* (2006.01)
*C07K 14/31* (2006.01)
*C12N 15/00* (2006.01)

(52) U.S. Cl.
USPC ..................... 424/190.1; 424/243.1; 530/350; 514/2.7

(58) Field of Classification Search
None
See application file for complete search history.

(56) References Cited

U.S. PATENT DOCUMENTS

2006/0115490 A1* 6/2006 Masignani et al. ........ 424/190.1

FOREIGN PATENT DOCUMENTS

WO WO 2005/060713 * 7/2005
WO WO 2009/095453 * 8/2009

OTHER PUBLICATIONS

Deivanayagam et al. The EMBO journal 21:6660-6672, 2002.*
Rodwell et al. In Harper's Biochemistry 23$^{rd}$ edition chapter 4, p. 23-28, 1993.*
Stenesh, J. Dictionary of Biochemistry and Molecular Biology. John Wiley & Sons. 1989, 2$^{nd}$ Ed. p. 97.*
McDevitt, et al., Identification of the ligand-binding domain of the surface-located fibrinogen receptor (clumping factor) of *Staphylococcus aureus*, Molecular Microbiol 16(5): 895-907 (1995).
Hartford, et al., Identification of Residues in the *Staphylococcus aureus* Fibrinogen-binding MSCRAMM Clumping Factor A (ClfA) That are Important for Ligand Binding, J Biol Chem 276(4): 2466-2473 (2001).
Deivanayagam, et al., A novel variant of the immunoglobulin fold in surface adhesins of *Staphylococcus aureus*: crystal structure of the fibrinogen-binding MSCRAMM, clumping factor A, EMBO J 21(24): 6660-6672 (2002).
Josefsson, et al., Fibrinogen Binding Sites P336 and Y338 of Clumping Factor A are Crucial for *Staphylococcus aureus* Virulence, PLoS One, 3(5): e2206 (2008).
Ganesh, et al., A Structural Model of the *Staphylococcus aureus* ClfA-Fibrinogen Interaction Opens New Avenues for the Design of Anti-Staphylococcal Therapeutics, PLoS Pathogens 4(11): e1000226 (2008).

* cited by examiner

*Primary Examiner* — Oluwatosin Ogunbiyi
(74) *Attorney, Agent, or Firm* — Alice P. Bradney

(57) ABSTRACT

The present invention relates to ClfA polypeptides wherein amino acid Y474 or an amino acid adjacent to Y474 is mutated such that fibrinogen binding activity is decreased compared to an equivalent ClfA polypeptide without mutation of Y474 or an amino acid adjacent to Y474 as well as immunogenic compositions, vaccines, processes and uses of such mutated ClfA polypeptides.

7 Claims, 4 Drawing Sheets

IMMUNOGENIC COMPOSITION COMPRISING VARIANTS OF *STAPHYLOCOCCAL* CLUMPING FACTOR A

This application is filed pursuant to 35 U.S.C. §371 as a United States National Phase Application of International Patent Application Serial No. PCT/EP2010/061312 filed Aug. 3, 2010, which claims priority to United Kingdom Application No. GB0913680.5 filed Aug. 5, 2009, the contents of which are hereby incorporated by reference.

TECHNICAL FIELD

The present invention relates to the field of variants of Staphylococcal fibrinogen binding proteins, particularly clumping factor A (ClfA), in which fibrinogen binding is decreased in comparison with a non-mutated version of the staphylococcal fibrinogen binding protein. Immunogenic compositions comprising such proteins and methods for manufacturing such immunogenic compositions as well as methods of prevention or treatment using such immunogenic compositions are also described.

BACKGROUND

*S. aureus* infections are treated with antibiotics, with penicillin being the drug of choice whereas vancomycin is used for methicillin resistant isolates. The percentage of staphylococcal strains exhibiting wide-spectrum resistance to antibiotics has become increasingly prevalent since the 1980's (Panlilo et al 1992, Infect. Control. Hosp. Epidemiol. 13; 582), posing a threat for effective antimicrobial therapy. In addition, the recent emergence of vancomycin resistant *S. aureus* strain has aroused fear that methicillin resistant *S. aureus* strains will emerge and spread for which no effective therapy is available.

An alternative approach of using antibodies against staphylococcal antigens in passive immunotherapy has been investigated. Therapy involving administration of polyclonal antisera are under development (WO 00/15238, WO 00/12132).

An alternative approach would be use of active vaccination to generate an immune response against staphylococci. Several candidates for inclusion as vaccine components have been identified. These include Fibronectin binding protein (U.S. Pat. No. 5,840,846), MHC II analogue (U.S. Pat. No. 5,648,240), fibrinogen binding proteins ClfA and ClfB (U.S. Pat. No. 6,008,341, WO 99/27109), GehD (US 2002/0169288), collagen binding protein (U.S. Pat. No. 6,288,214), SdrC, SdrD, SdrE, SdrF, SdrG and SdrH (WO 99/27109, WO 00/12689, WO 08/19162), mutant SEA and SEB exotoxins (WO 00/02523), 52 kDa vitronectin binding protein (WO 01/60852), IsdA, IsdB, IsdC and IsdH (WO 05/09379, WO 08/152,447).

Clumping factor A (ClfA) has been identified as a *S. aureus* fibrinogen binding protein (U.S. Pat. No. 6,008,341) and has been identified as a potential carrier protein for polysaccharides which cold be used to immunize against staphylococcal infection (WO 04/80490).

Recently, amino acids P336 and Y338 of ClfA have been recognised as fibrinogen binding sites, mutation of which led to the loss of fibrinogen binding (Josefsson et al 2008, PLOS One volume 3, Issue 5, page 1-7). The loss of fibrinogen binding in these variants led to an increased ability to protect against septic death in immunised mice, leading to the conclusion that the vaccine potential of recombinant ClfA is improved by removing its ability to bind fibrinogen.

There remains a need to develop a vaccine which protects against staphylococcal disease. An approach using *S. aureus* capsular polysaccharide conjugates has failed to achieve regulatory approval (WO 03/61558) and a more complex vaccine containing additional staphylococcal components may be required to give effective protection.

Accordingly, there is provided a ClfA polypeptide, fragment thereof or fusion protein thereof wherein amino acid Y474 or an amino acid adjacent to Y474 is mutated such that fibrinogen binding activity is decreased compared to an equivalent ClfA polypeptide or fragment thereof or fusion protein thereof without mutation of Y474 or an amino acid adjacent to Y474 (i.e. the relevant wild type ClfA).

In a second aspect of the invention, there is provided a polynucleotide encoding a ClfA polypeptide or fragment or fusion protein thereof, wherein amino acid Y474 or an amino acid adjacent to Y474 is mutated such that fibrinogen binding activity is decreased compared to an equivalent ClfA polypeptide or fragment thereof or fusion protein thereof without mutation of Y474 or an amino acid adjacent to Y474 (i.e. the relevant wild type ClfA).

In a third aspect of the invention, there is provided an immunogenic composition comprising a ClfA polypeptide wherein amino acid Y474 or an amino acid adjacent to Y474 is mutated such that fibrinogen binding activity is decreased compared to an equivalent ClfA polypeptide or fragment thereof or fusion protein thereof without mutation of Y474 or an amino acid adjacent to Y474 (i.e. the relevant wild type ClfA); and a pharmaceutically acceptable excipient.

In a fourth aspect of the invention there is provided a process for making the immunogenic composition of the invention comprising a step of adding a pharmaceutically acceptable excipient to the ClfA polypeptide, fragment or fusion protein wherein amino acid Y474 or an amino acid adjacent to Y474 is mutated such that fibrinogen binding activity is decreased compared to a an equivalent ClfA polypeptide or fragment thereof or fusion protein thereof without mutation of Y474 or an amino acid adjacent to Y474 (i.e. the relevant wild type ClfA).

In a fifth aspect of the invention there is provided a ClfA polypeptide or fragment of fusion protein, wherein amino acid Y474 or an amino acid adjacent to Y474 is mutated such that fibrinogen binding activity is decreased compared to a an equivalent ClfA polypeptide or fragment thereof or fusion protein thereof without mutation of Y474 or an amino acid adjacent to Y474 (i.e. the relevant wild type ClfA) for use in the treatment or prevention of staphylococcal infection or disease.

In a sixth aspect of the invention, there is provided a use of a ClfA polypeptide or fragment or fusion protein wherein amino acid Y474 or an amino acid adjacent to Y474 is mutated such that fibrinogen binding activity is decreased compared to an equivalent ClfA polypeptide or fragment thereof or fusion protein thereof without mutation of Y474 or an amino acid adjacent to Y474 (i.e. the relevant wild type ClfA) in the preparation of a medicament for the treatment or prevention of staphylococcal disease.

In a seventh aspect of the invention, there is provided a method of treating or preventing staphylococcal disease comprising administering a ClfA polypeptide or fragment or fusion protein polypeptide wherein amino acid Y474 or an amino acid adjacent to Y474 is mutated such that fibrinogen binding activity is decreased compared to an equivalent ClfA polypeptide or fragment thereof or fusion protein thereof without mutation of Y474 or an amino acid adjacent to Y474 (i.e. the relevant wild type ClfA) to a patient in need thereof.

DETAILED DESCRIPTION

Figure 1:
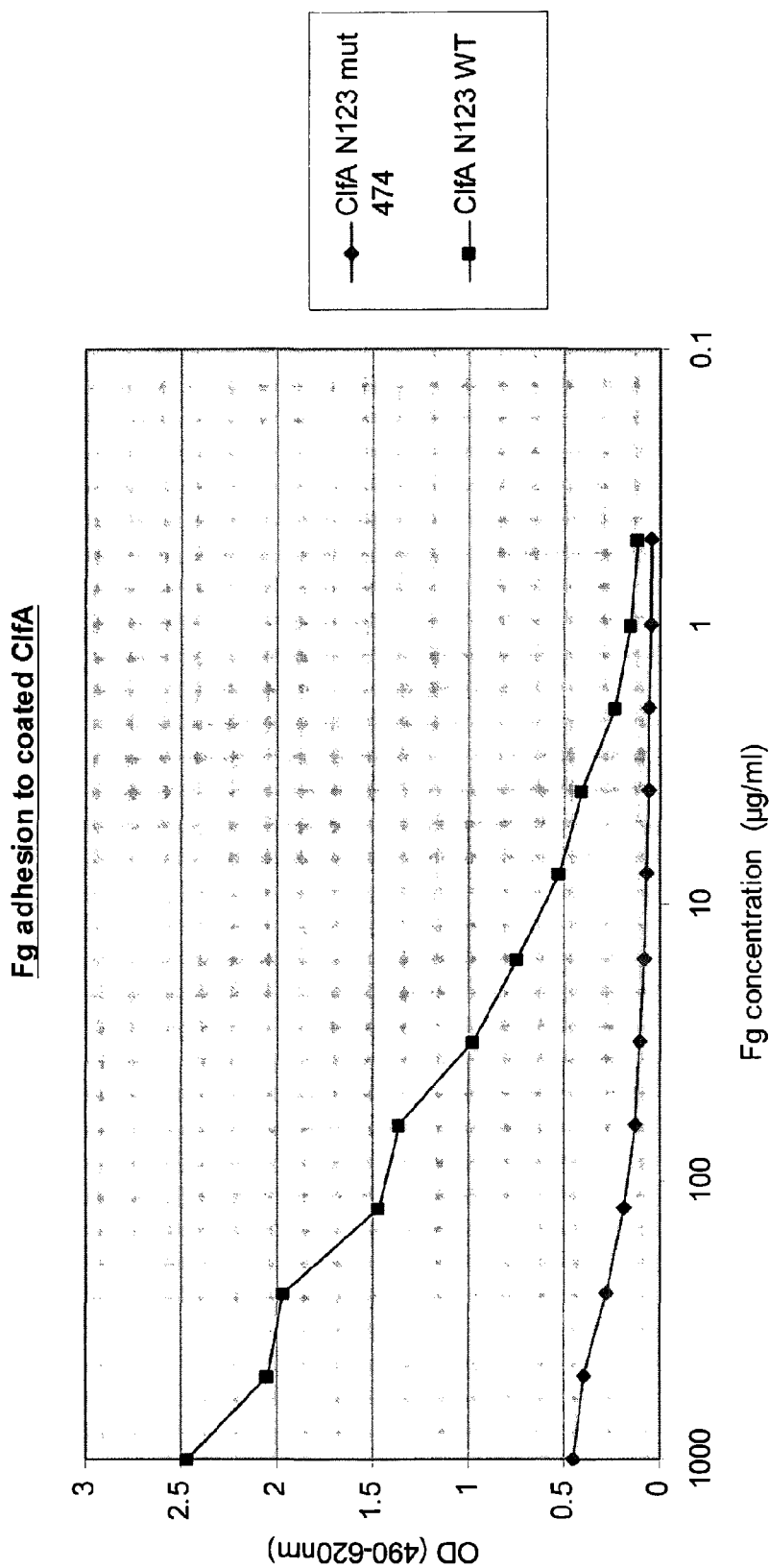
FIG. 1 Graph showing the results of an adhesion assay in which fibrinogen adhesion to ClfA coated plates is measured. The diamond marked line shows the binding of fibrinogen to ClfA N123 474 mutant and the square marked line shows the binding of fibrinogen to wildtype ClfA N123.

The present invention provides ClfA polypeptides, optionally recombinant, isolated or purified, wherein amino acid Y474 or an amino acid adjacent to Y474 is mutated such that fibrinogen binding activity is decreased compared to an equivalent ClfA polypeptide or fragment thereof without mutation of Y474 or an amino acid adjacent to Y474.

The amino acid Y474 is the 474$^{th}$ amino acid in SEQ ID NO: 3 which represents the full length sequence of ClfA from S. aureus strain NCTC8325. Similarly, amino acids numbering in the application as a whole is in relation to SEQ ID NO:3, thus amino acids 464 refers to the 464$^{th}$ amino acid in SEQ ID NO:3 and so on. In cases where ClfA from a different strain or a fragment or fusion protein of ClfA is used, Y474 refers to the tyrosine residue which aligns to Y474 of SEQ ID NO:3. Other amino acid references should be construed similarly, i.e. in relation to the amino acid to which it aligns in SEQ ID NO:3.

An amino acid adjacent to Y474 refers to an amino acid either next to Y474 on the N-terminal or C-terminal side or a distance of 2, 3, 4, 5, 6, 7, 8, 9 or 10 amino acids N-terminal or C-terminal to Y474.

By "mutated" is it meant that Y474 or an adjacent amino acid is either substituted with a different amino acid residue, or is deleted or that additional amino acids are inserted either N-terminal or C-terminal to Y474.

By "equivalent ClfA . . . " it is meant that the equivalent ClfA has the same amino acid sequence as the ClfA polypeptide, fragment or fusion protein of the invention, except for the mutation(s) at amino acid 474 or adjacent to 474.

Fibrinogen binding activity can be measured using an adhesion assay such as that described in Example 2. The ClfA polypeptides of the invention have a fibrinogen binding activity which is lower than the fibrinogen binding activity of a ClfA polypeptide having the same sequence over most of the polypeptide but having the wild-type sequence at amino acid Y474 and amino acids adjacent to Y474.

In an embodiment of the invention, the ClfA polypeptide of the invention is mutated at amino acid Y474 or an amino acid immediately adjacent to Y474. By "immediately adjacent to Y474" it is meant that the amino acids next to Y474 are referred to. Optionally, both of the immediately adjacent amino acid residues are mutated.

In an embodiment of the invention, the ClfA polypeptide contains a mutation at amino acid 474 by substitution of the tyrosine residue at amino acid 474 with a different amino acid. A different amino acid is any amino acid other than the one which was originally present at that position. Examples of different amino acids are; a polar but uncharged residue such as serine, threonine, asparagine or glutamate, a positively charged (basic) residue such as lysine, arginine or histidine, a negatively charged (acidic) residue such as glutamic acid or aspartic acid, special amino acid such as cysteine, glycine or proline or an alternative hydrophobic residue such as alanine, isoleucine, leucine, methionine, phenylalanine, tryptophan or valine.

In an embodiment of the invention the ClfA polypeptide contains a mutation of Y474 to a basic amino acid, for example histidine.

In an embodiment of the invention, the ClfA polypeptide is mutated by substitution of an amino acid adjacent to Y474. For example amino acid 464, 465, 466, 467, 468, 469, 470, 471, 472, 473, 475, 476, 477, 478, 479, 480, 481, 482, 483 and/or 484 is substituted with a different amino acid.

In an embodiment of the invention, both Y474 and at least one adjacent amino acid are both substituted with a different amino acid. For example amino acid Y474 is substituted with a different amino acid as well as at least one of 464, 465, 466, 467, 468, 469, 470, 471, 472, 473, 475, 476, 477, 478, 479, 480, 481, 482, 483 and/or 484. For example, at least 2, 3, 4, 5, 6, 7, 8, 9 or 10 amino acids including Y474 are deleted.

In an embodiment of the invention, at least amino acid Y474 is deleted from the ClfA polypeptide amino acid. For example Y474 is deleted or amino acids 464-474, 465-474, 466-474, 467-474, 468-474, 469-474, 470-474, 471-474, 472-474, 473-474, 474-475, 474-476, 474-477, 474-478, 474-479, 474-480, 474-481, 474-482, 474-483, 473-475, 472-476, 471-477, 470-478 or 469-479 are deleted.

In an embodiment of the invention, at least one amino acid is inserted adjacent or immediately adjacent to Y474 in the ClfA polypeptide. For example, at least 2, 3, 4, 5, 6, 7, 8, 9 or 10 amino acids are inserted adjacent to Y474, either N-terminal or C-terminal to Y474. In an embodiment of the invention, at least 2, 3, 4, 5, 6, 7, 8, 9 or 10 amino acids are inserted immediately adjacent to Y474, either N-terminal or C-terminal to Y474.

In an embodiment, the ClfA polypeptide or fragment or fusion protein thereof of the invention is capable of generating an immune response that is more protective than the immune response generated by a ClfA polypeptide or fragment or fusion protein thereof having the same amino acid sequence except for the mutation of Y474 or an amino acid adjacent to Y474.

In an embodiment of the invention the ClfA polypeptide or fragment thereof or fusion protein thereof contains multiple mutations which reduce fibrinogen binding activity. For example, a mutation at Y474 may be in combination with a mutation at P336 and/or Y338 of ClfA.

A further aspect of the invention provides fragments of the ClfA polypeptide of the polypeptides of the invention which comprise a fibrinogen binding domain. The N1, N2 and N3 domains of ClfA are involved in fibrinogen binding and are present at amino acids 40-220 for the N1 domain, amino acids 221-369 for the N2 domains and amino acids 370-559 for the N3 domain. The domains may alternatively be defined as slightly shorter fragments of the polypeptide sequence of SEQ ID NO:3, having, 1, 2, 3, 4, 5, 6, 7, 8, 9, 10, 20 or 25 amino acids fewer than the domain sizes set out above.

In an embodiment, the fragment of the invention comprises an N3 domain. For example, the fragment comprises amino acids 370-559, 370-550, 370-545, 365-559, 365-550 or 365-545 of a ClfA sequence such as SEQ ID NO:3.

In an embodiment, the fragment of the invention comprises a N2 domain. For example, the fragment comprises amino acids 221-369, 217-369, 229-369, 217-364, 221-364, 229-364, 217-545, 221-545, 229-545, 217-550, 221-550, 229-550, 217-559, 221-559 or 229-559 of a ClfA sequence such as SEQ ID NO:3.

In an embodiment, the fragment of the invention comprises a N1 domain. For example, the fragment comprises amino acids 41-216, 41-220, 41-228, 41-369, 41-364, 41-545, 41-550, 221-550 or 41-559 of a ClfA sequence such as SEQ ID NO:3.

The invention also encompasses polypeptides comprising a ClfA fragment of the invention as described above. Such polypeptides include the addition of sequences useful in the purification of the polypeptide, or the addition of additional sequence from a heterologous polypeptide, leading to the formation of a fusion protein. The heterologous protein may be a S. aureus protein (particularly those described below) or a protein from a different species.

The invention also provides an immunogenic fragment of the ClfA polypeptide of the invention, that is, a contiguous portion of the ClfA polypeptide which has the same or substantially the same immunogenic activity as the polypeptide comprising the polypeptide sequence of SEQ ID NO:3. That is to say, the fragment (if necessary when coupled to a carrier) is capable of raising an immune response which recognises ClfA polypeptide. Such an immunogenic fragment may include, for example, the ClfA polypeptide lacking an N-terminal leader sequence, and/or a transmembrane domain and/or a C-terminal anchor domain. In a preferred aspect the immunogenic fragment of ClfA according to the invention comprises substantially all of the extracellular domain of a polypeptide which has at least 85% identity, preferably at least 90% identity, more preferably at least 95% identity, most preferably at least 97-99% identity, to that of SEQ ID NO:3 over the entire length of said sequence.

A fragment is a polypeptide having an amino acid sequence that is entirely the same as part but not all of any amino acid sequence of any polypeptide of the invention. Fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of SEQ ID NO:3 or of variants thereof, such as a continuous series of residues that includes the amino-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:3.

A further embodiment of the invention provides fusion proteins of the ClfA polypeptides or fragments of the invention. Such fusion proteins may be made recombinantly and may comprise one portion of at least 2, 3, 4, 5 or 6 staphylococcal proteins, for example the combinations of staphylococcal proteins listed below. Alternatively, a fusion protein may comprise multiple portions of at least 2, 3, 4 or 5 staphylococcal proteins. These may combine different Staphylococcal proteins or fragments thereof in the same protein. Alternatively, the invention also includes individual fusion proteins of the ClfA polypeptide or fragment thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197. The fusion protein may be present in an immunogenic composition as a free protein or it may be a carrier protein linked to a saccharide.

In an embodiment, the ClfA polypeptide or fragment or fusion protein of the invention, comprises an amino acid sequence at least 80%, 85%, 90%, 93%, 95%, 95%, 97%, 98%, 99% or 100% identical to the amino acid sequence of any one of SEQ ID NO: 8-44 over the length of the corresponding sequence selected from SEQ ID NO: 8-44.

Polynucleotides of the Invention

A further aspect of the invention provides a polynucleotide encoding the polypeptide or fragment or fusion protein of the invention.

Polynucleotides of the invention do not encompass a complete genomic DNA from a staphylococcal species, e.g. S. aureus.

As a further aspect of the invention there are provided isolated nucleic acid molecules encoding and/or expressing ClfA polypeptides and polynucleotides including, for example, unprocessed RNAs, ribozyme RNAs, mRNAs, cDNAs, B- and Z-DNAs. Further embodiments of the invention include biologically, diagnostically, prophylactically, clinically or therapeutically useful polynucleotides and polypeptides, and variants thereof, and compositions, preferably immunogenic compositions, comprising the same.

Another aspect of the invention relates to isolated polynucleotides, including at least one full length gene, that encode ClfA polypeptides of the invention and polynucleotides closely related thereto and variants thereof.

In another particularly preferred embodiment of the invention relates to ClfA polypeptides of the invention from S. aureus comprising or consisting of an amino acid sequence selected from SEQ ID NO:344 or a variant thereof.

In a further aspect, the present invention provides for an isolated polynucleotide comprising or consisting of:
(a) a polynucleotide sequence which has at least 85% identity, preferably at least 90% identity, more preferably at least 95% identity, even more preferably at least 97, 98 or 99% or exact identity to any sequence from SEQ ID NO:2 over the entire length of the polynucleotide sequence from SEQ ID NO:2; or
(b) a polynucleotide sequence encoding a polypeptide which has at least 85% identity, preferably at least 90% identity, more preferably at least 95% identity, even more preferably at least 97, 98 or 99% or 100% exact, to any amino acid sequence selected from SEQ ID NO:4-44, over the entire length of the amino acid sequence from SEQ ID NO:4-44.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., Nucleic Acids Research 12(1): 387 (1984)), BLASTP, BLASTN (Altschul, S. F. et al., J. Molec. Biol. 215: 403-410 (1990), and FASTA (Pearson and Lipman Proc. Natl. Acad. Sci. USA 85; 2444-2448 (1988). The BLAST family of programs is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

Parameters for polypeptide sequence comparison include the following:
Algorithm: Needleman and Wunsch, J. Mol. Biol. 48: 443-453 (1970)
Comparison matrix: BLOSSUM62 from Henikoff and Henikoff,
Proc. Natl. Acad. Sci. USA. 89:10915-10919 (1992)
Gap Penalty: 8
Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:
Algorithm: Needleman and Wunsch, J. Mol. Biol. 48: 443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

The invention provides a polynucleotide sequence identical over its entire length to a coding sequence (open reading frame) set out in example 4. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci., USA 86: 821-824 (1989), or an HA peptide tag (Wilson et al., Cell 37: 767 (1984), both of which may be useful in purifying polypeptide sequence fused to them. Polynucleotides of the invention also include, but are not limited to, polynucleotides comprising a structural gene and its naturally associated sequences that control gene expression.

The invention further relates to variants of the polynucleotides described herein that encode variants of a polypeptides having a deduced amino acid sequence of any of the sequences of example 4. Fragments of polynucleotides of the invention may be used, for example, to synthesize full-length polynucleotides of the invention.

Preferred fragments are those polynucleotides which encode a B-cell or T-helper epitope, and recombinant, chimeric genes comprising said polynucleotide fragments.

Further particularly preferred embodiments are polynucleotides encoding ClfA variants, that have the amino acid sequence of ClfA polypeptides of any sequence from example 4 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of ClfA polypeptides.

Further preferred embodiments of the invention are polynucleotides that are at least 85% identical over their entire length to polynucleotides encoding ClfA polypeptides having an amino acid sequence set out in any of the sequences of example 4, and polynucleotides that are complementary to such polynucleotides. Alternatively, most highly preferred are polynucleotides that comprise a region that is at least 90% identical over its entire length to polynucleotides encoding ClfA polypeptides and polynucleotides complementary thereto. In this regard, polynucleotides at least 95% identical over their entire length to the same are particularly preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as mature polypeptides encoded by a DNA sequences selected from example 4.

In accordance with certain preferred embodiments of this invention there are provided polynucleotides that hybridize, particularly under stringent conditions, to ClfA polynucleotide sequences, such as those polynucleotides in example 4.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in any of the sequences of example 4 under stringent hybridization conditions with a probe having the sequence of said polynucleotide sequence set forth in the corresponding sequences of example 4 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding ClfA and to isolate cDNA and genomic clones of other genes that have a high identity, particularly high sequence identity, to the ClfA genes. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther*. (1983) 4: 419), delivery of DNA complexed with specific protein carriers (Wu et al., *J Biol. Chem*. (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transfection, microinjection, cationic lipid-mediated transfection, electroporation, conjugation, transduction, scrape loading, ballistic introduction and infection.

Representative examples of appropriate hosts include bacterial cells, such as cells of streptococci, staphylococci, enterococci, *E. coli, streptomyces*, cyanobacteria, *Bacillus subtilis, Neisseria meningitidis, Haemophilus influenzae* and *Moraxella catarrhalis*; fungal cells, such as cells of a yeast, *Kluveromyces, Saccharomyces, Pichia*, a basidiomycete, *Candida albicans* and *Aspergillus*; insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), *Listeria, Salmonella, Shigella*, BCG, streptococci. These viruses and bacteria can be virulent, or attenuated in various ways in order to obtain live vaccines. Such live vaccines also form part of the invention.

Combinations of Clfa and Further Antigens in Immunogenic Compositions

A further aspect of the invention discloses particular combinations of staphylococcal antigens which when combined, lead to an effective immunogenic composition against staphylococcal infection. The efficacy of the immunogenic composition is determined as by its ability to elicit a protective response against *S. aureus* primarily, but it is preferred that they also elicit a protective effect against the related bacteria such as *S. epidermidis*.

Preferred combinations of staphylococcal antigens, when combined in an immunogenic composition or vaccine, allow different staphylococcal functions to be targeted by the immune response. Such an immune response is better able to treat or prevent staphylococcal infection. For instance, known virulence factors include adhesins like ClfA, ClfB, SdrC, SdrD, SdrE, SdrG, SdrH, SasA, SasB, SasC, SasD, SasE, SasF, SasG and FnbpA and FnbpB which are involved in attachment of staphylococci to host cells; toxins such as EsxA, EsxB have a role in disabling the host immune system; IsdA, IsdB and IsdC and IsdH act as iron scavengers.

In particular, combinations of certain antigens from different classes, some of which are involved in adhesion to host cells, some of which are involved in iron acquisition, some of which are antotransporters and some of which are toxins, can elicit an immune response which protects against multiple functions of staphylococci required to sustain infection. Such combinations of antigens can surprisingly lead to improved vaccine efficacy against staphylococcal infection where more that one function of the bacterium is targeted by the immune response. Preferably, the improved vaccine efficacy is against *S. aureus* and/or *S. epidermidis*.

A further aspect of the invention provides an immunogenic composition comprising the ClfA polypeptide, fragment thereof or fusion protein thereof of the invention, further comprising a staphylococcal extracellular component binding protein or fragment thereof. In an embodiment, the extracellular component binding protein is selected from the group consisting of laminin receptor, SitC/MntC/saliva binding protein, EbhA, EbhB, Elastin binding protein (EbpS), EFB (FIB), SBI, autolysin, SdrC, SdrD, SdrE, SdrG, SdrH, Lipase GehD, SasA, SasB, SasC, SasD, SasE, SasF, SasG, FnbA, FnbB, Cna, ClfB, FbpA, Npase, IsaA/P isA, SsaA, EPB, SSP-1, SSP-2, Vitronectin binding protein, fibrinogen binding protein, coagulase, Fig and MAP.

Extracellular component binding proteins are proteins that bind to host extracellular components. The term includes, but is not limited to adhesins. Details of extracellular binding components including sequences are found in WO 07/113, 222, WO 08/19162, EP163623, WO 05/116064, U.S. Pat. No. 6,008,341, WO 99/27109, WO 97/48727, WO 02/59148, WO 05/115113, \WO 06/121664, WO 07/01361.

In an embodiment, the immunogenic composition of the invention further comprises a staphylococcal transporter protein or fragment thereof selected from the group consisting of IsdA, IsdB, IsdC and HarA. IsdA, IsdB, IsdC and HarA or IsdH are described in WO 07/113,222, WO 08/19162, WO 08/152,447 and WO 06/59247.

In an embodiment the immunogenic composition of the invention further comprises a staphylococcal regulator of virulence, toxin or fragment thereof selected from the group consisting of RNA III activating protein (RAP), EsxA, EsxB or a combination of EsxA and EsxB, EsaC and EsaB. These regulators of virulence and toxins are described in WO 07/113,222, WO 08/19162, WO 07/145,689, WO 05/09396, WO 10/14304 and WO 02/59148.

In an embodiment, the immunogenic composition of the invention comprises a further staphylococcal protein which is optionally a *S. aureus* or *S. epidermidis* protein. In an embodiment, the immunogenic composition of the invention further comprises one or more of the proteins described in WO 06/32475 or WO 07/113,222 optionally with the sequences described therein (incorporated by reference) or immunogenic fragments thereof. Many of the proteins fall into the categories of extracellular component binding proteins, transporter proteins or toxins and regulators of virulence. The immunogenic composition of the invention optionally further comprises a staphylococcal extracellular component binding protein or a staphylococcal transporter protein or a staphylococcal toxin or regulator of virulence. The immunogenic composition of the invention optionally comprises at least or exactly 1, 2, 3, 4, 5 or 6 staphylococcal proteins.

Preferred immunogenic compositions of the invention comprise a plurality of proteins selected from at least two different categories of protein, having different functions within Staphylococci. Examples of such categories of proteins are extracellular binding proteins, transporter proteins such as Fe acquisition proteins, toxins or regulators of virulence and other immunodominant proteins.

In a preferred embodiment, immunogenic composition of the invention further comprises a number of proteins equal to or greater than 2, 3, 4, 5 or 6 selected from 2, 3 or 4 different groups selected from;
  Group a) extracellular component binding proteins;
  Group b) transporter proteins;
  Group c) toxins or regulators of virulence
  Group d) structural proteins.

In a preferred embodiment, immunogenic composition of the invention further comprises a number of proteins equal to or greater than 2, 3, 4, 5 or 6 selected from 2, 3 or 4 of the following groups:
  group a)—at least one staphylococcal extracellular component binding protein or fragment thereof selected from the group consisting of laminin receptor, SitC/

MntC/saliva binding protein, EbhA, EbhB, Elastin binding protein (EbpS), EFB (FIB), SBI, ClfA, SdrC, SdrD, SdrE, SdrG, SdrH, SasF, lipase GehD, SasA, SasB, SasC, SasD, SasK, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP;

group b)—at least one staphylococcal transporter protein or fragment thereof selected from the group consisting of Immunodominant ABC transporter, IsdA, IsdB, IsdC, Mg2+ transporter, HarA, SitC and Ni ABC transporter;

group c)—at least one staphylococcal regulator of virulence, toxin or fragment thereof selected from the group consisting of EsxA, EsxB, RNA III activating protein (RAP);

group d)—at least one staphylococcal structural protein or immunogenic fragment thereof selected from the group consisting of MRPII and autolysin.

Optional combinations to be present in the immunogenic compositon of the invention include IsdA, IsdB and EsaC; SdrC, IsdA and EsaC; IsdA and EsxA; IsdB and EsxA; IsdA, IsdB and EsxA; SdrC, IsdA and EsxA; ClfA, IsdA and EsxB; IsdB and EsxB; IsdA, IsdB and EsxB; SdrC, IsdA and EsxB; SdrD, IsdA and IsdB; SdrC, IsdA and IsdB; SdrE, IsdA and IsdB; SdrG, IsdA and IsdB; IsdA and IsdB; ClfB, IsdA and IsdB, EsaC and IsdA; EsaC and IsdB; EsaC and EsxA; EsaC and EsxB; EsaC and SdrC.

Saccharides

In an embodiment, the immunogenic composition of the invention comprises a staphylococcal saccharide antigen as well as a mutated ClfA polypeptide. For example, the immunogenic composition comprises S. aureus type 5 and/or 8 capsular saccharide, optionally conjugated to a carrier protein.

In an embodiment, the immunogenic composition of the invention comprises PNAG optionally conjugated to a carrier protein. Optionally, the PNAG is less than 50%, 40%, 30%, 20% or 10% N-acetylated.

In an embodiment, the immunogenic composition comprises a 336 antigen or type I, II or III capsular ssaccharides from S. epidermidis.

Poly N-Acetylated Glucosamine (PNAG)

PNAG is a polysaccharide intercellular adhesin and is composed of a polymer of β-(1→6)-linked glucosamine, optionally substituted with N-acetyl and/or O-succinyl constituents. This polysaccharide is present in both S. aureus and S. epidermidis and can be isolated from either source (Joyce et al 2003, Carbohydrate Research 338; 903; Maira-Litran et al 2002, Infect. Imun. 70; 4433). For example, PNAG may be isolated from S. aureus strain MN8m (WO 04/43407). The preparation of dPNAG is described in WO 04/43405.

The polysaccharide previously known as poly-N-succinyl-β-(1-6)-glucosamine (PNSG) was recently shown not to have the expected structure since the identification of N-succinylation was incorrect (Maira-Litran et al 2002, Infect. Imun. 70; 4433). Therefore the polysaccharide formally known as PNSG and now found to be PNAG is also encompassed by the term PNAG.

PNAG may be of different sizes varying from over 400 kDa to between 75 and 400 kDa to between 10 and 75 kDa to oligosaccharides composed of up to 30 repeat units (of β-(1→6)-linked glucosamine, optionally substituted with N-acetyl and O-succinyl constituents). Any size of PNAG polysaccharide or oligosaccharide may be use in an immunogenic composition of the invention, for example a size of over 40 kDa can be used. Sizing may be achieved by any method known in the art, for instance by microfluidisation, ultrasonic irradiation or by chemical cleavage (WO 03/53462, EP497524, EP497525).

Size ranges of PNAG are for example 40-400 kDa, 50-350 kDa, 40-300 kDa, 60-300 kDa, 50-250 kDa and 60-200 kDa.

PNAG can have different degree of acetylation due to substitution on the amino groups by acetate. PNAG produced in vitro is almost fully substituted on amino groups (95-100%). Alternatively, a deacetylated PNAG can be used having less than 50%, 40%, 30%, 20%, 10% or 5% N-acetylation. Use of a deacetylated PNAG allows opsonic killing of Gram positive bacteria, optionally S. aureus and/or S. epidermidis (WO 04/43405). In an embodiment, the PNAG has a size between 40 kDa and 300 kDa and is deacetylated so that less than 50%, 40%, 30%, 20%, 10% or 5% of amino groups are N acetylated.

In an embodiment, the PNAG is not O-succinylated or is O-succinylated on less than 25, 20, 15, 10, 5, 2, 1 or 0.1% of residues.

The term deacetylated PNAG (dPNAG) refers to a PNAG polysaccharide or oligosaccharide in which less than 50%, 40%, 30%, 20%, 10% or 5% of the amino groups are acetylated.

As used herein, the term PNAG encompasses both acetylated and deacetylated forms of the saccharide.

In an embodiment, PNAG is deacetylated to form dPNAG, by chemically treating the native polysaccharide. For example, the native PNAG is treated with a basic solution such that the pH rises to above 10. For instance the PNAG is treated with 0.1-5M, 0.2-4M, 0.3-3M, 0.5-2M, 0.75-1.5M or 1M NaOH, KOH or $NH_4OH$. Treatment is for at least 10 or 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

In an embodiment, the polysaccharide(s) included in the immunogenic composition of the invention are conjugated to a carrier protein as described below or alternatively unconjugated.

Type 5 and Type 8 polysaccharides from S. aureus

Most strains of S. aureus that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al Carbohydrate Res. 201; 285 (1990) and Fournier et al Infect. Immun. 45; 87 (1984). Both have FucNAcp in their repeat unit as well as ManNAcA which can be used to introduce a sulfhydryl group.

Recently (Jones Carbohydrate Research 340, 1097-1106 (2005)) NMR spectroscopy revised the structures of the capsular polysaccharides to:

Type 5
→4)-β-D-ManNAcA-(1→4)-α-L-FucNAc(3OAc)-(1→3)-β-D-FucNAc-(1→

Type 8
→3)-β-D-ManNAcA(4OAc)-(1→3)-α-L-FucNAc(1→3)-α-D-FucNAc(1→

Polysaccharides may be extracted from the appropriate strain of S. aureus using methods well known to the skilled man, for instance as described in U.S. Pat. No. 6,294,177 or Infection and Immunity (1990) 58(7); 2367. For example, ATCC 12902 is a Type 5 S. aureus strain and ATCC 12605 is a Type 8 S. aureus strain.

Polysaccharides are of native size or alternatively may be sized, for instance by microfluidisation, ultrasonic irradiation or by chemical treatment. The invention also covers oligosaccharides derived from the type 5 and 8 polysaccharides from S. aureus.

The weight-average molecular weight of the saccharide may be 1000-2000000, 5000-1000000, 10000-500000, 50000-400000, 75000-300000, or 100000-200000. The molecular weight or average molecular weight of a saccharide herein refers to the weight-average molecular weight (Mw) of the saccharide measured prior to conjugation and is measured by MALLS. The MALLS technique is well known in the art and is typically carried out as described in example 2. For MALLS analysis of saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm). In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

The type 5 and/or 8 capsular polysaccharide or oligosaccharides included in the immunogenic composition of the invention are O-acetylated. In an embodiment, the degree of O-acetylation of type 5 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 8 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 5 and type 8 capsular polysaccharides or oligosaccharides is 10-100%, 20-100%, 30-100%, 40-100%, 50-100%. 60-100%, 70-100%, 80-100%, 90-100%, 50-90%, 60-90%, 70-90% or 80-90%.

The degree of O-acetylation of the polysaccharide or oligosaccharide can be determined by any method known in the art, for example, by proton NMR (Lernercinier and Jones 1996, Carbohydrate Research 296; 83-96, Jones and Lernercinier 2002, J Pharmaceutical and Biomedical analysis 30; 1233-1247, WO 05/033148 or WO 00/56357). A further commonalty used method is that described by Hestrin (1949) J. Biol. Chem. 180; 249-261.

O-acetyl groups can be removed by hydrolysis, for example by treatment with a base such as anhydrous hydrazine (Konadu et al 1994; Infect. Immun. 62; 5048-5054) or treatment with 0.1N NaOH for 1-8 hours. In order to maintain high levels of O-acetylation on type 5 and/or 8 polysaccharide or oligosaccharide, treatments which would lead to hydrolysis of the O-acetyl groups are minimised. For example treatment at extremes of pH are minimised.

The type 5 and 8 polysaccharides included in the immunogenic composition of the invention are optionally conjugated to a carrier protein as described below or are alternatively unconjugated.

The immunogenic compositions of the invention alternatively contains either type 5 or type 8 polysaccharide.

S. aureus 336 Antigen

In an embodiment, the immunogenic composition of the invention comprises the S. aureus 336 antigen described in U.S. Pat. No. 6,294,177.

The 336 antigen comprises β-linked hexosamine, contains no O-acetyl groups and specifically binds to antibodies to S. aureus Type 336 deposited under ATCC 55804.

In an embodiment, the 336 antigen is a polysaccharide which is of native size or alternatively may be sized, for instance by microfluidisation, ultrasonic irradiation or by chemical treatment. The invention also covers oligosaccharides derived from the 336 antigen.

The 336 antigen, where included in the immunogenic composition of the invention is optionally conjugated to a carrier protein as described below or are alternatively unconjugated.
Type I, II and III polysaccharides from S. epidermidis Strains ATCC-31432, SE-360 and SE-10 of S. epidermidis are characteristic of three different capsular types, I, II and III respectively (Ichiman and Yoshida 1981, J. Appl. Bacteriol. 51; 229). Capsular polysaccharides extracted from each serotype of S. epidermidis constitute Type I, II and III polysaccharides. Polysaccharides may be extracted by several methods including the method described in U.S. Pat. No. 4,197,290 or as described in Ichiman et al 1991, J. Appl. Bacteriol. 71; 176.

In one embodiment of the invention, the immunogenic composition comprises type I and/or II and/or III polysaccharides or oligosaccharides from S. epidermidis.

Polysaccharides are of native size or alternatively may be sized, for instance by microfluidisation, ultrasonic irradiation or chemical cleavage. The invention also covers oligosaccharides extracted from S. epidermidis strains.

These polysaccharides are unconjugated or are optionally conjugated as described below.
Conjugation of Polysaccharides Amongst the problems associated with the use of polysaccharides in vaccination, is the fact that polysaccharides per se are poor immunogens. Strategies, which have been designed to overcome this lack of immunogenicity, include the linking of the polysaccharide to large protein carriers, which provide bystander T-cell help. In an embodiment, the polysaccharides utilised in the invention are linked to a protein carrier which provide bystander T-cell help. Examples of these carriers which may be used for coupling to polysaccharide or oligosaccharide immunogens include the Diphtheria and Tetanus toxoids (DT, DT Crm197 and TT), Keyhole Limpet Haemocyanin (KLH), Pseudomonas aeruginosa exoprotein A (rEPA) and the purified protein derivative of Tuberculin (PPD), protein D from Haemophilus influenzae, pneumolysin or fragments of any of the above. Fragments suitable for use include fragments encompassing T-helper epitopes. In particular protein D fragment will optionally contain the N-terminal ⅓ of the protein. Protein D is an IgD-binding protein from Haemophilus influenzae (EP 0 594 610 B1).

In an embodiment, a carrier protein used in the immunogenic compositions of the invention comprises or consists of the fragment of a staphylococcal lsd protein, the fragment of a staphylococcal extracellular component binding protein or a fusion protein of the invention as described above.

In an embodiment, EsxA, EsxB, EsaC or EsaB are present in the immunogenic composition of the invention as unconjugated or free proteins (WO 08/19162, WO 10/14304).

The polysaccharides may be linked to the carrier protein(s) by any known method (for example, by Likhite, U.S. Pat. No. 4,372,945 by Armor et al., U.S. Pat. No. 4,474,757, WO and Jennings et al., U.S. Pat. No. 4,356,170). Optionally, CDAP conjugation chemistry is carried out (see WO95/08348).

In CDAP, the cyanylating reagent 1-cyano-dimethylaminopyridinium tetrafluoroborate (CDAP) is optionally used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

The polysaccharide may be solubilized in water or a saline solution. CDAP may be dissolved in acetonitrile and added immediately to the polysaccharide solution. The CDAP reacts with the hydroxyl groups of the polysaccharide to form a cyanate ester. After the activation step, the carrier protein is added. Amino groups of lysine react with the activated polysaccharide to form an isourea covalent link. After the coupling reaction, a large excess of glycine is then added to quench residual activated functional groups. The product is then passed through a gel permeation column to remove unreacted carrier protein and residual reagents.

Compositions

The invention provides an immunogenic composition or vaccine comprising the ClfA polypeptide, fragment or fusion protein of the invention and a pharmaceutically acceptable excipient.

The immunogenic compositions and vaccines of the present invention may be adjuvanted, particularly when intended for use in an elderly population but also for use in infant populations. Suitable adjuvants include an aluminum salt such as aluminum hydroxide gel or aluminum phosphate or alum, but may also be other metal salts such as those of calcium, magnesium, iron or zinc, or may be an insoluble suspension of acylated tyrosine, or acylated sugars, cationically or anionically derivatized saccharides, or polyphosphazenes.

It is preferred that the adjuvant be selected to be a preferential inducer of a TH1 type of response. Such high levels of Th1-type cytokines tend to favour the induction of cell mediated immune responses to a given antigen, whilst high levels of Th2-type cytokines tend to favour the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. (Annual Review of Immunology, 7, p145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof (or detoxified lipid A in general—see for instance WO2005107798), particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO0226757 and WO03507822) are also preferential inducers of a TH1 response and are suitable for use in the present invention.

A further adjuvant which may be used with the compositions of the invention may be selected from the group: a saponin, lipid A or a derivative thereof, an immunostimulatory oligonucleotide, an alkyl glucosaminide phosphate, an oil in water emulsion or combinations thereof. A further preferred adjuvant is a metal salt in combination with another adjuvant. It is preferred that the adjuvant is a Toll like receptor agonist in particular an agonist of a Toll like receptor 2, 3, 4, 7, 8 or 9, or a saponin, in particular Qs21. It is further preferred that the adjuvant system comprises two or more adjuvants from the above list. In particular the combinations preferably contain a saponin (in particular Qs21) adjuvant and/or a Toll like receptor 9 agonist such as a CpG containing immunostimulatory oligonucleotide. Other preferred combinations comprise a saponin (in particular QS21) and a Toll like receptor 9 agonist such as monophosphoryl lipid A or its 3 deacylated derivative, 3 D MPL, or a saponin (in particular QS21) and a Toll like receptor 4 ligand such as an alkyl glucosaminide phosphate.

Particularly preferred adjuvants are combinations of 3D-MPL and QS21 (EP 0 671 948 B1), oil in water emulsions comprising 3D-MPL and QS21 (WO 95/17210, WO 98/56414), or 3D-MPL formulated with other carriers (EP 0 689 454 B1). Other preferred adjuvant systems comprise a combination of 3 D MPL, QS21 and a CpG oligonucleotide as described in U.S. Pat. No. 6,558,670, U.S. Pat. No. 6,544,518.

In an embodiment the adjuvant is a Toll like receptor (TLR) 4 ligand, preferably an agonist such as a lipid A derivative particularly monophosphoryl lipid A or more particularly 3 Deacylated monophosphoryl lipid A (3 D-MPL).

3 D-MPL is available from GlaxoSmithKline Biologicals North America and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3 D-MPL is used. Small particle 3 D-MPL has a particle size such that it may be sterile-filtered through a 0.22 μm filter. Such preparations are described in International Patent Application No. WO 94/21292. Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764, 840. Some AGPs are TLR4 agonists, and some are TLR4 antagonists. Both are thought to be useful as adjuvants.

Another preferred immunostimulant for use in the present invention is Quil A and its derivatives. Quil A is a saponin preparation isolated from the South American tree Quilaja Saponaria Molina and was first described as having adjuvant activity by Dalsgaard et al. in 1974 ("Saponin adjuvants", Archiv. für die gesamte Virusforschung, Vol. 44, Springer Verlag, Berlin, p243-254). Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of Quillaja saponaria Molina which induces CD8+cytotoxic T cells (CTLs), Th1 cells and a predominant IgG2a antibody response and is a preferred saponin in the context of the present invention.

Particular formulations of QS21 have been described which are particularly preferred, these formulations further comprise a sterol (WO96/33739). The saponins forming part of the present invention may be separate in the form of micelles, mixed micelles (preferentially, but not exclusively with bile salts) or may be in the form of ISCOM matrices (EP 0 109 942 B1), liposomes or related colloidal structures such as worm-like or ring-like multimeric complexes or lipidic/ layered structures and lamellae when formulated with cholesterol and lipid, or in the form of an oil in water emulsion (for example as in WO 95/17210). The saponins may preferably be associated with a metallic salt, such as aluminium hydroxide or aluminium phosphate (WO 98/15287).

Preferably, the saponin is presented in the form of a liposome, ISCOM or an oil in water emulsion.

An enhanced system involves the combination of a monophosphoryl lipid A (or detoxified lipid A) and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving tocopherol with or without QS21 and/ or 3D-MPL in an oil in water emulsion is described in WO 95/17210. In one embodiment the immunogenic composition additionally comprises a saponin, which may be QS21.

Immunostimulatory oligonucleotides or any other Toll-like receptor (TLR) 9 agonist may also be used. The preferred oligonucleotides for use in adjuvants or vaccines of the present invention are CpG containing oligonucleotides, preferably containing two or more dinucleotide CpG motifs separated by at least three, more preferably at least six or more nucleotides. A CpG motif is a Cytosine nucleotide followed by a Guanine nucleotide. The CpG oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO95/26204.

The adjuvant may be an oil in water emulsion or may comprise an oil in water emulsion in combination with other adjuvants. The oil phase of the emulsion system preferably comprises a metabolisable oil. The meaning of the term metabolisable oil is well known in the art. Metabolisable can be defined as "being capable of being transformed by metabolism" (Dorland's Illustrated Medical Dictionary, W.B. Sanders Company, 25$^{th}$ edition (1974)). The oil may be any vegetable oil, fish, oil, animal or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10$^{th}$ Edition, entry no. 8619).

Tocols (e.g. vitamin E) are also often used in oil emulsions adjuvants (EP 0 382 271 B1; U.S. Pat. No. 5,667,784; WO 95/17210). Tocols used in the oil emulsions (preferably oil in water emulsions) of the invention may be formulated as described in EP 0 382 271 B1, in that the tocols may be dispersions of tocol droplets, optionally comprising an emulsifier, of preferably less than 1 micron in diameter. Alternatively, the tocols may be used in combination with another oil, to form the oil phase of an oil emulsion. Examples of oil emulsions which may be used in combination with the tocol are described herein, such as the metabolisable oils described above.

Oil in water emulsion adjuvants per se have been suggested to be useful as adjuvant compositions (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424, 067; EP 0 480 981 B). All of which form preferred oil emulsion systems (in particular when incorporating tocols) to form adjuvants and compositions of the present invention.

Most preferably the oil emulsion (for instance oil in water emulsions) further comprises an emulsifier such as TWEEN 80 and/or a sterol such as cholesterol.

A preferred oil emulsion (preferably oil-in-water emulsion) comprises a metabolisible, non-toxic oil, such as squalane, squalene or a tocopherol such as alpha tocopherol (and preferably both squalene and alpha tocopherol) and optionally an emulsifier (or surfactant) such as Tween 80. A sterol (preferably cholesterol) may also be included.

The method of producing oil in water emulsions is well known to the man skilled in the art. Commonly, the method comprises mixing the tocol-containing oil phase with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter. In an oil in water emulsion, the oil and emulsifier should be in an aqueous carrier. The aqueous carrier may be, for example, phosphate buffered saline.

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges. The amounts of the components present in the oil emulsions of the present invention are conventionally in the range of from 0.5-20% or 2 to 10% oil (of the total dose volume), such as squalene; and when present, from 2 to 10% alpha tocopherol; and from 0.3 to 3% surfactant, such as polyoxyethylene sorbitan monooleate. Preferably the ratio of oil (preferably squalene): tocol (preferably α-tocopherol) is equal or less than 1 as this provides a more stable emulsion. An emulsifier, such as Tween80 or Span 85 may also be present at a level of about 1%. In some cases it may be advantageous that the vaccines of the present invention will further contain a stabiliser.

Examples of preferred emulsion systems are described in WO 95/17210, WO 99/11241 and WO 99/12565 which disclose emulsion adjuvants based on squalene, α-tocopherol, and TWEEN 80, optionally formulated with the immunostimulants QS21 and/or 3D-MPL. Thus in a particularly preferred embodiment of the present invention, the adjuvant of the invention may additionally comprise further immunostimulants, such as LPS or derivatives thereof, and/or saponins. Examples of further immunostimulants are described herein and in "Vaccine Design—The Subunit and Adjuvant Approach" 1995, Pharmaceutical Biotechnology, Volume 6, Eds. Powell, M. F., and Newman, M. J., Plenum Press, New York and London, ISBN 0-306-44867-X.

In a preferred aspect the adjuvant and immunogenic compositions according to the invention comprise a saponin (preferably QS21) and/or an LPS derivative (preferably 3D-MPL) in an oil emulsion described above, optionally with a sterol (preferably cholesterol). Additionally the oil emulsion (preferably oil in water emulsion) may contain span 85 and/or lecithin and/or tricaprylin. Adjuvants comprising an oil-in-water emulsion, a sterol and a saponin are described in WO 99/12565.

Typically for human administration the saponin (preferably QS21) and/or LPS derivative (preferably 3D-MPL) will be present in a human dose of immunogenic composition in the range of 1 μg-200 μg, such as 10-100 μg, preferably 10 μg-50 μg per dose. Typically the oil emulsion (preferably oil in water emulsion) will comprise from 2 to 10% metabolisible oil. Preferably it will comprise from 2 to 10% squalene, from 2 to 10% alpha tocopherol and from 0.3 to 3% (preferably 0.4-2%) emulsifier (preferably tween 80 [polyoxyethylene sorbitan monooleate]). Where both squalene and alpha tocopherol are present, preferably the ratio of squalene: alpha tocopherol is equal to or less than 1 as this provides a more stable emulsion. Span 85 (Sorbitan trioleate) may also be present at a level of 0.5 to 1% in the emulsions used in the invention. In some cases it may be advantageous that the immunogenic compositions and vaccines of the present invention will further contain a stabiliser, for example other emulsifiers/surfactants, including caprylic acid (merck index 10th Edition, entry no. 1739), of which Tricaprylin is particularly preferred.

Where squalene and a saponin (preferably QS21) are included, it is of benefit to also include a sterol (preferably cholesterol) to the formulation as this allows a reduction in the total level of oil in the emulsion. This leads to a reduced cost of manufacture, improvement of the overall comfort of the vaccination, and also qualitative and quantitative improvements of the resultant immune responses, such as improved IFN-γ production. Accordingly, the adjuvant system of the present invention typically comprises a ratio of metabolisable oil:saponin (w/w) in the range of 200:1 to 300:1, also the present invention can be used in a "low oil" form the preferred range of which is 1:1 to 200:1, preferably 20:1 to 100:1, and most preferably substantially 48:1, this vaccine retains the beneficial adjuvant properties of all of the components, with a much reduced reactogenicity profile. Accordingly, the particularly preferred embodiments have a ratio of squalene:QS21 (w/w) in the range of 1:1 to 250:1, also a preferred range is 20:1 to 200:1, preferably 20:1 to 100:1, and most preferably substantially 48:1. Preferably a sterol (most preferably cholesterol) is also included present at a ratio of saponin:sterol as described herein.

The emulsion systems of the present invention preferably have a small oil droplet size in the sub-micron range. Most preferably the oil droplet sizes will be in the range 120 to 750 nm, and most preferably from 120-600 nm in diameter.

A particularly potent adjuvant formulation (for ultimate combination with AlPO4 in the immunogenic compositions of the invention) involves a saponin (preferably QS21), an LPS derivative (preferably 3D-MPL) and an oil emulsion (preferably squalene and alpha tocopherol in an oil in water emulsion) as described in WO 95/17210 or in WO 99/12565 (in particular adjuvant formulation 11 in Example 2, Table 1).

Examples of a TLR 2 agonist include peptidoglycan or lipoprotein. Imidazoquinolines, such as Imiquimod and Resiquimod are known TLR7 agonists. Single stranded RNA is also a known TLR agonist (TLR8 in humans and TLR7 in mice), whereas double stranded RNA and poly IC (polyinosinic-polycytidylic acid—a commercial synthetic mimetic of viral RNA). are exemplary of TLR 3 agonists. 3D-MPL is an example of a TLR4 agonist whilst CPG is an example of a TLR9 agonist.

The immunogenic composition may comprise an antigen and an immunostimulant adsorbed onto a metal salt. Aluminium based vaccine formulations wherein the antigen and the immunostimulant 3-de-O-acylated monophosphoryl lipid A (3D-MPL), are adsorbed onto the same particle are described in EP 0 576 478 B1, EP 0 689 454 B1, and EP 0 633 784 B1. In these cases then antigen is first adsorbed onto the aluminium salt followed by the adsorption of the immunostimulant 3D-MPL onto the same aluminium salt particles. Such processes first involve the suspension of 3D-MPL by sonication in a water bath until the particles reach a size of between 80 and 500 nm. The antigen is typically adsorbed onto aluminium salt for one hour at room temperature under agitation. The 3D-MPL suspension is then added to the adsorbed antigen and the formulation is incubated at room temperature for 1 hour, and then kept at 4° C. until use.

In another process, the immunostimulant and the antigen are on separate metal particles, as described in EP 1126876. The improved process comprises the adsorption of immunostimulant, onto a metallic salt particle, followed by the adsorption of the antigen onto another metallic salt particle, followed by the mixing of the discrete metallic particles to form a vaccine. The adjuvant for use in the present invention may be an adjuvant composition comprising an immunostimulant, adsorbed onto a metallic salt particle, characterised in that the metallic salt particle is substantially free of other antigen. Furthermore, vaccines are provided by the present invention and are characterised in that the immunostimulant is adsorbed onto particles of metallic salt which are substantially free from other antigen, and in that the particles of metallic salt which are adsorbed to the antigen are substantially free of other immunostimulant.

Accordingly, the present invention provides an adjuvant formulation comprising immunostimulant which has been adsorbed onto a particle of a metallic salt, characterised in the composition is substantially free of other antigen. Moreover, this adjuvant formulation can be an intermediate which, if such an adjuvant is used, is required for the manufacture of a vaccine. Accordingly there is provided a process for the manufacture of a vaccine comprising admixing an adjuvant composition which is one or more immunostimulants adsorbed onto a metal particle with an antigen. Preferably, the antigen has been pre-adsorbed onto a metallic salt. Said metallic salt may be identical or similar to the metallic salt which is adsorbed onto the immunostimulant. Preferably the metal salt is an aluminium salt, for example Aluminium phosphate or Aluminium hydroxide.

The present invention further provides for a vaccine composition comprising immunostimulant adsorbed onto a first particle of a metallic salt, and antigen adsorbed onto a metallic salt, characterised in that first and second particles of metallic salt are separate particles.

LPS or LOS derivatives or mutations or lipid A derivatives described herein are designed to be less toxic (e.g. 3D-MPL) than native lipopolysaccharides and are interchangeable equivalents with respect to any uses of these moieties described herein.

In one embodiment the adjuvant used for the compositions of the invention comprises a liposome carrier (made by known techniques from a phospholipids (such as dioleoyl phosphatidyl choline [DOPC]) and optionally a sterol [such as cholesterol]). Such liposome carriers may carry lipid A derivatives [such as 3D-MPL—see above] and/or saponins (such as QS21—see above). In one embodiment the adjuvant comprises (per 0.5 mL dose) 0.1-10 mg, 0.2-7, 0.3-5, 0.4-2, or 0.5-1 mg (e.g. 0.4-0.6, 0.9-1.1, 0.5 or 1 mg) phospholipid (for instance DOPC), 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 5-60, 10-50, or 20-30 µg (e.g. 5-15, 40-50, 10, 20, 30, 40 or 50 µg) lipid A derivative (for instance 3D-MPL), and 5-60, 10-50, or 20-30 µg (e.g. 5-15, 40-50, 10, 20, 30, 40 or 50 µg) saponin (for instance QS21).

In one embodiment the adjuvant used for the compositions of the invention comprises an oil in water emulsion made from a metabolisable oil (such as squalene), an emulsifier (such as Tween 80) and optionally a tocol (such as alpha tocopherol). In one embodiment the adjuvant comprises (per 0.5 mL dose) 0.5-15, 1-13, 2-11, 4-8, or 5-6 mg (e.g. 2-3, 5-6, or 10-11 mg) metabolisable oil (such as squalene), 0.1-10, 0.3-8, 0.6-6, 0.9-5, 1-4, or 2-3 mg (e.g. 0.9-1.1, 2-3 or 4-5 mg) emulsifier (such as Tween 80) and optionally 0.5-20, 1-15, 2-12, 4-10, 5-7 mg (e.g. 11-13, 5-6, or 2-3 mg) tocol (such as alpha tocopherol).

This adjuvant may optionally further comprise 5-60, 10-50, or 20-30 µg (e.g. 5-15, 40-50, 10, 20, 30, 40 or 50 µg) lipid A derivative (for instance 3D-MPL).

This adjuvant may optionally contain 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 5-60, 10-50, or 20-30 µg (e.g. 5-15, 40-50, 10, 20, 30, 40 or 50 µg) lipid A derivative (for instance 3D-MPL), and 5-60, 10-50, or 20-30 µg (e.g. 5-15, 40-50, 10, 20, 30, 40 or 50 µg) saponin (for instance QS21).

In one embodiment the adjuvant used for the compositions of the invention comprises aluminium phosphate and a lipid A derivative (such as 3D-MPL). This adjuvant may comprise (per 0.5 mL dose) 100-750, 200-500, or 300-400 µg Al as aluminium phosphate, and 5-60, 10-50, or 20-30 µg (e.g. 5-15, 40-50, 10, 20, 30, 40 or 50 µg) lipid A derivative (for instance 3D-MPL).

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal polysaccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, for example, it may be present in combination with the bacterial protein component of the vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

The amount of conjugate antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 µg of polysaccharide, typically 0.1-50 µg, 0.1-10 µg, 1-10 µg or 1-5 µg for polysaccharide conjugates.

The content of protein antigens in the vaccine will typically be in the range 1-100 µg, 5-50 µg or 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Optionally the solution is lyophilized in the presence of a sugar such as sucrose, trehalose or lactose. It is typical that they are lyophilized and extemporaneously reconstituted prior to use. Lyophilizing may result in a more stable composition (vaccine).

A further aspect of the invention is a process for making the immunogenic composition or vaccine of the invention comprising the step of adding a pharmaceutically acceptable excipient to the ClfA polypeptide, fragment thereof or fusion protein thereof of the invention.

The invention also encompasses method of treatment or staphylococcal infection, particularly hospital acquired nosocomial infections.

This immunogenic composition or vaccine of the invention is particularly advantageous to use in cases of elective surgery. Such patients will know the date of surgery in advance and could be inoculated in advance. Since it is not know whether the patient will be exposed to S. aureus or S. epidermidis infection, it is preferred to inoculate with a vaccine of the invention that protects against both, as described above. Typically adults over 16 awaiting elective surgery are treated with the immunogenic compositions and vaccines of the invention. Alternatively children aged 3-16 awaiting elective surgery are treated with the immunogenic compositions and vaccines of the invention.

It is also possible to inoculate health care workers with the vaccine of the invention.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

The amount of antigen in each vaccine dose is selected as an amount which induces an immunoprotective response without significant, adverse side effects in typical vaccines. Such amount will vary depending upon which specific immunogen is employed and how it is presented. The protein content of the vaccine will typically be in the range 1-100 µg, 5-50 µg, typically in the range 10-25 µg. An optimal amount for a particular vaccine can be ascertained by standard studies involving observation of appropriate immune responses in subjects. Following an initial vaccination, subjects may receive one or several booster immunizations adequately spaced.

An embodiment of the invention is a method of preventing or treating staphylococcal infection or disease comprising the step of administering the ClfA polypeptide, or fragment or fusion protein or immunogenic composition or vaccine of the invention to a patient in need thereof.

A further embodiment of the invention is the ClfA polypeptide or fragment thereof or fusion protein thereof or immunogenic composition of the invention for use in the treatment or prevention of staphylococcal infection or disease, optionally post-surgery staphylococcal infection or disease.

A further embodiment of the invention is a use of the ClfA polypeptide or fragment thereof or fusion protein thereof or immunogenic composition of the invention in the manufacture of a vaccine for treatment or prevention of staphylococcal infection or disease, optionally post-surgery staphylococcal infection.

The term 'staphylococcal infection' encompasses infection caused by S. aureus and/or S. epidermidis and other staphylococcal strains capable of causing infection in a mammalian, optionally human host.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1

Expression and Purification of ClfA N123 Domains B2312

The clfA gene fragment from *Staphylococcus aureus* NCTC8325 strain coding for amino acids 40 to 559 was codon-optimized and synthesized in 2 portions by GeneArt (Regensburg, Germany). This gene fragment encodes for three structural domains identified as N1, N2 and N3 which contains the fibrinogen-binding activity of ClfA. To enable ligation, the restriction sites NdeI and SacII were added at the extremities of the first synthetic gene portion, while SacII and XhoI were added to the second. PCR reaction was used to add stop codons at its 3' end just before the XhoI site and the tyrosine residue at position 474 was replaced by a histidine residue in the second synthetic fragment. The 2 fragments were thus cloned into the pET24b (+) expression vector (Novagen) using the rapid DNA ligation kit (Roche, Mannheim, Germany) by which the DNA fragments and the plasmid were assembled simultaneously. Finally, the final construct was generated following transformation of *E. coli* strain BLR (DE3) with the expression vector containing the N123 domain (with mut474) standard procedures.

*E. coli* BLR (DE3) strain: F$^-$ ompT hsdS$_B$(r$_B^-$ m$_B^-$) gal dcm (DE3) □ (srl-recA) 306::Tn 10 (Tet$^R$). (Novagen)

BLR is a recA-derivative of BL21 that improves plasmid monomer yields and may help stabilize target plasmids containing repetitive sequences or whose products may cause the loss of the DE3 prophage.

This strain is tetracycline resistant (12.5 µg/ml).

DE3 indicates that the host is a lysogen of DE3, and therefore carries a chromosomal copy of the T7 RNA polymerase gene under control of the lacUV5 promoter. Such strains are suitable for production of protein from target genes cloned in pET vectors by induction with IPTG.

B2378:

The wild-type sequence of N123 domain (amino acids 40-559 without a mutation at 474) was restored by site-directed mutagenesis (Quickchange Site-directed Mutagenesis Kit; Stratagene) using the expression vector containing the N123 mutation (with mut474) as template. The final strain was generated by the transformation of *E. coli* strain BLR (DE3) with the expression vector containing the N123 domain (wild-type sequence) according standard procedures.

Purification

The *E. coli*, transformed with pET-ClfA constructs were cultured either in a fermentor (ClfA-N1N2N3 H474) or in a shake flask (ClfA-N1N2N3 wild type) and expression was induced using IPTG. *E. coli* cell paste was harvested and was resuspended in 50 mM phosphate buffer pH 7.2 containing 50 mM NaCl, 2 mM EDTA and 1 mM PMSF to reach an OD$_{650nm}$ of 120. The suspension was submitted to mechanical disruption and centrifuged at 12200 g for 30 min at 4° C., to produce a ClfA N1N2N3 containing supernatant. ClfA was purified from the supernatant using a Sephacryl HR300 column equilibrated and eluted with 10 mM Na borate pH 9.5. The fractions containing ClfA were selected on basis of purity by SDS-PAGE, pooled and sterile-filtered on 0.22 µm.

Example 2

Fibrinogen Binding Experiments

Fibrinogen Adhesion to Coated ClfA:

ClfA proteins were coated at 10 µg/ml in phosphate buffered saline (PBS) on high binding microtitre plates (Nunc Maxisorp) overnight at 4° C. The plates were blocked with PBS-BSA 1% for 30 min at room temperature with shaking.

After washing, human fibrinogen (ref: SIGMA F4883-16) was added at a 1 mg/ml starting concentration, then further twofold dilutions were made in microplates which were incubated for 1 hour at 37° C. with shaking.

After washing, the bound fibrinogen was detected using a peroxydase conjugated anti-fibrinogen goat polyclonal antibody (ref: ABCAM 7539-1) diluted 1:5000 in PBS-BSA 0.2%-Tween 0.05%. The detection antibodies were incubated for 60 minutes at room temperature with agitation.

The color was developed using 4 mg OPD (Sigma)+5 µl H2O2 per 10 ml pH 4.5 0.1M citrate buffer for 15 minutes in the dark at room temperature. The reaction was stopped with 50 µl HCl, and the optical density was read at 490 nm relative to 620 nm.

The results are shown in FIG. 1 which shows that the 474 mutant ClfA N123 protein bound poorly to fibrinogen compared to the wild type ClfA N123 protein.

ClfA Adhesion to Coated Fibrinogen:

Human fibrinogen (ref: SIGMA F4883-16) was coated at 10 µg/ml in phosphate buffered saline (PBS) on high binding microtitre plates (Nunc Maxisorp) overnight at 4° C. The plates were blocked with PBS-BSA 1% for 30 min at room temperature with shaking.

After washing, the ClfA was added at a 50 µg/ml starting concentration, then further twofold dilutions were made in microplates which were incubated for 1 hour at 37° C. with shaking.

After washing, the bound ClfA was detected using anti-ClfA rabbit polyclonal (obtained after immunization with his-tagged N123 ClfA) diluted 1:500 in PBS-BSA 0.2%-Tween 0.05% and incubated for 1 hour at 37° C. with shaking.

After washing, bound rabbit antibody was detected using Jackson ImmunoLaboratories Inc. peroxidase-conjugated affiniPure Goat Anti-Rabbit IgG (ref: 111-035-003) diluted 1:5000 in PBS-Tween 0.05%. The detection antibodies were incubated for 30 minutes at room temperature with shaking.

The color was developed using 4 mg OPD (Sigma)+5 µl H2O2 per 10 ml pH 4.5 0.1M citrate buffer for 15 minutes in the dark at room temperature. The reaction was stopped with 50 µl HCl, and the optical density was read at 490 nm relative to 620 nm.

Figure 2:
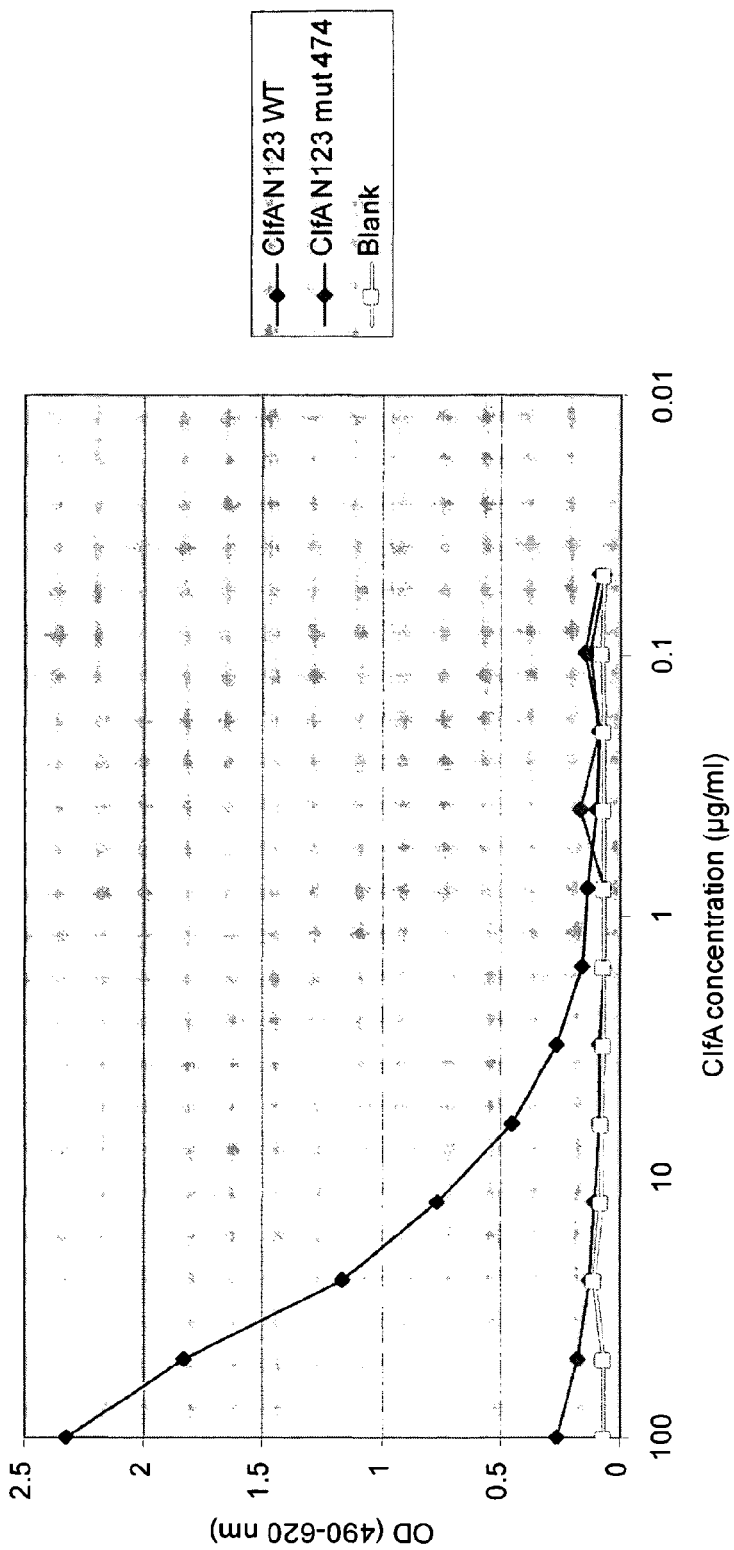
FIG. 2 Graph showing the results of an adhesion assay in which ClfA adhesion to fibrinogen coated plates is measured. The darker diamond marked line shows the binding of Wild-type N123 ClfA to fibrinogen, the lighter diamond marker line shows the binding of 474 mutant ClfA N123 to fibrinogen and the square marked line shows the negative control FIG. 3 Graph showing the ability of antibodies raised against wild type of 474 mutant ClfA N123 to inhibit the binding of fibrinogen to N123 ClfA coated plates.

The results shown in FIG. 2 demonstrate again that the 474 mutate ClfA N123 protein bound very poorly to fibrinogen compared to the wild type ClfA N123 protein.

Example 3

Inhibition Assay of Fibrinogen Adhesion to Coated ClfA

Groups of 20 mice were inoculated intramuscularly with 10 µg of N123 or mutated 474 ClfA formulated with the adjuvant AS02V, on days 0, 14 and 28. A control group was inoculated with the adjuvant alone.

On day 42 serum was collected from the mice and pooled sera from each group were tested in an inhibition assay of fibrinogen adhesion to coated ClfA.

Purified ClfA was coated at 10 µg/ml in phosphate buffered saline (PBS) on high binding microtitre plates (Nunc Maxisorp) overnight at 4° C. The plates were blocked with PBS-BSA 1% for 30 min at room temperature with agitation. After washing, the mice antisera were added at a 10-fold starting dilution, then further twofold dilutions were made in microplates which were incubated at room temperature for 1 hour with shaking. Without a washing step, human fibrinogen (Ref: SIGMA F4883-16) was added at a 400 µg/ml concentration in PBS-BSA 0.2%-Tween 0.05% and was incubated at 37° C. for 1 hour with shaking.

After washing, the bound fibrinogen was detected using a peroxydase conjugated anti-fibrinogen goat polyclonal antibody (ref: ABCAM 7539-1) diluted 1:5000 in PBS-BSA 0.2%-Tween 0.05%. The detection antibodies were incubated for 60 minutes at room temperature with agitation. The color was developed using 4 mg OPD (Sigma)+5 µl H2O2 per 10 ml pH 4.5 0.1M citrate buffer for 15 minutes in the dark at room temperature. The reaction was stopped with 50 µl HCl, and the optical density was read at 490 nm relative to 620 nm.

Figure 3:
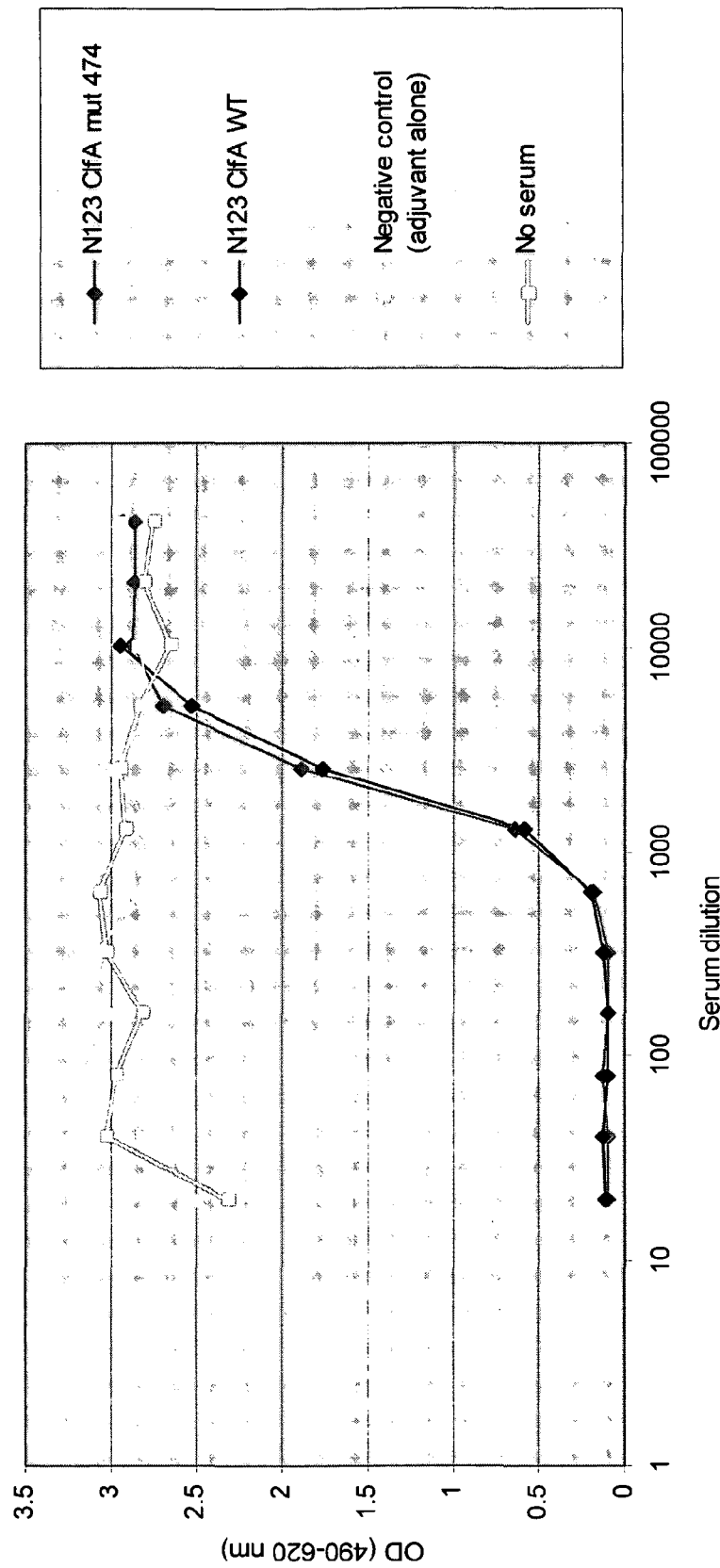

The results shown in FIG. 3 demonstrate that antibodies raised against both wild type and 474 mutant ClfA N123 were able to inhibit the binding of fibrinogen to ClfA N123 coated plates to about the same degree.

Inhibition Assay of S. aureus Adhesion to Coated Fibrinogen

Groups of 20 mice were inoculated intramuscularly with 10 µg of N123 or mutated 474 ClfA formulated with the adjuvant AS02V, on days 0, 14 and 28. A control group was inoculated with the adjuvant alone.

On day 42 serum was collected from the mice and pooled sera from each group were tested in an inhibition assay of S. aureus adhesion to coated fibrinogen.

Human fibrinogen (ref: SIGMA F4883-16) was coated at 10 µg/ml in phosphate buffered saline (PBS) on high binding microtitre plates (Nunc Maxisorp) overnight at 4° C. The plates were blocked with PBS-BSA 1% for 30 min at room temperature with shaking.

During this saturation step, serial two-fold dilutions (starting at 1/10) of the mice antisera were done in another microplate in PBS-BSA 0.2%-Tween 0.05%. Then, heat inactivated Newman D spa S. aureus bacteria (2 10e6 CFU/well) were added and the microplates were incubated at room temperature for 30 minutes with shaking.

After washing of the fibrinogen coated microplates, the mix antisera-bacteria was added and incubated at room temperature for 30 minutes with shaking.

After washing, the bound bacteria were detected using anti-killed whole cells rabbit polyclonal (obtained after immunization with killed S. aureus Lowenstein) diluted 1:50000 in PBS-BSA 0.2%-Tween 0.05% and incubated for 30 minutes at room temperature with shaking.

After washing, bound rabbit antibody was detected using Jackson ImmunoLaboratories Inc. peroxidase-conjugated affiniPure Goat Anti-Rabbit IgG (ref: 111-035-003) diluted 1:5000 in PBS-tween 0.05%. The detection antibodies were incubated for 30 minutes at room temperature with shaking.

The color was developed using 4 mg OPD (Sigma)+5 µl H2O2 per 10 ml pH 4.5 0.1M citrate buffer for 15 minutes in the dark at room temperature. The reaction was stopped with 50 µl HCl, and the optical density was read at 490 nm relative to 620 nm.

Figure 4:
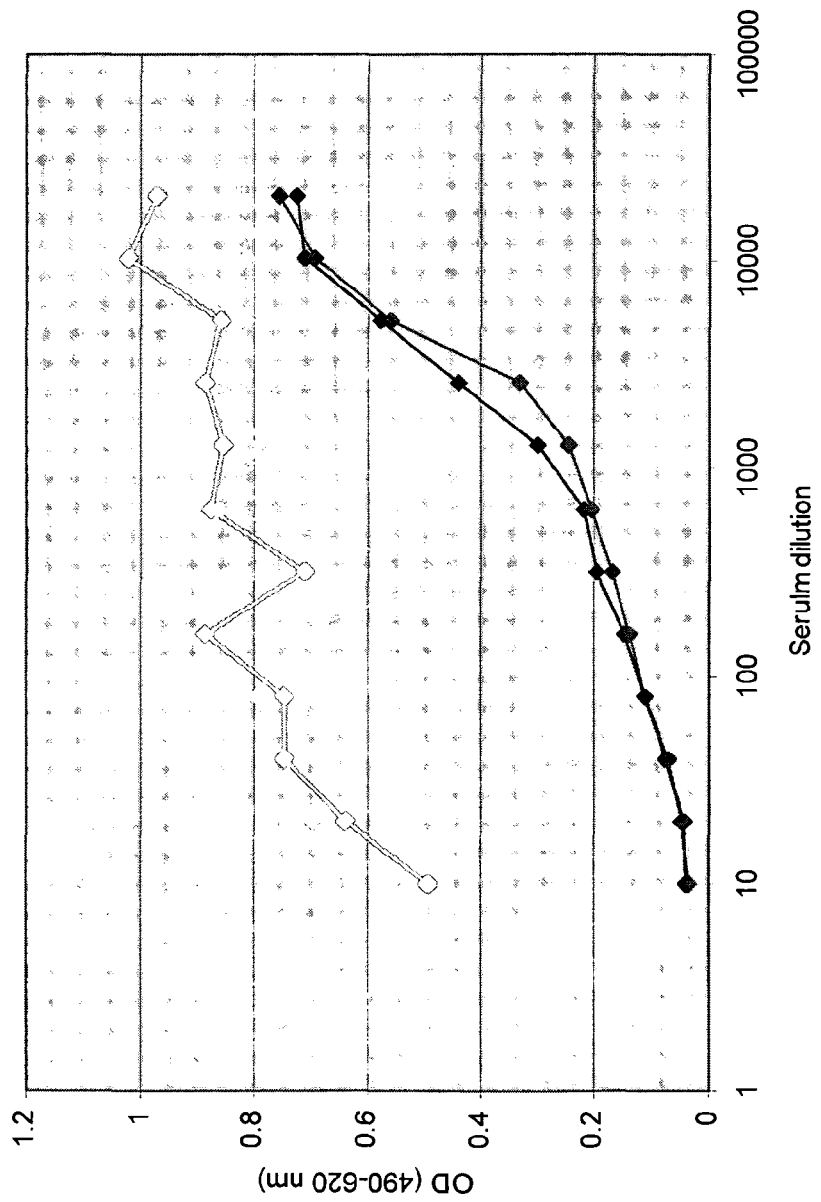
FIG. 4 Graph showing the ability of antibodies raised against wild type and 474 mutant ClfA to inhibit the binding of S. aureus bacteria to N123 ClfA coated plates.

The results shown in FIG. 4 demonstrate that antibodies raised against both wild type and 474 mutant ClfA N123 were able to inhibit the binding of S. aureus bacteria to fibrinogen coated plates to about the same degree.

Example 4

Nucleic Acid Encoding and Polypeptide Sequences of Some ClfA Polypeptides of the Invention

```
SEQ ID NO: 1 ClfA N1N2N3 Nucleic acid
ATG

AGCGAAAACAGCGTGACCCAGAGCGATAGCGCGAGCAACGAAAGCAAAAGCAACGATAGCAGCAGCGTTAGCGC

AGCGCCGAAAACCGATGATACCAACGTGAGCGATACCAAAACCAGCAGCAACACCAACAACGGCGAAACCAGCGTGGCGC
```

```
AGAATCCGGCGCAGCAGGAAACCACCCAAAGCTCTAGCACCAACGCGACCACCGAAGAAACCCCGGTGACCGGCGAAGCG

ACCACCACGACGACCAACCAGGCGAATACCCCGGCGACCACCCAGTCTAGCAATACCAATGCGGAAGAACTGGTGAACCA

GACCAGCAACGAAACCACCTCTAATGATACCAACACCGTGAGCAGCGTGAACAGCCCGCAGAACAGCACCAATGCCGAAA

ACGTGAGCACCACCCAGGATACCAGCACCGAAGCGACCCCGAGCAACAACGAAAGCGCACCGCAAAGCACCGATGCGAGC

AACAAAGATGTGGTGAACCAGGCGGTGAATACCAGCGCACCGCGTATGCGTGCGTTTAGCCTGGCCGCGGTTGCGGCGGA

TGCGCCGGTTGCGGGCACCGATATCACCAACCAGCTGACGAACGTGACCGTGGGCATTGATAGCGGCACCACCGTGTATC

CGCATCAGGCGGGCTATGTGAAACTGAACTATGGCTTTAGCGTGCCGAACAGCGCGGTGAAAGGCGATACCTTTAAAATT

ACCGTGCCGAAAGAACTGAACCTGAACGGCGTGACCAGCACCGCGAAAGTGCCGCCGATTATGGCGGGCGATCAGGTGCT

GGCCAACGGCGTGATTGATAGCGATGGCAACGTGATTTATACCTTCACCGATTATGTGAACACCAAAGATGATGTGAAAG

CGACCCTGACCATGCCGGCGTATATTGATCCGGAAAACGTGAAAAAAACCGGCAACGTGACCCTGGCCACCGGCATTGGT

AGCACCACCGCGAACAAAACCGTGCTGGTTGATTATGAAAAATACGGCAAATTCTATAACCTGAGCATCAAAGGCACCAT

TGATCAGATCGATAAAACCAACAACACCTATCGCCAGACCATTTATGTGAATCCGAGCGGCGATAACGTGATTGCGCCGG

TGCTGACCGGCAACCTGAAACCGAACACCGATAGCAACGCGCTGATTGATCAGCAGAACACCAGCATCAAAGTGTACAAA

GTGGATAACGCGGCGGATCTGAGCGAAAGCTATTTTGTGAATCCGGAAAACTTTGAAGATGTGACCAACAGCGTGAACAT

TACCTTTCCGAATCCGAACCAGTATAAAGTGGAATTTAACACCCCGGATGATCAGATTACCACCCCGTATATTGTGGTGG

TGAACGGCCATATTGATCCGAACAGCAAAGGCGATCTGGCCCTGCGTAGCACCCTGTATGGCTATAACAGCAACATTATT

TGGCGTAGCATGAGCTGGGATAACGAAGTGGCGTTTAACAACGGCAGCGGCAGCGGTGATGGCATTGATAAACCGGTGGT

GCCGGAACAGCCGGATGAACCGGGCGAAATTGAACCGATTCCGGAATAA
```

SEQ ID NO: 2 N1N2N3 ClfA His474 Nucleic acid
```
atgAGCGAAAACAGCGTGACCCAGAGCGATAGCGCGAGCAACGAAAGCAAAAGCAACGATAGCAGCAGCGTTAGCGC

AGCGCCGAAAACCGATGATACCAACGTGAGCGATACCAAAACCAGCAGCAACACCAACAACGGCGAAACCAGCGTGGCGC

AGAATCCGGCGCAGCAGGAAACCACCCAAAGCTCTAGCACCAACGCGACCACCGAAGAAACCCCGGTGACCGGCGAAGCG

ACCACCACGACGACCAACCAGGCGAATACCCCGGCGACCACCCAGTCTAGCAATACCAATGCGGAAGAACTGGTGAACCA

GACCAGCAACGAAACCACCTCTAATGATACCAACACCGTGAGCAGCGTGAACAGCCCGCAGAACAGCACCAATGCCGAAA

ACGTGAGCACCACCCAGGATACCAGCACCGAAGCGACCCCGAGCAACAACGAAAGCGCACCGCAAAGCACCGATGCGAGC

AACAAAGATGTGGTGAACCAGGCGGTGAATACCAGCGCACCGCGTATGCGTGCGTTTAGCCTGGCCGCGGTTGCGGCGGA

TGCGCCGGTTGCGGGCACCGATATCACCAACCAGCTGACGAACGTGACCGTGGGCATTGATAGCGGCACCACCGTGTATC

CGCATCAGGCGGGCTATGTGAAACTGAACTATGGCTTTAGCGTGCCGAACAGCGCGGTGAAAGGCGATACCTTTAAAATT

ACCGTGCCGAAAGAACTGAACCTGAACGGCGTGACCAGCACCGCGAAAGTGCCGCCGATTATGGCGGGCGATCAGGTGCT

GGCCAACGGCGTGATTGATAGCGATGGCAACGTGATTTATACCTTCACCGATTATGTGAACACCAAAGATGATGTGAAAG

CGACCCTGACCATGCCGGCGTATATTGATCCGGAAAACGTGAAAAAAACCGGCAACGTGACCCTGGCCACCGGCATTGGT

AGCACCACCGCGAACAAAACCGTGCTGGTTGATTATGAAAAATACGGCAAATTCTATAACCTGAGCATCAAAGGCACCAT

TGATCAGATCGATAAAACCAACAACACCTATCGCCAGACCATTTATGTGAATCCGAGCGGCGATAACGTGATTGCGCCGG

TGCTGACCGGCAACCTGAAACCGAACACCGATAGCAACGCGCTGATTGATCAGCAGAACACCAGCATCAAAGTGTACAAA

GTGGATAACGCGGCGGATCTGAGCGAAAGCTATTTTGTGAATCCGGAAAACTTTGAAGATGTGACCAACAGCGTGAACAT

TACCTTTCCGAATCCGAACCAGTATAAAGTGGAATTTAACACCCCGGATGATCAGATTACCACCCCGTATATTGTGGTGG

TGAACGGCCATATTGATCCGAACAGCAAAGGCGATCTGGCCCTGCGTAGCACCCTGTATGGCCATAACAGCAACATTATT

TGGCGTAGCATGAGCTGGGATAACGAAGTGGCGTTTAACAACGGCAGCGGCAGCGGTGATGGCATTGATAAACCGGTGGT

GCCGGAACAGCCGGATGAACCGGGCGAAATTGAACCGATTCCGGATAA
```

SEQ ID NO: 3 ClfA *S. aureus* strain NCTC8325
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

-continued

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGYNSNIIWRSMSWDNEVAFNNGSGSGDGID

KPVVPEQPDEPGEIEPIPEDSDSDPGSDSGSDSNSDSGSDSGSDSTSDSGSDSASDSDSA

SDSDSASDSDSASDSDSASDSDSDNDSDSDSDSDSDSDSDSDSDSDSDSDSDSDSDSDSD

SDSDSDSDSDSDSDSDSDSDSDSDSDSDSDSDSDSDSDSDSDSDSDSDSDSDSDSDSDSD

SDSDSDSDSDSDSDSDSDSDSDSDSDSDSDSDSDSDSDSDSDSASDSDSDSDSDSDSDSD

SDSDSDSDSDSDSDSDSDSDSESDSDSDSDSDSDSDSDSDSDSDSASDSDSGSD

SDSSSDSDSESDSNSDSESVSNNNVVPPNSPKNGTNASNKNEAKDSKEPLPDTGSEDEAN

TSLIWGLLASIGSLLLFRRKKENKDKK

SEQ ID NO: 4 ClfA N1N2N3 Ammino acid
MSENSVTQSDSASNESKSNDSSSVSAAPKTDDTNVSDTKTSSNTNNGETSVAQNPAQQETTQSSSTNATTEETPVTGEATT TTTNQANTPATTQSSNTNAEELVNQTSNETTSNDTNTVSSVNSPQNSTNAENVSTTQDTSTEATPSNNESAPQSTDASNKD VVNQAVNTSAPRMRAFSLAAVAADAPVAGTDITNQLTNVTVGIDSGTTVYPHQAGYVKLNYGFSVPNSAVKGDTFKITVPK ELNLNGVTSTAKVPPIMAGDQVLANGVIDSDGNVIYTFTDYVNTKDDVKATLTMPAYIDPENVKKTGNVTLATGIGSTTAN KTVLVDYEKYGKFYNLSIKGTIDQIDKTNNTYRQTIYVNPSGDNVIAPVLTGNLKPNTDSNALIDQQNTSIKVYKVDNAAD LSESYFVNPENFEDVTNSVNITFPNPNQYKVEFNTPDDQITTPYIVVVNGHIDPNSKGDLALRSTLYGYNSNIIWRSMSWD

NEVAFNNGSGSGDGIDKPVVPEQPDEPGEIEPIPE

SEQ ID NO: 5 ClfA N1-3
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGYNSNIIWRSMSWDNEVAFNNGSGSGDGID

KPVVPEQPDEPGEIEPIPE

SEQ ID NO: 6 ClfA N23
SLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGYNSNIIWRSMSWDNEVAFNNGSGSGDGID

KPVVPEQPDEPGEIEPIPE

SEQ ID NO: 7 ClfA N23 shorter
GTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGYNSNIIWRSMSWDNEVAFNNGSGSGDGID

KPVVPEQPDEPGEIEPIPE

SEQ ID NO: 8 ClfA S. aureus strain NCTC8325 H474
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGHNSNIIWRSMSWDNEVAFNNGSGSGDGID

KPVVPEQPDEPGEIEPIPEDSDSDPGSDSGSDSNSDSGSDSGSDSTSDSGSDSASDSDSA

SDSDSASDSDSASDSDSASDSDSDNDSDSDSDSDSDSDSDSDSDSDSDSDSDSDSDSDSD

SDSDSDSDSDSDSDSDSDSDSDSDSDSDSDSDSDSDSDSDSDSDSDSDSDSDSDSDSDSD

SDSDSDSDSDSDSDSDSDSDSDSDSDSDSDSDSDSDSDSDSASDSDSDSDSDSD

SDSDSDSDSDSDSDSDSDSDSDSESDSDSDSDSDSDSDSDSDSASDSDSGSD

SDSSSDSDSESDSNSDSESVSNNNVVPPNSPKNGTNASNKNEAKDSKEPLPDTGSEDEAN

TSLIWGLLASIGSLLLFRRKKENKDKK

SEQ ID NO: 9 ClfA N1N2N3 H474 Amino acid
MSENSVTQSDSASNESKSNDSSSVSAAPKTDDTNVSDTKTSSNTNNGETSVAQNPAQQETTQSSSTNATTEETPVTGEATT TTTNQANTPATTQSSNTNAEELVNQTSNETTSNDTNTVSSVNSPQNSTNAENVSTTQDTSTEATPSNNESAPQSTDASNKD VVNQAVNTSAPRMRAFSLAAVAADAPVAGTDITNQLTNVTVGIDSGTTVYPHQAGYVKLNYGFSVPNSAVKGDTFKITVPK ELNLNGVTSTAKVPPIMAGDQVLANGVIDSDGNVIYTFTDYVNTKDDVKATLTMPAYIDPENVKKTGNVTLATGIGSTTAN KTVLVDYEKYGKFYNLSIKGTIDQIDKTNNTYRQTIYVNPSGDNVIAPVLTGNLKPNTDSNALIDQQNTSIKVYKVDNAAD LSESYFVNPENFEDVTNSVNITFPNPNQYKVEFNTPDDQITTPYIVVVNGHIDPNSKGDLALRSTLYGHNSNIIWRSMSWD

NEVAFNNGSGSGDGIDKPVVPEQPDEPGEIEPIPE.

SEQ ID NO: 10 ClfA N1-3 H474
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

-continued

DQITTPYIVVVNGHIDPNSKGDLALRSTLYGHNSNIIWRSMSWDNEVAFNNGSGSGDGID

KPVVPEQPDEPGEIEPIPE

SEQ ID NO: 11 ClfA N23 H474
SLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGHNSNIIWRSMSWDNEVAFNNGSGSGDGID

KPVVPEQPDEPGEIEPIPE

SEQ ID NO: 12 ClfA N23 shorter H474
GTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGHNSNIIWRSMSWDNEVAFNNGSGSGDGID

KPVVPEQPDEPGEIEPIPE

SEQ ID NO: 13 ClfA S. aureus strain NCTC8325 del
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGNSNIIWRSMSWDNEVAFNNGSGSGDGID

KPVVPEQPDEPGEIEPIPEDSDSDPGSDSGSDSNSDSGSDSGSDSTSDSGSDSASDSDSA

SDSDSASDSDSASDSDSASDSDSDNDSDSDSDSDSDSDSDSDSDSDSDSDSDSDSDSDSD

SDSDSDSDSDSDSDSDSDSDSDSDSDSDSDSDSDSDSDSDSDSDSDSDSDSDSDSDSDSD

SDSDSDSDSDSDSDSDSDSDSDSDSDSDSDSDSDSDSASDSDSDSDSD

SDSDSDSDSDSDSDSDSDSDSESDSDSDSDSDSDSDSDSDSDSASDSDSGSD

SDSSSDSDSESDSNSDSESVSNNNVVPPNSPKNGTNASNKNEAKDSKEPLPDTGSEDEAN

TSLIWGLLASIGSLLLFRRKKENKDKK

SEQ ID NO: 14 ClfA N1N2N3 H474 Amino acid Del
MSENSVTQSDSASNESKSNDSSSVSAAPKTDDTNVSDTKTSSNTNNGETSVAQNPAQQETTQSSSTNATTEETPVTGEATT TTTNQANTPATTQSSNTNAEELVNQTSNETTSNDTNTVSSVNSPQNSTNAENVSTTQDTSTEATPSNNESAPQSTDASNKD VVNQAVNTSAPRMRAFSLAAVAADAPVAGTDITNQLTNVTVGIDSGTTVYPHQAGYVKLNYGFSVPNSAVKGDTFKITVPK ELNLNGVTSTAKVPPIMAGDQVLANGVIDSDGNVIYTFTDYVNTKDDVKATLTMPAYIDPENVKKTGNVTLATGIGSTTAN KTVLVDYEKYGKFYNLSIKGTIDQIDKTNNTYRQTIYVNPSGDNVIAPVLTGNLKPNTDSNALIDQQNTSIKVYKVDNAAD LSESYFVNPENFEDVTNSVNITFPNPNQYKVEFNTPDDQITTPYIVVVNGHIDPNSKGDLALRSTLYGNSNIIWRSMSWDN

EVAFNNGSGSGDGIDKPVVPEQPDEPGEIEPIPE.

SEQ ID NO: 15 ClfA N1-3 Del
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGNSNIIWRSMSWDNEVAFNNGSGSGDGID

KPVVPEQPDEPGEIEPIPE

SEQ ID NO: 16 ClfA N23 H474 del
SLAAVAADAPVAGTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGNSNIIWRSMSWDNEVAFNNGSGSGDGID

KPVVPEQPDEPGEIEPIPE

SEQ ID NO: 17 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGNSNIIWRSMSWDNEVAFNNGSGSGDGID

KPVVPEQPDEPGEIEPIPE

SEQ ID NO: 18 ClfA *S. aureus* strain NCTC8325 del
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYNSNIIWRSMSWDNEVAFNNGSGSGDGID

KPVVPEQPDEPGEIEPIPEDSDSDPGSDSGSDSNSDSGSDSGSDSTSDSGSDSASDSDSA

SDSDSASDSDSASDSDSASDSDSDNDSDSDSDSDSDSDSDSDSDSDSDSDSDSDSDSDSD

SDSDSDSDSDSDSDSDSDSDSDSDSDSDSDSDSDSDSDSDSDSDSDSDSDSDSDSDSDSD

SDSDSDSDSDSDSDSDSDSDSDSDSDSDSDSDSDSDSDSDSDSDSASDSDSDSDSDSDSD

SDSDSDSDSDSDSDSDSDSDSDSDSESDSDSDSDSDSDSDSDSDSDSASDSDSGSD

-continued

SDSSSDSDSESDSNSDSESVSNNNVVPPNSPKNGTNASNKNEAKDSKEPLPDTGSEDEAN

TSLIWGLLASIGSLLLFRRKKENKDKK

SEQ ID NO: 19 ClfA N1N2N3 del
MSENSVTQSDSASNESKSNDSSSVSAAPKTDDTNVSDTKTSSNTNNGETSVAQNPAQQETTQSSSTNATTEETPVTGEATT TTTNQANTPATTQSSNTNAEELVNQTSNETTSNDTNTVSSVNSPQNSTNAENVSTTQDTSTEATPSNNESAPQSTDASNKD VVNQAVNTSAPRMRAFSLAAVAADAPVAGTDITNQLTNVTVGIDSGTTVYPHQAGYVKLNYGFSVPNSAVKGDTFKITVPK ELNLNGVTSTAKVPPIMAGDQVLANGVIDSDGNVIYTFTDYVNTKDDVKATLTMPAYIDPENVKKTGNVTLATGIGSTTAN KTVLVDYEKYGKFYNLSIKGTIDQIDKTNNTYRQTIYVNPSGDNVIAPVLTGNLKPNTDSNALIDQQNTSIKVYKVDNAAD LSESYFVNPENFEDVTNSVNITFPNPNQYKVEFNTPDDQITTPYIVVVNGHIDPNSKGDLALRSTLYNSNIIWRSMSWDNE

VAFNNGSGSDGIDKPVVPEQPDEPGEIEPIPE.

SEQ ID NO: 20 ClfA N1-3 del
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYNSNIIWRSMSWDNEVAFNNGSGSDGID

KPVVPEQPDEPGEIEPIPE

SEQ ID NO: 21 ClfA N23 del
SLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYNSNIIWRSMSWDNEVAFNNGSGSDGID

KPVVPEQPDEPGEIEPIPE

SEQ ID NO: 22 ClfA N23 shorter del
GTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYNSNIIWRSMSWDNEVAFNNGSGSDGID

KPVVPEQPDEPGEIEPIPE

SEQ ID NO: 23 ClfA S. aureus strain NCTC8325 del
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

-continued

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYSNIIWRSMSWDNEVAFNNGSGSGDGID

KPVVPEQPDEPGEIEPIPEDSDSDPGSDSGSDSNSDSGSDSGSDSTSDSGSDSASDSDSA

SDSDSASDSDSASDSDSASDSDSDNDSDSDSDSDSDSDSDSDSDSDSDSDSDSDSDSDSD

SDSDSDSDSDSDSDSDSDSDSDSDSDSDSDSDSDSDSDSDSDSDSDSDSDSDSDSDSDSD

SDSDSDSDSDSDSDSDSDSDSDSDSDSDSDSDSDSDSDSDSASDSDSDSDSDSD

SDSDSDSDSDSDSDSDSDSDSDSESDSDSDSDSDSDSDSDSDSDSASDSDSGSD

SDSSSDSDSESDSNSDSESVSNNNVVPPNSPKNGTNASNKNEAKDSKEPLPDTGSEDEAN

TSLIWGLLASIGSLLLFRRKKENKDKK

SEQ ID NO: 24 ClfA N1N2N3 del
MSENSVTQSDSASNESKSNDSSSVSAAPKTDDTNVSDTKTSSNTNNGETSVAQNPAQQETTQSSSTNATTEETPVTGEATT TTTNQANTPATTQSSNTNAEELVNQTSNETTSNDTNTVSSVNSPQNSTNAENVSTTQDTSTEATPSNNESAPQSTDASNKD VVNQAVNTSAPRMRAFSLAAVAADAPVAGTDITNQLTNVTVGIDSGTTVYPHQAGYVKLNYGFSVPNSAVKGDTFKITVPK ELNLNGVTSTAKVPPIMAGDQVLANGVIDSDGNVIYTFTDYVNTKDDVKATLTMPAYIDPENVKKTGNVTLATGIGSTTAN KTVLVDYEKYGKFYNLSIKGTIDQIDKTNNTYRQTIYVNPSGDNVIAPVLTGNLKPNTDSNALIDQQNTSIKVYKVDNAAD LSESYFVNPENFEDVTNSVNITFPNPNQYKVEFNTPDDQITTPYIVVVNGHIDPNSKGDLALRSTLYSNIIWRSMSWDNEV

AFNNGSGSGDGIDKPVVPEQPDEPGEIEPIPE.

SEQ ID NO: 25 ClfA N1-3 del
MNMKKKEKHAIRKKSIGVASVLVGTLIGFGLLSSKEADASENSVTQSDSASNESKSNDSS

SVSAAPKTDDTNVSDTKTSSNTNNGETSVAQNPAQQETTQSSSTNATTEETPVTGEATTT

TTNQANTPATTQSSNTNAEELVNQTSNETTSNDTNTVSSVNSPQNSTNAENVSTTQDTST

EATPSNNESAPQSTDASNKDVVNQAVNTSAPRMRAFSLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYSNIIWRSMSWDNEVAFNNGSGSGDGID

KPVVPEQPDEPGEIEPIPE

SEQ ID NO: 26 ClfA N23 del
SLAAVAADAPVAGTDITNQLTNVT

VGIDSGTTVYPHQAGYVKLNYGFSVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYSNIIWRSMSWDNEVAFNNGSGSGDGID

KPVVPEQPDEPGEIEPIPE

SEQ ID NO: 27 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

-continued

DSNALIDQQNTSIKVYKVDNAADLSESYFVNPENFEDVTNSVNITFPNPNQYKVEFNTPD

DQITTPYIVVVNGHIDPNSKGDLALRSTLYSNIIWRSMSWDNEVAFNNGSGSGDGID

KPVVPEQPDEPGEIEPIPE

SEQ ID NO: 28 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGSNIIWRSMSWDNEVAFNNGSGSGDGID

KPVVPEQPDEPGEIEPIPE

SEQ ID NO: 29 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYNIIWRSMSWDNEVAFNNGSGSGDGID

KPVVPEQPDEPGEIEPIPE

SEQ ID NO: 30 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGIIWRSMSWDNEVAFNNGSGSGDGID

KPVVPEQPDEPGEIEPIPE

SEQ ID NO: 31 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLSNIIWRSMSWDNEVAFNNGSGSGDGID

KPVVPEQPDEPGEIEPIPE

SEQ ID NO: 32 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTNSNIIWRSMSWDNEVAFNNGSGSGDGID

KPVVPEQPDEPGEIEPIPE

SEQ ID NO: 33 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSNSNIIWRSMSWDNEVAFNNGSGSGDGID

KPVVPEQPDEPGEIEPIPE

SEQ ID NO: 34 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTSNIIWRSMSWDNEVAFNNGSGSGDGID

KPVVPEQPDEPGEIEPIPE

SEQ ID NO: 35 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYIIWRSMSWDNEVAFNNGSGSGDGID

KPVVPEQPDEPGEIEPIPE

SEQ ID NO: 36 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYGWRSMSWDNEVAFNNGSGSGDGID

KPVVPEQPDEPGEIEPIPE

SEQ ID NO: 37 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLYIWRSMSWDNEVAFNNGSGSGDGID

KPVVPEQPDEPGEIEPIPE

SEQ ID NO: 38 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTLIIWRSMSWDNEVAFNNGSGSGDGID

KPVVPEQPDEPGEIEPIPE

SEQ ID NO: 39 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTNIIWRSMSWDNEVAFNNGSGSGDGID

KPVVPEQPDEPGEIEPIPE

SEQ ID NO: 40 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSSNIIWRSMSWDNEVAFNNGSGSGDGID

KPVVPEQPDEPGEIEPIPE

SEQ ID NO: 41 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRNSNIIWRSMSWDNEVAFNNGSGSGDGID

KPVVPEQPDEPGEIEPIPE

SEQ ID NO: 42 ClfA N23 shorter del
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSTIIWRSMSWDNEVAFNNGSGSGDGID

KPVVPEQPDEPGEIEPIPE

SEQ ID NO: 43 ClfA N23 shorter
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

-continued

DQITTPYIVVVNGHIDPNSKGDLALRSIIWRSMSWDNEVAFNNGSGSGDGID

KPVVPEQPDEPGEIEPIPE

SEQ ID NO: 44 ClfA N23 shorter
GTDITNQLTNVT

VGIDSGTTVYPHQAGYVKLNYGESVPNSAVKGDTFKITVPKELNLNGVTSTAKVPPIMAG

DQVLANGVIDSDGNVIYTFTDYVNTKDDVKATLTMPAYIDPENVKKTGNVTLATGIGSTT

ANKTVLVDYEKYGKFYNLSIKGTIDQIDKTNNTYRQTIYVNPSGDNVIAPVLTGNLKPNT

DSNALIDQQNTSIKVYKVDNAADLSESYFVNPENFEDVTNSVNITFPNPNQYKVEFNTPD

DQITTPYIVVVNGHIDPNSKGDLALRSIWRSMSWDNEVAFNNGSGSGDGID

KPVVPEQPDEPGEIEPIPE

---

The invention claimed is:

1. A Clumping factor A (ClfA) polypeptide comprising SEQ ID NO: 12.

2. An immunogenic composition comprising the ClfA polypeptide of claim 1 and a pharmaceutically acceptable excipient.

3. A process for making an immunogenic composition comprising the step of adding a pharmaceutically acceptable excipient to the ClfA polypeptide of claim 1.

4. A method of treating staphylococcal infection comprising administering the ClfA polypeptide of claim 1 to a patient in need thereof.

5. A method of treating staphylococcal infection comprising administering the immunogenic composition of claim 2 to a patient in need thereof.

6. A fragment of the ClfA polypeptide of claim 1 comprising the amino acid sequence DLALRSTLYGHNSNIIWRSM (SEQ ID NO: 45).

7. An immunogenic composition comprising the ClfA polypeptide of claim 6 and a pharmaceutically acceptable excipient.

* * * * *

SEQUENCE LISTING

<160> NUMBER OF SEQ ID NOS: 45

<210> SEQ ID NO 1
<211> LENGTH: 1566
<212> TYPE: DNA
<213> ORGANISM: Staphylococcus aureus

<400> SEQUENCE: 1

```
atgagcgaaa acagcgtgac ccagagcgat agcgcgagca cgaaagcaa aagcaacgat      60
agcagcagcg ttagcgcagc gccgaaaacc gatgatacca acgtgagcga taccaaaacc     120
agcagcaaca ccaacaacgg cgaaaccagc gtggcgcaga tccggcgca gcaggaaacc      180
acccaaagct ctagcaccaa cgcgaccacc gaagaaaccc cggtgaccgg cgaagcgacc     240
accacgacga ccaaccaggc gaataccccg cgaccaccc agtctagcaa taccaatgcg      300
gaagaactgg tgaaccagac cagcaacgaa accacctcta tgataccaa caccgtgagc      360
agcgtgaaca gcccgcagaa cagcaccaat gccgaaaacg tgagcaccac ccaggatacc     420
agcaccgaag cgaccccgag caacaacgaa agcgcaccgc aaagcaccga tgcgagcaac     480
aaagatgtgg tgaaccaggc ggtgaatacc agcgcaccgc gtatgcgtgc gtttagcctg     540
gccgcggttg cggcggatgc gccggttgcg ggcaccgata tcaccaacca gctgacgaac     600
gtgaccgtgg gcattgatag cggcaccacc gtgtatccgc atcaggcggg ctatgtgaaa     660
ctgaactatg gctttagcgt gccgaacagc gcggtgaaag cgatacctt taaaattacc      720
gtgccgaaag aactgaacct gaacggcgtg accagcaccg cgaaagtgcc gccgattatg     780
gcgggcgatc aggtgctggc caacggcgtg attgatagcg atggcaacgt gatttatacc     840
ttcaccgatt atgtgaacac caaagatgat gtgaaagcga ccctgaccat gccggcgtat     900
attgatccgg aaaacgtgaa aaaaaccggc aacgtgaccc tggccaccgg cattggtagc     960
accaccgcga caaaaccgt gctggttgat tatgaaaaat acggcaaatt ctataacctg    1020
agcatcaaag gcaccattga tcagatcgat aaaaccaaca cacctatcg ccagaccatt    1080
tatgtgaatc cgagcggcga taacgtgatt gcgccggtgc tgaccggcaa cctgaaaccg    1140
aacaccgata gcaacgcgct gattgatcag cagaacacca gcatcaaagt gtacaaagtg    1200
gataacgcgg cggatctgag cgaaagctat tttgtgaatc cggaaaactt tgaagatgtg    1260
accaacagcg tgaacattac ctttccgaat ccgaaccagt ataaagtgga atttaacacc    1320
ccggatgatc agattaccac cccgtatatt gtggtggtga acggccatat tgatccgaac    1380
```

```
agcaaaggcg atctggccct gcgtagcacc ctgtatggct ataacagcaa cattatttgg    1440
cgtagcatga gctgggataa cgaagtggcg tttaacaacg gcagcggcag cggtgatggc    1500
attgataaac cggtggtgcc ggaacagccg gatgaaccgg gcgaaattga accgattccg    1560
gaataa                                                               1566

<210> SEQ ID NO 2
<211> LENGTH: 1565
<212> TYPE: DNA
<213> ORGANISM: Staphylococcus aureus

<400> SEQUENCE: 2
atgagcgaaa acagcgtgac ccagagcgat agcgcgagca cgaaagcaa aagcaacgat      60 agcagcagcg ttagcgcagc gccgaaaacc gatgatacca cgtgagcga taccaaaacc     120 agcagcaaca ccaacaacgg cgaaaccagc gtggcgcaga tccggcgca gcaggaaacc     180 acccaaagct ctagcaccaa cgcgaccacc gaagaaaccc cggtgaccgg cgaagcgacc    240
accacgacga ccaaccaggc gaataccccg gcgaccaccc agtctagcaa taccaatgcg    300
gaagaactgg tgaaccagac cagcaacgaa accacctcta tgataccaa caccgtgagc    360 agcgtgaaca gcccgcagaa cagcaccaat gccgaaaacg tgagcaccac ccaggatacc    420
agcaccgaag cgaccccgag caacaacgaa agcgcaccgc aaagcaccga tgcgagcaac    480
aaagatgtgg tgaaccaggc ggtgaatacc agcgcaccgc gtatgcgtgc gtttagcctg    540
gccgcggttg cggcggatgc gccggttgcg ggcaccgata tcaccaacca gctgacgaac    600
gtgaccgtgg gcattgatag cggcaccacc gtgtatccgc atcaggcggg ctatgtgaaa    660
ctgaactatg gctttagcgt gccgaacagc gcggtgaaag cgatacctt taaaattacc      720 gtgccgaaag aactgaacct gaacggcgtg accagcaccg cgaaagtgcc gccgattatg    780
gcgggcgatc aggtgctggc caacggcgtg attgatagcg atggcaacgt gatttatacc    840
ttcaccgatt atgtgaacac caaagatgat gtgaaagcga ccctgaccat gccggcgtat    900
attgatccgg aaacgtgaa aaaaccggc aacgtgaccc tggccaccgg cattggtagc      960
accaccgcga caaaaccgt gctggttgat tatgaaaaat acggcaaatt ctataacctg    1020
agcatcaaag gcaccattga tcagatcgat aaaaccaaca cacctatcg ccagaccatt    1080 tatgtgaatc cgagcggcga taacgtgatt gcgccggtgc tgaccggcaa cctgaaaccg    1140
aacaccgata gcaacgcgct gattgatcag cagaacacca gcatcaaagt gtacaaagtg    1200
gataacgcgc cggatctgag cgaaagctat tttgtgaatc cggaaaactt tgaagatgtg    1260
accaacagcg tgaacattac cttccgaat ccgaaccagt ataaagtgga atttaacacc    1320
ccggatgatc agattaccac cccgtatatt gtggtggtga acggccatat tgatccgaac    1380
agcaaaggcg atctggcct gcgtagcacc ctgtatggcc ataacagcaa cattatttgg    1440
cgtagcatga gctgggataa cgaagtggcg tttaacaacg gcagcggcag cggtgatggc    1500
attgataaac cggtggtgcc ggaacagccg gatgaaccgg gcgaaattga accgattccg    1560
gataa                                                                1565

<210> SEQ ID NO 3
<211> LENGTH: 927
<212> TYPE: PRT
<213> ORGANISM: Staphylococcus aureus

<400> SEQUENCE: 3

Met Asn Met Lys Lys Lys Glu Lys His Ala Ile Arg Lys Lys Ser Ile
  1               5                  10                  15
```

```
Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
            115                 120                 125

Ala Thr Thr Gln Ser Ser Asn Thr Asn Ala Glu Glu Leu Val Asn Gln
        130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
```

```
                435                 440                 445
Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                    485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
            530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                    565                 570                 575

Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
            595                 600                 605

Ser Asp Ser Ala Ser Asp Ser Ala Ser Asp Ser Ala Ser Asp Ser Asp
610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
                    645                 650                 655

Ser Asp Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp Ser Asp
            690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                    725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
            755                 760                 765

Ser Asp Ser Asp Ser Asp Ser Asp Ser Asp Ser Asp Ser Asp Ser Asp
770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Asp Ser Asp
                    805                 810                 815

Ser Asp Ser Asp Ser Asp Ser Asp Ser Asp Ser Asp Ser Asp Ser Ala
            820                 825                 830

Ser Asp Ser Asp Ser Gly Ser Asp Ser Asp Ser Ser Ser Asp Ser Asp
            835                 840                 845

Ser Glu Ser Asp Ser Asn Ser Asp Ser Glu Ser Val Ser Asn Asn Asn
            850                 855                 860
```

-continued

Val Val Pro Pro Asn Ser Pro Lys Asn Gly Thr Asn Ala Ser Asn Lys
865                 870                 875                 880

Asn Glu Ala Lys Asp Ser Lys Glu Pro Leu Pro Asp Thr Gly Ser Glu
            885                 890                 895

Asp Glu Ala Asn Thr Ser Leu Ile Trp Gly Leu Leu Ala Ser Ile Gly
            900                 905                 910

Ser Leu Leu Leu Phe Arg Arg Lys Lys Glu Asn Lys Asp Lys Lys
        915                 920                 925

<210> SEQ ID NO 4
<211> LENGTH: 521
<212> TYPE: PRT
<213> ORGANISM: Staphylococcus aureus

<400> SEQUENCE: 4

Met Ser Glu Asn Ser Val Thr Gln Ser Asp Ser Ala Ser Asn Glu Ser
1               5                   10                  15

Lys Ser Asn Asp Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
            35                  40                  45

Thr Ser Val Ala Gln Asn Pro Ala Gln Gln Glu Thr Thr Gln Ser Ser
50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Thr Gln Ser Ser
            85                  90                  95

Asn Thr Asn Ala Glu Glu Leu Val Asn Gln Thr Ser Asn Glu Thr Thr
            100                 105                 110

Ser Asn Asp Thr Asn Thr Val Ser Ser Val Asn Ser Pro Gln Asn Ser
        115                 120                 125

Thr Asn Ala Glu Asn Val Ser Thr Thr Gln Asp Thr Ser Thr Glu Ala
    130                 135                 140

Thr Pro Ser Asn Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
            165                 170                 175

Ala Phe Ser Leu Ala Ala Val Ala Ala Asp Ala Pro Val Ala Gly Thr
            180                 185                 190

Asp Ile Thr Asn Gln Leu Thr Asn Val Thr Val Gly Ile Asp Ser Gly
        195                 200                 205

Thr Thr Val Tyr Pro His Gln Ala Gly Tyr Val Lys Leu Asn Tyr Gly
    210                 215                 220

Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
            245                 250                 255

Pro Pro Ile Met Ala Gly Asp Gln Val Leu Ala Asn Gly Val Ile Asp
            260                 265                 270

Ser Asp Gly Asn Val Ile Tyr Thr Phe Thr Asp Tyr Val Asn Thr Lys
        275                 280                 285

Asp Asp Val Lys Ala Thr Leu Thr Met Pro Ala Tyr Ile Asp Pro Glu
    290                 295                 300

Asn Val Lys Lys Thr Gly Asn Val Thr Leu Ala Thr Gly Ile Gly Ser
305                 310                 315                 320

-continued

Thr Thr Ala Asn Lys Thr Val Leu Val Asp Tyr Glu Lys Tyr Gly Lys
            325                 330                 335

Phe Tyr Asn Leu Ser Ile Lys Gly Thr Ile Asp Gln Ile Asp Lys Thr
            340                 345                 350

Asn Asn Thr Tyr Arg Gln Thr Ile Tyr Val Asn Pro Ser Gly Asp Asn
            355                 360                 365

Val Ile Ala Pro Val Leu Thr Gly Asn Leu Lys Pro Asn Thr Asp Ser
        370                 375                 380

Asn Ala Leu Ile Asp Gln Gln Asn Thr Ser Ile Lys Val Tyr Lys Val
385                 390                 395                 400

Asp Asn Ala Ala Asp Leu Ser Glu Ser Tyr Phe Val Asn Pro Glu Asn
            405                 410                 415

Phe Glu Asp Val Thr Asn Ser Val Asn Ile Thr Phe Pro Asn Pro Asn
            420                 425                 430

Gln Tyr Lys Val Glu Phe Asn Thr Pro Asp Asp Gln Ile Thr Thr Pro
            435                 440                 445

Tyr Ile Val Val Val Asn Gly His Ile Asp Pro Asn Ser Lys Gly Asp
        450                 455                 460

Leu Ala Leu Arg Ser Thr Leu Tyr Gly Tyr Asn Ser Asn Ile Ile Trp
465                 470                 475                 480

Arg Ser Met Ser Trp Asp Asn Glu Val Ala Phe Asn Asn Gly Ser Gly
            485                 490                 495

Ser Gly Asp Gly Ile Asp Lys Pro Val Val Pro Glu Gln Pro Asp Glu
            500                 505                 510

Pro Gly Glu Ile Glu Pro Ile Pro Glu
            515                 520

<210> SEQ ID NO 5
<211> LENGTH: 559
<212> TYPE: PRT
<213> ORGANISM: Staphylococcus aureus

<400> SEQUENCE: 5

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
            85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
            115                 120                 125

Ala Thr Thr Gln Ser Ser Asn Thr Asn Ala Glu Glu Leu Val Asn Gln
        130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
            165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 6
<211> LENGTH: 343
<212> TYPE: PRT
<213> ORGANISM: Staphylococcus aureus

<400> SEQUENCE: 6

```
Ser Leu Ala Ala Val Ala Ala Asp Ala Pro Val Ala Gly Thr Asp Ile
 1               5                  10                  15

Thr Asn Gln Leu Thr Asn Val Thr Val Gly Ile Asp Ser Gly Thr Thr
            20                  25                  30

Val Tyr Pro His Gln Ala Gly Tyr Val Lys Leu Asn Tyr Gly Phe Ser
            35                  40                  45

Val Pro Asn Ser Ala Val Lys Gly Asp Thr Phe Lys Ile Thr Val Pro
        50                  55                  60

Lys Glu Leu Asn Leu Asn Gly Val Thr Ser Thr Ala Lys Val Pro Pro
65                  70                  75                  80

Ile Met Ala Gly Asp Gln Val Leu Ala Asn Gly Val Ile Asp Ser Asp
                85                  90                  95

Gly Asn Val Ile Tyr Thr Phe Thr Asp Tyr Val Asn Thr Lys Asp Asp
                100                 105                 110

Val Lys Ala Thr Leu Thr Met Pro Ala Tyr Ile Asp Pro Glu Asn Val
            115                 120                 125

Lys Lys Thr Gly Asn Val Thr Leu Ala Thr Gly Ile Gly Ser Thr Thr
        130                 135                 140

Ala Asn Lys Thr Val Leu Val Asp Tyr Glu Lys Tyr Gly Lys Phe Tyr
145                 150                 155                 160

Asn Leu Ser Ile Lys Gly Thr Ile Asp Gln Ile Asp Lys Thr Asn Asn
                165                 170                 175

Thr Tyr Arg Gln Thr Ile Tyr Val Asn Pro Ser Gly Asp Asn Val Ile
                180                 185                 190

Ala Pro Val Leu Thr Gly Asn Leu Lys Pro Asn Thr Asp Ser Asn Ala
            195                 200                 205

Leu Ile Asp Gln Gln Asn Thr Ser Ile Lys Val Tyr Lys Val Asp Asn
210                 215                 220

Ala Ala Asp Leu Ser Glu Ser Tyr Phe Val Asn Pro Glu Asn Phe Glu
225                 230                 235                 240

Asp Val Thr Asn Ser Val Asn Ile Thr Phe Pro Asn Pro Asn Gln Tyr
                245                 250                 255

Lys Val Glu Phe Asn Thr Pro Asp Asp Gln Ile Thr Thr Pro Tyr Ile
                260                 265                 270

Val Val Val Asn Gly His Ile Asp Pro Asn Ser Lys Gly Asp Leu Ala
            275                 280                 285

Leu Arg Ser Thr Leu Tyr Gly Tyr Asn Ser Asn Ile Ile Trp Arg Ser
        290                 295                 300

Met Ser Trp Asp Asn Glu Val Ala Phe Asn Asn Gly Ser Gly Ser Gly
305                 310                 315                 320

Asp Gly Ile Asp Lys Pro Val Val Pro Glu Gln Pro Asp Glu Pro Gly
                325                 330                 335

Glu Ile Glu Pro Ile Pro Glu
                340

<210> SEQ ID NO 7
<211> LENGTH: 331
<212> TYPE: PRT
<213> ORGANISM: Staphylococcus aureus

<400> SEQUENCE: 7

Gly Thr Asp Ile Thr Asn Gln Leu Thr Asn Val Thr Val Gly Ile Asp
 1               5                  10                  15

Ser Gly Thr Thr Val Tyr Pro His Gln Ala Gly Tyr Val Lys Leu Asn
            20                  25                  30
```

```
Tyr Gly Phe Ser Val Pro Asn Ser Ala Val Lys Gly Asp Thr Phe Lys
             35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

Ile Asp Ser Asp Gly Asn Val Ile Tyr Thr Phe Thr Asp Tyr Val Asn
                 85                  90                  95

Thr Lys Asp Asp Val Lys Ala Thr Leu Thr Met Pro Ala Tyr Ile Asp
                100                 105                 110

Pro Glu Asn Val Lys Lys Thr Gly Asn Val Thr Leu Ala Thr Gly Ile
            115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
                180                 185                 190

Asp Ser Asn Ala Leu Ile Asp Gln Gln Asn Thr Ser Ile Lys Val Tyr
            195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
                260                 265                 270

Gly Asp Leu Ala Leu Arg Ser Thr Leu Tyr Gly Tyr Asn Ser Asn Ile
            275                 280                 285

Ile Trp Arg Ser Met Ser Trp Asp Asn Glu Val Ala Phe Asn Asn Gly
290                 295                 300

Ser Gly Ser Gly Asp Gly Ile Asp Lys Pro Val Val Pro Glu Gln Pro
305                 310                 315                 320

Asp Glu Pro Gly Glu Ile Glu Pro Ile Pro Glu
                325                 330

<210> SEQ ID NO 8
<211> LENGTH: 927
<212> TYPE: PRT
<213> ORGANISM: Staphylococcus aureus

<400> SEQUENCE: 8

Met Asn Met Lys Lys Glu Lys His Ala Ile Arg Lys Lys Ser Ile
 1               5                  10                  15

Gly Val Ala Ser Val Leu Val Gly Thr Leu Ile Gly Phe Gly Leu Leu
             20                  25                  30

Ser Ser Lys Glu Ala Asp Ala Ser Glu Asn Ser Val Thr Gln Ser Asp
             35                  40                  45

Ser Ala Ser Asn Glu Ser Lys Ser Asn Asp Ser Ser Ser Val Ser Ala
 50                  55                  60

Ala Pro Lys Thr Asp Asp Thr Asn Val Ser Asp Thr Lys Thr Ser Ser
 65                  70                  75                  80
```

```
Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly His
            500                 505                 510
```

```
Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
            595                 600                 605

Ser Asp Ser Ala Ser Asp Ser Asp Ser Ala Ser Asp Ser Asp Ser Asp
            610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
            645                 650                 655

Ser Asp Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp Ser Asp
            690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
            755                 760                 765

Ser Asp Ser Asp Ser Asp Ser Asp Ser Asp Ser Asp Ser Asp Ser Asp
            770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Asp Ser Asp
                805                 810                 815

Ser Asp Ser Asp Ser Asp Ser Asp Ser Asp Ser Asp Ser Asp Ser Ala
            820                 825                 830

Ser Asp Ser Asp Ser Gly Ser Asp Ser Asp Ser Ser Ser Asp Ser Asp
            835                 840                 845

Ser Glu Ser Asp Ser Asn Ser Asp Ser Glu Ser Val Ser Asn Asn Asn
850                 855                 860

Val Val Pro Pro Asn Ser Pro Lys Asn Gly Thr Asn Ala Ser Asn Lys
865                 870                 875                 880

Asn Glu Ala Lys Asp Ser Lys Glu Pro Leu Pro Asp Thr Gly Ser Glu
                885                 890                 895

Asp Glu Ala Asn Thr Ser Leu Ile Trp Gly Leu Leu Ala Ser Ile Gly
            900                 905                 910

Ser Leu Leu Leu Phe Arg Arg Lys Lys Glu Asn Lys Asp Lys Lys
            915                 920                 925
```

<210> SEQ ID NO 9
<211> LENGTH: 521
<212> TYPE: PRT
<213> ORGANISM: Staphylococcus aureus

<400> SEQUENCE: 9

Met Ser Glu Asn Ser Val Thr Gln Ser Asp Ser Ala Ser Asn Glu Ser
1               5                   10                  15

Lys Ser Asn Asp Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
            35                  40                  45

Thr Ser Val Ala Gln Asn Pro Ala Gln Gln Glu Thr Thr Gln Ser Ser
        50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Thr Gln Ser Ser
                85                  90                  95

Asn Thr Asn Ala Glu Glu Leu Val Asn Gln Thr Ser Asn Glu Thr Thr
            100                 105                 110

Ser Asn Asp Thr Asn Thr Val Ser Val Asn Ser Pro Gln Asn Ser
            115                 120                 125

Thr Asn Ala Glu Asn Val Ser Thr Thr Gln Asp Thr Ser Thr Glu Ala
        130                 135                 140

Thr Pro Ser Asn Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
                165                 170                 175

Ala Phe Ser Leu Ala Ala Val Ala Asp Ala Pro Val Ala Gly Thr
            180                 185                 190

Asp Ile Thr Asn Gln Leu Thr Asn Val Thr Val Gly Ile Asp Ser Gly
            195                 200                 205

Thr Thr Val Tyr Pro His Gln Ala Gly Tyr Val Lys Leu Asn Tyr Gly
        210                 215                 220

Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
                245                 250                 255

Pro Pro Ile Met Ala Gly Asp Gln Val Leu Ala Asn Gly Val Ile Asp
            260                 265                 270

Ser Asp Gly Asn Val Ile Tyr Thr Phe Thr Asp Tyr Val Asn Thr Lys
        275                 280                 285

Asp Asp Val Lys Ala Thr Leu Thr Met Pro Ala Tyr Ile Asp Pro Glu
    290                 295                 300

Asn Val Lys Lys Thr Gly Asn Val Thr Leu Ala Thr Gly Ile Gly Ser
305                 310                 315                 320

Thr Thr Ala Asn Lys Thr Val Leu Val Asp Tyr Glu Lys Tyr Gly Lys
                325                 330                 335

Phe Tyr Asn Leu Ser Ile Lys Gly Thr Ile Asp Gln Ile Asp Lys Thr
            340                 345                 350

Asn Asn Thr Tyr Arg Gln Thr Ile Tyr Val Asn Pro Ser Gly Asp Asn
        355                 360                 365

Val Ile Ala Pro Val Leu Thr Gly Asn Leu Lys Pro Asn Thr Asp Ser
    370                 375                 380

Asn Ala Leu Ile Asp Gln Gln Asn Thr Ser Ile Lys Val Tyr Lys Val

-continued

```
                385                 390                 395                 400
Asp Asn Ala Ala Asp Leu Ser Glu Ser Tyr Phe Val Asn Pro Glu Asn
                    405                 410                 415

Phe Glu Asp Val Thr Asn Ser Val Asn Ile Thr Phe Pro Asn Pro Asn
                420                 425                 430

Gln Tyr Lys Val Glu Phe Asn Thr Pro Asp Asp Gln Ile Thr Thr Pro
            435                 440                 445

Tyr Ile Val Val Asn Gly His Ile Asp Pro Asn Ser Lys Gly Asp
        450                 455                 460

Leu Ala Leu Arg Ser Thr Leu Tyr Gly His Asn Ser Asn Ile Ile Trp
465                 470                 475                 480

Arg Ser Met Ser Trp Asp Asn Glu Val Ala Phe Asn Asn Gly Ser Gly
                485                 490                 495

Ser Gly Asp Gly Ile Asp Lys Pro Val Val Pro Glu Gln Pro Asp Glu
                500                 505                 510

Pro Gly Glu Ile Glu Pro Ile Pro Glu
            515                 520

<210> SEQ ID NO 10
<211> LENGTH: 559
<212> TYPE: PRT
<213> ORGANISM: Staphylococcus aureus

<400> SEQUENCE: 10

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
                100                 105                 110

Val Thr Gly Glu Ala Thr Thr Thr Thr Thr Asn Gln Ala Asn Thr Pro
            115                 120                 125

Ala Thr Thr Gln Ser Ser Asn Thr Asn Ala Glu Glu Leu Val Asn Gln
        130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Glu Ser Ala Pro Gln
                180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
        210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
```

245                 250                 255
Val Lys Leu Asn Tyr Gly Phe Ser Val Pro Asn Ser Ala Val Lys Gly
                260                 265                 270

Asp Thr Phe Lys Ile Thr Val Pro Lys Glu Leu Asn Leu Asn Gly Val
                275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
                340                 345                 350

Ala Thr Gly Ile Gly Ser Thr Thr Ala Asn Lys Thr Val Leu Val Asp
                355                 360                 365

Tyr Glu Lys Tyr Gly Lys Phe Tyr Asn Leu Ser Ile Lys Gly Thr Ile
                370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Asn Thr Ser
                420                 425                 430

Ile Lys Val Tyr Lys Val Asp Asn Ala Ala Asp Leu Ser Glu Ser Tyr
                435                 440                 445

Phe Val Asn Pro Glu Asn Phe Glu Asp Val Thr Asn Ser Val Asn Ile
                450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly His
                500                 505                 510

Asn Ser Asn Ile Ile Trp Arg Ser Met Ser Trp Asp Asn Glu Val Ala
                515                 520                 525

Phe Asn Asn Gly Ser Gly Ser Gly Asp Gly Ile Asp Lys Pro Val Val
                530                 535                 540

Pro Glu Gln Pro Asp Glu Pro Gly Glu Ile Glu Pro Ile Pro Glu
545                 550                 555

<210> SEQ ID NO 11
<211> LENGTH: 343
<212> TYPE: PRT
<213> ORGANISM: Staphylococcus aureus

<400> SEQUENCE: 11

Ser Leu Ala Ala Val Ala Ala Asp Ala Pro Val Ala Gly Thr Asp Ile
1               5                   10                  15

Thr Asn Gln Leu Thr Asn Val Thr Val Gly Ile Asp Ser Gly Thr Thr
                20                  25                  30

Val Tyr Pro His Gln Ala Gly Tyr Val Lys Leu Asn Tyr Gly Phe Ser
                35                  40                  45

Val Pro Asn Ser Ala Val Lys Gly Asp Thr Phe Lys Ile Thr Val Pro
                50                  55                  60

Lys Glu Leu Asn Leu Asn Gly Val Thr Ser Thr Ala Lys Val Pro Pro

```
                65                  70                  75                  80
        Ile Met Ala Gly Asp Gln Val Leu Ala Asn Gly Val Ile Asp Ser Asp
                            85                  90                  95

Gly Asn Val Ile Tyr Thr Phe Thr Asp Tyr Val Asn Thr Lys Asp Asp
                        100                 105                 110

Val Lys Ala Thr Leu Thr Met Pro Ala Tyr Ile Asp Pro Glu Asn Val
                    115                 120                 125

Lys Lys Thr Gly Asn Val Thr Leu Ala Thr Gly Ile Gly Ser Thr Thr
        130                 135                 140

Ala Asn Lys Thr Val Leu Val Asp Tyr Glu Lys Tyr Gly Lys Phe Tyr
        145                 150                 155                 160

Asn Leu Ser Ile Lys Gly Thr Ile Asp Gln Ile Asp Lys Thr Asn Asn
                        165                 170                 175

Thr Tyr Arg Gln Thr Ile Tyr Val Asn Pro Ser Gly Asp Asn Val Ile
                    180                 185                 190

Ala Pro Val Leu Thr Gly Asn Leu Lys Pro Asn Thr Asp Ser Asn Ala
                195                 200                 205

Leu Ile Asp Gln Gln Asn Thr Ser Ile Lys Val Tyr Lys Val Asp Asn
        210                 215                 220

Ala Ala Asp Leu Ser Glu Ser Tyr Phe Val Asn Pro Glu Asn Phe Glu
        225                 230                 235                 240

Asp Val Thr Asn Ser Val Asn Ile Thr Phe Pro Asn Pro Asn Gln Tyr
                        245                 250                 255

Lys Val Glu Phe Asn Thr Pro Asp Asp Gln Ile Thr Thr Pro Tyr Ile
                    260                 265                 270

Val Val Val Asn Gly His Ile Asp Pro Asn Ser Lys Gly Asp Leu Ala
                275                 280                 285

Leu Arg Ser Thr Leu Tyr Gly His Asn Ser Asn Ile Ile Trp Arg Ser
        290                 295                 300

Met Ser Trp Asp Asn Glu Val Ala Phe Asn Asn Gly Ser Gly Ser Gly
        305                 310                 315                 320

Asp Gly Ile Asp Lys Pro Val Val Pro Glu Gln Pro Asp Glu Pro Gly
                        325                 330                 335

Glu Ile Glu Pro Ile Pro Glu
                    340

<210> SEQ ID NO 12
<211> LENGTH: 331
<212> TYPE: PRT
<213> ORGANISM: Staphylococcus aureu

<400> SEQUENCE: 12

Gly Thr Asp Ile Thr Asn Gln Leu Thr Asn Val Thr Val Gly Ile Asp
        1               5                   10                  15

Ser Gly Thr Thr Val Tyr Pro His Gln Ala Gly Tyr Val Lys Leu Asn
                        20                  25                  30

Tyr Gly Phe Ser Val Pro Asn Ser Ala Val Lys Gly Asp Thr Phe Lys
                    35                  40                  45

Ile Thr Val Pro Lys Glu Leu Asn Leu Asn Gly Val Thr Ser Thr Ala
                50                  55                  60

Lys Val Pro Pro Ile Met Ala Gly Asp Gln Val Leu Ala Asn Gly Val
        65                  70                  75                  80

Ile Asp Ser Asp Gly Asn Val Ile Tyr Thr Phe Thr Asp Tyr Val Asn
                        85                  90                  95

Thr Lys Asp Asp Val Lys Ala Thr Leu Thr Met Pro Ala Tyr Ile Asp
```

```
            100                 105                 110
Pro Glu Asn Val Lys Lys Thr Gly Asn Val Thr Leu Ala Thr Gly Ile
        115                 120                 125
Gly Ser Thr Thr Ala Asn Lys Thr Val Leu Val Asp Tyr Glu Lys Tyr
    130                 135                 140
Gly Lys Phe Tyr Asn Leu Ser Ile Lys Gly Thr Ile Asp Gln Ile Asp
145                 150                 155                 160
Lys Thr Asn Asn Thr Tyr Arg Gln Thr Ile Tyr Val Asn Pro Ser Gly
                165                 170                 175
Asp Asn Val Ile Ala Pro Val Leu Thr Gly Asn Leu Lys Pro Asn Thr
            180                 185                 190
Asp Ser Asn Ala Leu Ile Asp Gln Gln Asn Thr Ser Ile Lys Val Tyr
        195                 200                 205
Lys Val Asp Asn Ala Ala Asp Leu Ser Glu Ser Tyr Phe Val Asn Pro
    210                 215                 220
Glu Asn Phe Glu Asp Val Thr Asn Ser Val Asn Ile Thr Phe Pro Asn
225                 230                 235                 240
Pro Asn Gln Tyr Lys Val Glu Phe Asn Thr Pro Asp Asp Gln Ile Thr
                245                 250                 255
Thr Pro Tyr Ile Val Val Asn Gly His Ile Asp Pro Asn Ser Lys
            260                 265                 270
Gly Asp Leu Ala Leu Arg Ser Thr Leu Tyr Gly His Asn Ser Asn Ile
        275                 280                 285
Ile Trp Arg Ser Met Ser Trp Asp Asn Glu Val Ala Phe Asn Asn Gly
    290                 295                 300
Ser Gly Ser Gly Asp Gly Ile Asp Lys Pro Val Val Pro Glu Gln Pro
305                 310                 315                 320
Asp Glu Pro Gly Glu Ile Glu Pro Ile Pro Glu
                325                 330

<210> SEQ ID NO 13
<211> LENGTH: 926
<212> TYPE: PRT
<213> ORGANISM: Staphylococcus aureus

<400> SEQUENCE: 13

Met Asn Met Lys Lys Lys Glu Lys His Ala Ile Arg Lys Lys Ser Ile
1               5                   10                  15
Gly Val Ala Ser Val Leu Val Gly Thr Leu Ile Gly Phe Gly Leu Leu
            20                  25                  30
Ser Ser Lys Glu Ala Asp Ala Ser Glu Asn Ser Val Thr Gln Ser Asp
        35                  40                  45
Ser Ala Ser Asn Glu Ser Lys Ser Asn Asp Ser Ser Val Ser Ala
    50                  55                  60
Ala Pro Lys Thr Asp Asp Thr Asn Val Ser Asp Thr Lys Thr Ser Ser
65                  70                  75                  80
Asn Thr Asn Asn Gly Glu Thr Ser Val Ala Gln Asn Pro Ala Gln Gln
                85                  90                  95
Glu Thr Thr Gln Ser Ser Thr Asn Ala Thr Thr Glu Glu Thr Pro
            100                 105                 110
Val Thr Gly Glu Ala Thr Thr Thr Thr Thr Asn Gln Ala Asn Thr Pro
        115                 120                 125
Ala Thr Thr Gln Ser Ser Asn Thr Asn Ala Glu Glu Leu Val Asn Gln
    130                 135                 140
Thr Ser Asn Glu Thr Thr Ser Asn Asp Thr Asn Thr Val Ser Ser Val
```

```
                145                 150                 155                 160
Asn Ser Pro Gln Asn Ser Thr Asn Ala Glu Asn Val Ser Thr Thr Gln
                165                 170                 175
Asp Thr Ser Thr Glu Ala Thr Pro Ser Asn Asn Glu Ser Ala Pro Gln
                180                 185                 190
Ser Thr Asp Ala Ser Asn Lys Asp Val Val Asn Gln Ala Val Asn Thr
                195                 200                 205
Ser Ala Pro Arg Met Arg Ala Phe Ser Leu Ala Ala Val Ala Ala Asp
            210                 215                 220
Ala Pro Val Ala Gly Thr Asp Ile Thr Asn Gln Leu Thr Asn Val Thr
225                 230                 235                 240
Val Gly Ile Asp Ser Gly Thr Thr Val Tyr Pro His Gln Ala Gly Tyr
                245                 250                 255
Val Lys Leu Asn Tyr Gly Phe Ser Val Pro Asn Ser Ala Val Lys Gly
            260                 265                 270
Asp Thr Phe Lys Ile Thr Val Pro Lys Glu Leu Asn Leu Asn Gly Val
            275                 280                 285
Thr Ser Thr Ala Lys Val Pro Pro Ile Met Ala Gly Asp Gln Val Leu
    290                 295                 300
Ala Asn Gly Val Ile Asp Ser Asp Gly Asn Val Ile Tyr Thr Phe Thr
305                 310                 315                 320
Asp Tyr Val Asn Thr Lys Asp Val Lys Ala Thr Leu Thr Met Pro
                325                 330                 335
Ala Tyr Ile Asp Pro Glu Asn Val Lys Lys Thr Gly Asn Val Thr Leu
            340                 345                 350
Ala Thr Gly Ile Gly Ser Thr Thr Ala Asn Lys Thr Val Leu Val Asp
            355                 360                 365
Tyr Glu Lys Tyr Gly Lys Phe Tyr Asn Leu Ser Ile Lys Gly Thr Ile
    370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Ile Ala Pro Val Leu Thr Gly Asn Leu
                405                 410                 415
Lys Pro Asn Thr Asp Ser Asn Ala Leu Ile Asp Gln Gln Asn Thr Ser
            420                 425                 430
Ile Lys Val Tyr Lys Val Asp Asn Ala Ala Asp Leu Ser Glu Ser Tyr
            435                 440                 445
Phe Val Asn Pro Glu Asn Phe Glu Asp Val Thr Asn Ser Val Asn Ile
    450                 455                 460
Thr Phe Pro Asn Pro Asn Gln Tyr Lys Val Glu Phe Asn Thr Pro Asp
465                 470                 475                 480
Asp Gln Ile Thr Thr Pro Tyr Ile Val Val Asn Gly His Ile Asp
                485                 490                 495
Pro Asn Ser Lys Gly Asp Leu Ala Leu Arg Ser Thr Leu Tyr Gly Asn
                500                 505                 510
Ser Asn Ile Ile Trp Arg Ser Met Ser Trp Asp Asn Glu Val Ala Phe
            515                 520                 525
Asn Asn Gly Ser Gly Ser Gly Asp Gly Ile Asp Lys Pro Val Val Pro
    530                 535                 540
Glu Gln Pro Asp Glu Pro Gly Glu Ile Glu Pro Ile Pro Glu Asp Ser
545                 550                 555                 560
Asp Ser Asp Pro Gly Ser Asp Ser Gly Ser Asp Ser Asn Ser Asp Ser
                565                 570                 575
```

```
Gly Ser Asp Ser Gly Ser Asp Ser Thr Ser Asp Ser Gly Ser Asp Ser
            580                 585                 590

Ala Ser Asp Ser Asp Ser Ala Ser Asp Ser Asp Ser Ala Ser Asp Ser
        595                 600                 605

Asp Ser Ala Ser Asp Ser Asp Ser Ala Ser Asp Ser Asp Ser Asp Asn
    610                 615                 620

Asp Ser Asp Ser Asp Ser Asp Ser Asp Ser Asp Ser Asp Ser Asp Ser
625                 630                 635                 640

Asp Ser Asp Ser Asp Ser Asp Ser Asp Ser Asp Ser Asp Ser Asp Ser
                645                 650                 655

Asp Ser Asp Ser Asp Ser Asp Ser Asp Ser Asp Ser Asp Ser Asp Ser
            660                 665                 670

Asp Ser Asp Ser Asp Ser Asp Ser Asp Ser Asp Ser Asp Ser Asp Ser
        675                 680                 685

Asp Ser Asp Ser Asp Ser Asp Ser Asp Ser Asp Ser Asp Ser Asp Ser
    690                 695                 700

Asp Ser Asp Ser Asp Ser Asp Ser Asp Ser Asp Ser Asp Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Ala Ser
        755                 760                 765

Asp Ser Asp Ser Asp Ser Asp Ser Asp Ser Asp Ser Asp Ser Asp Ser
    770                 775                 780

Asp Ser Asp Ser Asp Ser Asp Ser Asp Ser Asp Ser Asp Ser Asp Ser
785                 790                 795                 800

Asp Ser Asp Ser Asp Ser Glu Ser Asp Ser Asp Ser Asp Ser Asp Ser
                805                 810                 815

Asp Ser Asp Ser Asp Ser Asp Ser Asp Ser Asp Ser Asp Ser Ala Ser
            820                 825                 830

Asp Ser Asp Ser Gly Ser Asp Ser Asp Ser Ser Ser Asp Ser Asp Ser
        835                 840                 845

Glu Ser Asp Ser Asn Ser Asp Ser Glu Ser Val Ser Asn Asn Asn Val
    850                 855                 860

Val Pro Pro Asn Ser Pro Lys Asn Gly Thr Asn Ala Ser Asn Lys Asn
865                 870                 875                 880

Glu Ala Lys Asp Ser Lys Glu Pro Leu Pro Asp Thr Gly Ser Glu Asp
                885                 890                 895

Glu Ala Asn Thr Ser Leu Ile Trp Gly Leu Leu Ala Ser Ile Gly Ser
            900                 905                 910

Leu Leu Leu Phe Arg Arg Lys Lys Glu Asn Lys Asp Lys Lys
        915                 920                 925

<210> SEQ ID NO 14
<211> LENGTH: 520
<212> TYPE: PRT
<213> ORGANISM: Staphylococcus aureus

<400> SEQUENCE: 14

Met Ser Glu Asn Ser Val Thr Gln Ser Asp Ser Ala Ser Asn Glu Ser
1               5                   10                  15

Lys Ser Asn Asp Ser Ser Val Ser Ala Ala Pro Lys Thr Asp Asp
            20                  25                  30
```

-continued

```
Thr Asn Val Ser Asp Thr Lys Thr Ser Asn Thr Asn Asn Gly Glu
            35                  40                  45

Thr Ser Val Ala Gln Asn Pro Ala Gln Gln Glu Thr Thr Gln Ser Ser
50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Thr Gln Ser Ser
                85                  90                  95

Asn Thr Asn Ala Glu Glu Leu Val Asn Gln Thr Ser Asn Glu Thr Thr
                100                 105                 110

Ser Asn Asp Thr Asn Thr Val Ser Ser Val Asn Ser Pro Gln Asn Ser
            115                 120                 125

Thr Asn Ala Glu Asn Val Ser Thr Thr Gln Asp Thr Ser Thr Glu Ala
            130                 135                 140

Thr Pro Ser Asn Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
                165                 170                 175

Ala Phe Ser Leu Ala Ala Val Ala Ala Asp Ala Pro Val Ala Gly Thr
            180                 185                 190

Asp Ile Thr Asn Gln Leu Thr Asn Val Thr Val Gly Ile Asp Ser Gly
            195                 200                 205

Thr Thr Val Tyr Pro His Gln Ala Gly Tyr Val Lys Leu Asn Tyr Gly
            210                 215                 220

Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
                245                 250                 255

Pro Pro Ile Met Ala Gly Asp Gln Val Leu Ala Asn Gly Val Ile Asp
            260                 265                 270

Ser Asp Gly Asn Val Ile Tyr Thr Phe Thr Asp Tyr Val Asn Thr Lys
            275                 280                 285

Asp Asp Val Lys Ala Thr Leu Thr Met Pro Ala Tyr Ile Asp Pro Glu
290                 295                 300

Asn Val Lys Lys Thr Gly Asn Val Thr Leu Ala Thr Gly Ile Gly Ser
305                 310                 315                 320

Thr Thr Ala Asn Lys Thr Val Leu Val Asp Tyr Glu Lys Tyr Gly Lys
                325                 330                 335

Phe Tyr Asn Leu Ser Ile Lys Gly Thr Ile Asp Gln Ile Asp Lys Thr
            340                 345                 350

Asn Asn Thr Tyr Arg Gln Thr Ile Tyr Val Asn Pro Ser Gly Asp Asn
            355                 360                 365

Val Ile Ala Pro Val Leu Thr Gly Asn Leu Lys Pro Asn Thr Asp Ser
370                 375                 380

Asn Ala Leu Ile Asp Gln Gln Asn Thr Ser Ile Lys Val Tyr Lys Val
385                 390                 395                 400

Asp Asn Ala Ala Asp Leu Ser Glu Ser Tyr Phe Val Asn Pro Glu Asn
                405                 410                 415

Phe Glu Asp Val Thr Asn Ser Val Asn Ile Thr Phe Pro Asn Pro Asn
            420                 425                 430

Gln Tyr Lys Val Glu Phe Asn Thr Pro Asp Asp Gln Ile Thr Thr Pro
            435                 440                 445

Tyr Ile Val Val Val Asn Gly His Ile Asp Pro Asn Ser Lys Gly Asp
450                 455                 460
```

```
Leu Ala Leu Arg Ser Thr Leu Tyr Gly Asn Ser Asn Ile Ile Trp Arg
465                 470                 475                 480

Ser Met Ser Trp Asp Asn Glu Val Ala Phe Asn Asn Gly Ser Gly Ser
                485                 490                 495

Gly Asp Gly Ile Asp Lys Pro Val Val Pro Glu Gln Pro Asp Glu Pro
            500                 505                 510

Gly Glu Ile Glu Pro Ile Pro Glu
        515                 520

<210> SEQ ID NO 15
<211> LENGTH: 558
<212> TYPE: PRT
<213> ORGANISM: Staphylococcus aureus

<400> SEQUENCE: 15

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320
```

```
Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
                340                 345                 350

Ala Thr Gly Ile Gly Ser Thr Thr Ala Asn Lys Thr Val Leu Val Asp
                355                 360                 365

Tyr Glu Lys Tyr Gly Lys Phe Tyr Asn Leu Ser Ile Lys Gly Thr Ile
        370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
                420                 425                 430

Ile Lys Val Tyr Lys Val Asp Asn Ala Ala Asp Leu Ser Glu Ser Tyr
            435                 440                 445

Phe Val Asn Pro Glu Asn Phe Glu Asp Val Thr Asn Ser Val Asn Ile
            450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Asn
                500                 505                 510

Ser Asn Ile Ile Trp Arg Ser Met Ser Trp Asp Asn Glu Val Ala Phe
            515                 520                 525

Asn Asn Gly Ser Gly Ser Gly Asp Gly Ile Asp Lys Pro Val Val Pro
                530                 535                 540

Glu Gln Pro Asp Glu Pro Gly Glu Ile Glu Pro Ile Pro Glu
545                 550                 555

<210> SEQ ID NO 16
<211> LENGTH: 342
<212> TYPE: PRT
<213> ORGANISM: Staphylococcus aureus

<400> SEQUENCE: 16

Ser Leu Ala Ala Val Ala Ala Asp Ala Pro Val Ala Gly Thr Asp Ile
1               5                   10                  15

Thr Asn Gln Leu Thr Asn Val Thr Val Gly Ile Asp Ser Gly Thr Thr
                20                  25                  30

Val Tyr Pro His Gln Ala Gly Tyr Val Lys Leu Asn Tyr Gly Phe Ser
            35                  40                  45

Val Pro Asn Ser Ala Val Lys Gly Asp Thr Phe Lys Ile Thr Val Pro
        50                  55                  60

Lys Glu Leu Asn Leu Asn Gly Val Thr Ser Thr Ala Lys Val Pro Pro
65                  70                  75                  80

Ile Met Ala Gly Asp Gln Val Leu Ala Asn Gly Val Ile Asp Ser Asp
                85                  90                  95

Gly Asn Val Ile Tyr Thr Phe Thr Asp Tyr Val Asn Thr Lys Asp Asp
                100                 105                 110

Val Lys Ala Thr Leu Thr Met Pro Ala Tyr Ile Asp Pro Glu Asn Val
            115                 120                 125

Lys Lys Thr Gly Asn Val Thr Leu Ala Thr Gly Ile Gly Ser Thr Thr
        130                 135                 140
```

-continued

```
Ala Asn Lys Thr Val Leu Val Asp Tyr Glu Lys Tyr Gly Lys Phe Tyr
145                 150                 155                 160

Asn Leu Ser Ile Lys Gly Thr Ile Asp Gln Ile Asp Lys Thr Asn Asn
            165                 170                 175

Thr Tyr Arg Gln Thr Ile Tyr Val Asn Pro Ser Gly Asp Asn Val Ile
            180                 185                 190

Ala Pro Val Leu Thr Gly Asn Leu Lys Pro Asn Thr Asp Ser Asn Ala
            195                 200                 205

Leu Ile Asp Gln Gln Asn Thr Ser Ile Lys Val Tyr Lys Val Asp Asn
210                 215                 220

Ala Ala Asp Leu Ser Glu Ser Tyr Phe Val Asn Pro Glu Asn Phe Glu
225                 230                 235                 240

Asp Val Thr Asn Ser Val Asn Ile Thr Phe Pro Asn Pro Asn Gln Tyr
            245                 250                 255

Lys Val Glu Phe Asn Thr Pro Asp Asp Gln Ile Thr Thr Pro Tyr Ile
            260                 265                 270

Val Val Val Asn Gly His Ile Asp Pro Asn Ser Lys Gly Asp Leu Ala
            275                 280                 285

Leu Arg Ser Thr Leu Tyr Gly Asn Ser Asn Ile Ile Trp Arg Ser Met
290                 295                 300

Ser Trp Asp Asn Glu Val Ala Phe Asn Asn Gly Ser Gly Ser Gly Asp
305                 310                 315                 320

Gly Ile Asp Lys Pro Val Val Pro Glu Gln Pro Asp Glu Pro Gly Glu
            325                 330                 335

Ile Glu Pro Ile Pro Glu
            340

<210> SEQ ID NO 17
<211> LENGTH: 330
<212> TYPE: PRT
<213> ORGANISM: Staphylococcus aureus

<400> SEQUENCE: 17

Gly Thr Asp Ile Thr Asn Gln Leu Thr Asn Val Thr Val Gly Ile Asp
 1               5                  10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
            165                 170                 175
```

```
Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
            195                 200                 205

Lys Val Asp Asn Ala Ala Asp Leu Ser Glu Ser Tyr Phe Val Asn Pro
            210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
            245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Gly Asn Ser Asn Ile Ile
            275                 280                 285

Trp Arg Ser Met Ser Trp Asp Asn Glu Val Ala Phe Asn Asn Gly Ser
            290                 295                 300

Gly Ser Gly Asp Gly Ile Asp Lys Pro Val Val Pro Glu Gln Pro Asp
305                 310                 315                 320

Glu Pro Gly Glu Ile Glu Pro Ile Pro Glu
            325                 330

<210> SEQ ID NO 18
<211> LENGTH: 925
<212> TYPE: PRT
<213> ORGANISM: Staphylococcus aureus

<400> SEQUENCE: 18

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
            85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
            115                 120                 125

Ala Thr Thr Gln Ser Ser Asn Thr Asn Ala Glu Glu Leu Val Asn Gln
            130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
            165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
            210                 215                 220
```

```
Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
            245                 250                 255

Val Lys Leu Asn Tyr Gly Phe Ser Val Pro Asn Ser Ala Val Lys Gly
                260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
                340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
                420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Asn Ser
            500                 505                 510

Asn Ile Ile Trp Arg Ser Met Ser Trp Asp Asn Glu Val Ala Phe Asn
        515                 520                 525

Asn Gly Ser Gly Ser Gly Asp Gly Ile Asp Lys Pro Val Val Pro Glu
    530                 535                 540

Gln Pro Asp Glu Pro Gly Glu Ile Glu Pro Ile Pro Glu Asp Ser Asp
545                 550                 555                 560

Ser Asp Pro Gly Ser Asp Ser Gly Ser Asp Ser Asn Ser Asp Ser Gly
            565                 570                 575

Ser Asp Ser Gly Ser Asp Ser Thr Ser Asp Ser Gly Ser Asp Ser Ala
        580                 585                 590

Ser Asp Ser Asp Ser Ala Ser Asp Ser Ser Ala Ser Asp Ser Asp
    595                 600                 605

Ser Ala Ser Asp Ser Asp Ser Ala Ser Asp Ser Asp Ser Asp Asn Asp
    610                 615                 620

Ser Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
```

```
                645                 650                 655
Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp
            690                 695                 700

Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp
            740                 745                 750

Ser Asp Ser Asp Ser Asp Ser Asp Ser Asp Ser Ala Ser Asp
            755                 760                 765

Ser Asp Ser Asp Ser Asp Ser Asp Ser Asp Ser Asp Ser Asp
            770                 775                 780

Ser Asp Ser Asp Ser Asp Ser Asp Ser Asp Ser Asp Ser Asp
785                 790                 795                 800

Ser Asp Ser Asp Ser Glu Ser Asp Ser Asp Ser Asp Ser Asp
            805                 810                 815

Ser Asp Ser Asp Ser Asp Ser Asp Ser Asp Ser Ala Ser Asp
            820                 825                 830

Ser Asp Ser Gly Ser Asp Ser Asp Ser Ser Asp Ser Asp Ser Glu
            835                 840                 845

Ser Asp Ser Asn Ser Asp Ser Glu Ser Val Ser Asn Asn Val Val
850                 855                 860

Pro Pro Asn Ser Pro Lys Asn Gly Thr Asn Ala Ser Asn Lys Asn Glu
865                 870                 875                 880

Ala Lys Asp Ser Lys Glu Pro Leu Pro Asp Thr Gly Ser Glu Asp Glu
            885                 890                 895

Ala Asn Thr Ser Leu Ile Trp Gly Leu Leu Ala Ser Ile Gly Ser Leu
            900                 905                 910

Leu Leu Phe Arg Arg Lys Lys Glu Asn Lys Asp Lys Lys
            915                 920                 925

<210> SEQ ID NO 19
<211> LENGTH: 519
<212> TYPE: PRT
<213> ORGANISM: Staphylococcus aureus

<400> SEQUENCE: 19

Met Ser Glu Asn Ser Val Thr Gln Ser Asp Ser Ala Ser Asn Glu Ser
 1               5                  10                  15

Lys Ser Asn Asp Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
        35                  40                  45

Thr Ser Val Ala Gln Asn Pro Ala Gln Gln Glu Thr Thr Gln Ser Ser
    50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Thr Gln Ser Ser
            85                  90                  95

Asn Thr Asn Ala Glu Glu Leu Val Asn Gln Thr Ser Asn Glu Thr Thr
```

```
              100             105             110
Ser Asn Asp Thr Asn Thr Val Ser Ser Val Asn Ser Pro Gln Asn Ser
            115                 120             125
Thr Asn Ala Glu Asn Val Ser Thr Thr Gln Asp Thr Ser Thr Glu Ala
            130                 135             140
Thr Pro Ser Asn Asn Glu Ser Ala Pro Gln Ser Thr Asp Ala Ser Asn
145             150             155             160
Lys Asp Val Val Asn Gln Ala Val Asn Thr Ser Ala Pro Arg Met Arg
                165             170             175
Ala Phe Ser Leu Ala Ala Val Ala Ala Asp Ala Pro Val Ala Gly Thr
                180             185             190
Asp Ile Thr Asn Gln Leu Thr Asn Val Thr Val Gly Ile Asp Ser Gly
                195             200             205
Thr Thr Val Tyr Pro His Gln Ala Gly Tyr Val Lys Leu Asn Tyr Gly
            210             215             220
Phe Ser Val Pro Asn Ser Ala Val Lys Gly Asp Thr Phe Lys Ile Thr
225             230             235             240
Val Pro Lys Glu Leu Asn Leu Asn Gly Val Thr Ser Thr Ala Lys Val
                245             250             255
Pro Pro Ile Met Ala Gly Asp Gln Val Leu Ala Asn Gly Val Ile Asp
                260             265             270
Ser Asp Gly Asn Val Ile Tyr Thr Phe Thr Asp Tyr Val Asn Thr Lys
            275             280             285
Asp Asp Val Lys Ala Thr Leu Thr Met Pro Ala Tyr Ile Asp Pro Glu
            290             295             300
Asn Val Lys Lys Thr Gly Asn Val Thr Leu Ala Thr Gly Ile Gly Ser
305             310             315             320
Thr Thr Ala Asn Lys Thr Val Leu Val Asp Tyr Glu Lys Tyr Gly Lys
                325             330             335
Phe Tyr Asn Leu Ser Ile Lys Gly Thr Ile Asp Gln Ile Asp Lys Thr
                340             345             350
Asn Asn Thr Tyr Arg Gln Thr Ile Tyr Val Asn Pro Ser Gly Asp Asn
            355             360             365
Val Ile Ala Pro Val Leu Thr Gly Asn Leu Lys Pro Asn Thr Asp Ser
            370             375             380
Asn Ala Leu Ile Asp Gln Gln Asn Thr Ser Ile Lys Val Tyr Lys Val
385             390             395             400
Asp Asn Ala Ala Asp Leu Ser Glu Ser Tyr Phe Val Asn Pro Glu Asn
                405             410             415
Phe Glu Asp Val Thr Asn Ser Val Asn Ile Thr Phe Pro Asn Pro Asn
            420             425             430
Gln Tyr Lys Val Glu Phe Asn Thr Pro Asp Gln Ile Thr Thr Pro
            435             440             445
Tyr Ile Val Val Val Asn Gly His Ile Asp Pro Asn Ser Lys Gly Asp
            450             455             460
Leu Ala Leu Arg Ser Thr Leu Tyr Asn Ser Asn Ile Ile Trp Arg Ser
465             470             475             480
Met Ser Trp Asp Asn Glu Val Ala Phe Asn Asn Gly Ser Gly Ser Gly
                485             490             495
Asp Gly Ile Asp Lys Pro Val Val Pro Glu Gln Pro Asp Glu Pro Gly
                500             505             510
Glu Ile Glu Pro Ile Pro Glu
            515
```

<210> SEQ ID NO 20
<211> LENGTH: 557
<212> TYPE: PRT
<213> ORGANISM: Staphylococcus aureus

<400> SEQUENCE: 20

| | | | | | | | | | | | | | | | |
|---|---|---|---|---|---|---|---|---|---|---|---|---|---|---|---|
| Met | Asn | Met | Lys | Lys | Glu | Lys | His | Ala | Ile | Arg | Lys | Lys | Ser | Ile | |
| 1 | | | | 5 | | | | | 10 | | | | | 15 | |
| Gly | Val | Ala | Ser | Val | Leu | Val | Gly | Thr | Leu | Ile | Gly | Phe | Gly | Leu | Leu |
| | | | 20 | | | | | 25 | | | | | 30 | | |
| Ser | Ser | Lys | Glu | Ala | Asp | Ala | Ser | Glu | Asn | Ser | Val | Thr | Gln | Ser | Asp |
| | | 35 | | | | | 40 | | | | | 45 | | | |
| Ser | Ala | Ser | Asn | Glu | Ser | Lys | Ser | Asn | Asp | Ser | Ser | Val | Ser | Ala | |
| 50 | | | | | 55 | | | | | 60 | | | | | |
| Ala | Pro | Lys | Thr | Asp | Asp | Thr | Asn | Val | Ser | Asp | Thr | Lys | Thr | Ser | Ser |
| 65 | | | | 70 | | | | | 75 | | | | | 80 | |
| Asn | Thr | Asn | Asn | Gly | Glu | Thr | Ser | Val | Ala | Gln | Asn | Pro | Ala | Gln | Gln |
| | | | | 85 | | | | | 90 | | | | | 95 | |
| Glu | Thr | Thr | Gln | Ser | Ser | Ser | Thr | Asn | Ala | Thr | Thr | Glu | Glu | Thr | Pro |
| | | | 100 | | | | | 105 | | | | | 110 | | |
| Val | Thr | Gly | Glu | Ala | Thr | Thr | Thr | Thr | Asn | Gln | Ala | Asn | Thr | Pro | |
| | | 115 | | | | | 120 | | | | | 125 | | | |
| Ala | Thr | Thr | Gln | Ser | Ser | Asn | Thr | Asn | Ala | Glu | Glu | Leu | Val | Asn | Gln |
| | 130 | | | | | 135 | | | | | 140 | | | | |
| Thr | Ser | Asn | Glu | Thr | Thr | Ser | Asn | Asp | Thr | Asn | Thr | Val | Ser | Ser | Val |
| 145 | | | | | 150 | | | | | 155 | | | | | 160 |
| Asn | Ser | Pro | Gln | Asn | Ser | Thr | Asn | Ala | Glu | Asn | Val | Ser | Thr | Thr | Gln |
| | | | 165 | | | | | 170 | | | | | 175 | | |
| Asp | Thr | Ser | Thr | Glu | Ala | Thr | Pro | Ser | Asn | Asn | Glu | Ser | Ala | Pro | Gln |
| | | | 180 | | | | | 185 | | | | | 190 | | |
| Ser | Thr | Asp | Ala | Ser | Asn | Lys | Asp | Val | Val | Asn | Gln | Ala | Val | Asn | Thr |
| | | 195 | | | | | 200 | | | | | 205 | | | |
| Ser | Ala | Pro | Arg | Met | Arg | Ala | Phe | Ser | Leu | Ala | Ala | Val | Ala | Ala | Asp |
| | 210 | | | | | 215 | | | | | 220 | | | | |
| Ala | Pro | Val | Ala | Gly | Thr | Asp | Ile | Thr | Asn | Gln | Leu | Thr | Asn | Val | Thr |
| 225 | | | | | 230 | | | | | 235 | | | | | 240 |
| Val | Gly | Ile | Asp | Ser | Gly | Thr | Thr | Val | Tyr | Pro | His | Gln | Ala | Gly | Tyr |
| | | | | 245 | | | | | 250 | | | | | 255 | |
| Val | Lys | Leu | Asn | Tyr | Gly | Phe | Ser | Val | Pro | Asn | Ser | Ala | Val | Lys | Gly |
| | | | 260 | | | | | 265 | | | | | 270 | | |
| Asp | Thr | Phe | Lys | Ile | Thr | Val | Pro | Lys | Glu | Leu | Asn | Leu | Asn | Gly | Val |
| | | | 275 | | | | | 280 | | | | | 285 | | |
| Thr | Ser | Thr | Ala | Lys | Val | Pro | Pro | Ile | Met | Ala | Gly | Asp | Gln | Val | Leu |
| | 290 | | | | | 295 | | | | | 300 | | | | |
| Ala | Asn | Gly | Val | Ile | Asp | Ser | Asp | Gly | Asn | Val | Ile | Tyr | Thr | Phe | Thr |
| 305 | | | | | 310 | | | | | 315 | | | | | 320 |
| Asp | Tyr | Val | Asn | Thr | Lys | Asp | Asp | Val | Lys | Ala | Thr | Leu | Thr | Met | Pro |
| | | | | 325 | | | | | 330 | | | | | 335 | |
| Ala | Tyr | Ile | Asp | Pro | Glu | Asn | Val | Lys | Lys | Thr | Gly | Asn | Val | Thr | Leu |
| | | | 340 | | | | | 345 | | | | | 350 | | |
| Ala | Thr | Gly | Ile | Gly | Ser | Thr | Thr | Ala | Asn | Lys | Thr | Val | Leu | Val | Asp |
| | | 355 | | | | | 360 | | | | | 365 | | | |
| Tyr | Glu | Lys | Tyr | Gly | Lys | Phe | Tyr | Asn | Leu | Ser | Ile | Lys | Gly | Thr | Ile |
| | 370 | | | | | 375 | | | | | 380 | | | | |

```
Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
            405                 410                 415

Lys Pro Asn Thr Asp Ser Asn Ala Leu Ile Asp Gln Gln Asn Thr Ser
        420                 425                 430

Ile Lys Val Tyr Lys Val Asp Asn Ala Ala Asp Leu Ser Glu Ser Tyr
    435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Asn Ser
            500                 505                 510

Asn Ile Ile Trp Arg Ser Met Ser Trp Asp Asn Glu Val Ala Phe Asn
            515                 520                 525

Asn Gly Ser Gly Ser Gly Asp Gly Ile Asp Lys Pro Val Val Pro Glu
        530                 535                 540

Gln Pro Asp Glu Pro Gly Glu Ile Glu Pro Ile Pro Glu
545                 550                 555

<210> SEQ ID NO 21
<211> LENGTH: 341
<212> TYPE: PRT
<213> ORGANISM: Staphylococcus aureus

<400> SEQUENCE: 21

Ser Leu Ala Ala Val Ala Ala Asp Ala Pro Val Ala Gly Thr Asp Ile
1               5                   10                  15

Thr Asn Gln Leu Thr Asn Val Thr Val Gly Ile Asp Ser Gly Thr Thr
            20                  25                  30

Val Tyr Pro His Gln Ala Gly Tyr Val Lys Leu Asn Tyr Gly Phe Ser
        35                  40                  45

Val Pro Asn Ser Ala Val Lys Gly Asp Thr Phe Lys Ile Thr Val Pro
    50                  55                  60

Lys Glu Leu Asn Leu Asn Gly Val Thr Ser Thr Ala Lys Val Pro Pro
65                  70                  75                  80

Ile Met Ala Gly Asp Gln Val Leu Ala Asn Gly Val Ile Asp Ser Asp
                85                  90                  95

Gly Asn Val Ile Tyr Thr Phe Thr Asp Tyr Val Asn Thr Lys Asp Asp
            100                 105                 110

Val Lys Ala Thr Leu Thr Met Pro Ala Tyr Ile Asp Pro Glu Asn Val
        115                 120                 125

Lys Lys Thr Gly Asn Val Thr Leu Ala Thr Gly Ile Gly Ser Thr Thr
    130                 135                 140

Ala Asn Lys Thr Val Leu Val Asp Tyr Glu Lys Tyr Gly Lys Phe Tyr
145                 150                 155                 160

Asn Leu Ser Ile Lys Gly Thr Ile Asp Gln Ile Asp Lys Thr Asn Asn
                165                 170                 175

Thr Tyr Arg Gln Thr Ile Tyr Val Asn Pro Ser Gly Asp Asn Val Ile
            180                 185                 190

Ala Pro Val Leu Thr Gly Asn Leu Lys Pro Asn Thr Asp Ser Asn Ala
        195                 200                 205
```

```
Leu Ile Asp Gln Gln Asn Thr Ser Ile Lys Val Tyr Lys Val Asp Asn
    210                 215                 220

Ala Ala Asp Leu Ser Glu Ser Tyr Phe Val Asn Pro Glu Asn Phe Glu
225                 230                 235                 240

Asp Val Thr Asn Ser Val Asn Ile Thr Phe Pro Asn Pro Asn Gln Tyr
                245                 250                 255

Lys Val Glu Phe Asn Thr Pro Asp Asp Gln Ile Thr Thr Pro Tyr Ile
                260                 265                 270

Val Val Val Asn Gly His Ile Asp Pro Asn Ser Lys Gly Asp Leu Ala
            275                 280                 285

Leu Arg Ser Thr Leu Tyr Asn Ser Asn Ile Ile Trp Arg Ser Met Ser
    290                 295                 300

Trp Asp Asn Glu Val Ala Phe Asn Asn Gly Ser Gly Ser Gly Asp Gly
305                 310                 315                 320

Ile Asp Lys Pro Val Val Pro Glu Gln Pro Asp Glu Pro Gly Glu Ile
                325                 330                 335

Glu Pro Ile Pro Glu
            340

<210> SEQ ID NO 22
<211> LENGTH: 329
<212> TYPE: PRT
<213> ORGANISM: Staphylococcus aureus

<400> SEQUENCE: 22

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
                20                  25                  30

Tyr Gly Phe Ser Val Pro Asn Ser Ala Val Lys Gly Asp Thr Phe Lys
            35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
                100                 105                 110

Pro Glu Asn Val Lys Lys Thr Gly Asn Val Thr Leu Ala Thr Gly Ile
            115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240
```

```
Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Asn Ser Asn Ile Ile Trp
            275                 280                 285

Arg Ser Met Ser Trp Asp Asn Glu Val Ala Phe Asn Asn Gly Ser Gly
            290                 295                 300

Ser Gly Asp Gly Ile Asp Lys Pro Val Val Pro Glu Gln Pro Asp Glu
305                 310                 315                 320

Pro Gly Glu Ile Glu Pro Ile Pro Glu
                325

<210> SEQ ID NO 23
<211> LENGTH: 924
<212> TYPE: PRT
<213> ORGANISM: Staphylococcus aureus

<400> SEQUENCE: 23

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285
```

```
Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Ser Asn
                500                 505                 510

Ile Ile Trp Arg Ser Met Ser Trp Asp Asn Glu Val Ala Phe Asn Asn
            515                 520                 525

Gly Ser Gly Ser Gly Asp Gly Ile Asp Lys Pro Val Val Pro Glu Gln
            530                 535                 540

Pro Asp Glu Pro Gly Glu Ile Glu Pro Ile Pro Glu Asp Ser Asp Ser
545                 550                 555                 560

Asp Pro Gly Ser Asp Ser Gly Ser Asp Ser Asn Ser Asp Ser Gly Ser
                565                 570                 575

Asp Ser Gly Ser Asp Ser Thr Ser Asp Ser Gly Ser Asp Ser Ala Ser
            580                 585                 590

Asp Ser Asp Ser Ala Ser Asp Ser Asp Ser Ala Ser Asp Ser Asp Ser
        595                 600                 605

Ala Ser Asp Ser Asp Ser Ala Ser Asp Ser Asp Ser Asp Ser Asn Asp Ser
610                 615                 620

Asp Ser Asp Ser Asp Ser Asp Ser Asp Ser Asp Ser Asp Ser Asp Ser
625                 630                 635                 640

Asp Ser Asp Ser Asp Ser Asp Ser Asp Ser Asp Ser Asp Ser Asp Ser
                645                 650                 655

Asp Ser Asp Ser Asp Ser Asp Ser Asp Ser Asp Ser Asp Ser Asp Ser
        660                 665                 670

Asp Ser Asp Ser Asp Ser Asp Ser Asp Ser Asp Ser Asp Ser Asp Ser
        675                 680                 685

Asp Ser Asp Ser Asp Ser Asp Ser Asp Ser Asp Ser Asp Ser Asp Ser
        690                 695                 700

Asp Ser Asp Ser Asp Ser Asp Ser Asp Ser Asp Ser Asp Ser Asp Ser
705                 710                 715                 720
```

Asp Ser Asp Ser Asp Ser Asp Ser Asp Ser Asp Ser
            725                 730                 735

Asp Ser Asp Ser Asp Ser Asp Ser Asp Ser Asp Ser
            740                 745                 750

Asp Ser Asp Ser Asp Ser Asp Ser Asp Ser Ala Ser Asp Ser
            755                 760                 765

Asp Ser Asp Ser Asp Ser Asp Ser Asp Ser Asp Ser
            770                 775                 780

Asp Ser Asp Ser Asp Ser Asp Ser Asp Ser Asp Ser
785                 790                 795                 800

Asp Ser Asp Ser Glu Ser Asp Ser Asp Ser Asp Ser
            805                 810                 815

Asp Ser Asp Ser Asp Ser Asp Ser Asp Ser Ala Ser Asp Ser
            820                 825                 830

Asp Ser Gly Ser Asp Ser Asp Ser Ser Ser Asp Ser Asp Ser Glu Ser
            835                 840                 845

Asp Ser Asn Ser Asp Ser Glu Ser Val Ser Asn Asn Val Val Pro
            850                 855                 860

Pro Asn Ser Pro Lys Asn Gly Thr Asn Ala Ser Asn Lys Asn Glu Ala
865                 870                 875                 880

Lys Asp Ser Lys Glu Pro Leu Pro Asp Thr Gly Ser Glu Asp Glu Ala
            885                 890                 895

Asn Thr Ser Leu Ile Trp Gly Leu Leu Ala Ser Ile Gly Ser Leu Leu
            900                 905                 910

Leu Phe Arg Arg Lys Lys Glu Asn Lys Asp Lys Lys
            915                 920

<210> SEQ ID NO 24
<211> LENGTH: 518
<212> TYPE: PRT
<213> ORGANISM: Staphylococcus aureus

<400> SEQUENCE: 24

Met Ser Glu Asn Ser Val Thr Gln Ser Asp Ser Ala Ser Asn Glu Ser
1               5                   10                  15

Lys Ser Asn Asp Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
            35                  40                  45

Thr Ser Val Ala Gln Asn Pro Ala Gln Gln Thr Thr Gln Ser Ser
            50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Gln Ser Ser
            85                  90                  95

Asn Thr Asn Ala Glu Glu Leu Val Asn Gln Thr Ser Asn Glu Thr Thr
            100                 105                 110

Ser Asn Asp Thr Asn Thr Val Ser Ser Val Asn Ser Pro Gln Asn Ser
            115                 120                 125

Thr Asn Ala Glu Asn Val Ser Thr Thr Gln Asp Thr Ser Thr Glu Ala
            130                 135                 140

Thr Pro Ser Asn Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
            165                 170                 175

Ala Phe Ser Leu Ala Ala Val Ala Ala Asp Ala Pro Val Ala Gly Thr
                180                 185                 190

Asp Ile Thr Asn Gln Leu Thr Asn Val Thr Val Gly Ile Asp Ser Gly
            195                 200                 205

Thr Thr Val Tyr Pro His Gln Ala Gly Tyr Val Lys Leu Asn Tyr Gly
        210                 215                 220

Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
                245                 250                 255

Pro Pro Ile Met Ala Gly Asp Gln Val Leu Ala Asn Gly Val Ile Asp
            260                 265                 270

Ser Asp Gly Asn Val Ile Tyr Thr Phe Thr Asp Tyr Val Asn Thr Lys
        275                 280                 285

Asp Asp Val Lys Ala Thr Leu Thr Met Pro Ala Tyr Ile Asp Pro Glu
290                 295                 300

Asn Val Lys Lys Thr Gly Asn Val Thr Leu Ala Thr Gly Ile Gly Ser
                305                 310                 315                 320

Thr Thr Ala Asn Lys Thr Val Leu Val Asp Tyr Glu Lys Tyr Gly Lys
            325                 330                 335

Phe Tyr Asn Leu Ser Ile Lys Gly Thr Ile Asp Gln Ile Asp Lys Thr
        340                 345                 350

Asn Asn Thr Tyr Arg Gln Thr Ile Tyr Val Asn Pro Ser Gly Asp Asn
        355                 360                 365

Val Ile Ala Pro Val Leu Thr Gly Asn Leu Lys Pro Asn Thr Asp Ser
370                 375                 380

Asn Ala Leu Ile Asp Gln Gln Asn Thr Ser Ile Lys Val Tyr Lys Val
385                 390                 395                 400

Asp Asn Ala Ala Asp Leu Ser Glu Ser Tyr Phe Val Asn Pro Glu Asn
                405                 410                 415

Phe Glu Asp Val Thr Asn Ser Val Asn Ile Thr Phe Pro Asn Pro Asn
            420                 425                 430

Gln Tyr Lys Val Glu Phe Asn Thr Pro Asp Asp Gln Ile Thr Thr Pro
        435                 440                 445

Tyr Ile Val Val Asn Gly His Ile Asp Pro Asn Ser Lys Gly Asp
        450                 455                 460

Leu Ala Leu Arg Ser Thr Leu Tyr Ser Asn Ile Ile Trp Arg Ser Met
465                 470                 475                 480

Ser Trp Asp Asn Glu Val Ala Phe Asn Asn Gly Ser Gly Ser Gly Asp
                485                 490                 495

Gly Ile Asp Lys Pro Val Val Pro Glu Gln Pro Asp Glu Pro Gly Glu
            500                 505                 510

Ile Glu Pro Ile Pro Glu
        515

<210> SEQ ID NO 25
<211> LENGTH: 556
<212> TYPE: PRT
<213> ORGANISM: Staphylococcus aureus

<400> SEQUENCE: 25

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

```
Ser Ser Lys Glu Ala Asp Ala Ser Glu Asn Ser Val Thr Gln Ser Asp
         35                  40                  45

Ser Ala Ser Asn Glu Ser Lys Ser Asn Asp Ser Ser Val Ser Ala
 50                  55                  60

Ala Pro Lys Thr Asp Thr Asn Val Ser Asp Lys Thr Ser Ser
 65              70                  75                  80

Asn Thr Asn Asn Gly Glu Thr Ser Val Ala Gln Asn Pro Ala Gln Gln
             85                  90                  95

Glu Thr Thr Gln Ser Ser Thr Asn Ala Thr Thr Glu Glu Thr Pro
             100                 105                 110

Val Thr Gly Glu Ala Thr Thr Thr Thr Asn Gln Ala Asn Thr Pro
             115                 120                 125

Ala Thr Thr Gln Ser Ser Asn Thr Asn Ala Glu Leu Val Asn Gln
             130                 135             140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                 165                 170                 175

Asp Thr Ser Thr Glu Ala Thr Pro Ser Asn Asn Glu Ser Ala Pro Gln
                 180                 185                 190

Ser Thr Asp Ala Ser Asn Lys Asp Val Val Asn Gln Ala Val Asn Thr
                 195                 200                 205

Ser Ala Pro Arg Met Arg Ala Phe Ser Leu Ala Ala Val Ala Ala Asp
                 210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                 245                 250                 255

Val Lys Leu Asn Tyr Gly Phe Ser Val Pro Asn Ser Ala Val Lys Gly
                 260                 265                 270

Asp Thr Phe Lys Ile Thr Val Pro Lys Glu Leu Asn Leu Asn Gly Val
                 275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                 325                 330                 335

Ala Tyr Ile Asp Pro Glu Asn Val Lys Lys Thr Gly Asn Val Thr Leu
                 340                 345                 350

Ala Thr Gly Ile Gly Ser Thr Thr Ala Asn Lys Thr Val Leu Val Asp
                 355                 360                 365

Tyr Glu Lys Tyr Gly Lys Phe Tyr Asn Leu Ser Ile Lys Gly Thr Ile
         370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                 405                 410                 415

Lys Pro Asn Thr Asp Ser Asn Ala Leu Ile Asp Gln Gln Asn Thr Ser
                 420                 425                 430

Ile Lys Val Tyr Lys Val Asp Asn Ala Ala Asp Leu Ser Glu Ser Tyr
                 435                 440                 445

Phe Val Asn Pro Glu Asn Phe Glu Asp Val Thr Asn Ser Val Asn Ile
```

```
                 450                 455                 460
Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Ser Asn
                500                 505                 510

Ile Ile Trp Arg Ser Met Ser Trp Asp Asn Glu Val Ala Phe Asn Asn
                515                 520                 525

Gly Ser Gly Ser Gly Asp Gly Ile Asp Lys Pro Val Val Pro Glu Gln
530                 535                 540

Pro Asp Glu Pro Gly Glu Ile Glu Pro Ile Pro Glu
545                 550                 555

<210> SEQ ID NO 26
<211> LENGTH: 340
<212> TYPE: PRT
<213> ORGANISM: Staphylococcus aureus

<400> SEQUENCE: 26

Ser Leu Ala Ala Val Ala Ala Asp Ala Pro Val Ala Gly Thr Asp Ile
1               5                   10                  15

Thr Asn Gln Leu Thr Asn Val Thr Val Gly Ile Asp Ser Gly Thr Thr
                20                  25                  30

Val Tyr Pro His Gln Ala Gly Tyr Val Lys Leu Asn Tyr Gly Phe Ser
            35                  40                  45

Val Pro Asn Ser Ala Val Lys Gly Asp Thr Phe Lys Ile Thr Val Pro
50                  55                  60

Lys Glu Leu Asn Leu Asn Gly Val Thr Ser Thr Ala Lys Val Pro Pro
65                  70                  75                  80

Ile Met Ala Gly Asp Gln Val Leu Ala Asn Gly Val Ile Asp Ser Asp
                85                  90                  95

Gly Asn Val Ile Tyr Thr Phe Thr Asp Tyr Val Asn Thr Lys Asp Asp
                100                 105                 110

Val Lys Ala Thr Leu Thr Met Pro Ala Tyr Ile Asp Pro Glu Asn Val
            115                 120                 125

Lys Lys Thr Gly Asn Val Thr Leu Ala Thr Gly Ile Gly Ser Thr Thr
130                 135                 140

Ala Asn Lys Thr Val Leu Val Asp Tyr Glu Lys Tyr Gly Lys Phe Tyr
145                 150                 155                 160

Asn Leu Ser Ile Lys Gly Thr Ile Asp Gln Ile Asp Lys Thr Asn Asn
                165                 170                 175

Thr Tyr Arg Gln Thr Ile Tyr Val Asn Pro Ser Gly Asp Asn Val Ile
            180                 185                 190

Ala Pro Val Leu Thr Gly Asn Leu Lys Pro Asn Thr Asp Ser Asn Ala
            195                 200                 205

Leu Ile Asp Gln Gln Asn Thr Ser Ile Lys Val Tyr Lys Val Asp Asn
210                 215                 220

Ala Ala Asp Leu Ser Glu Ser Tyr Phe Val Asn Pro Glu Asn Phe Glu
225                 230                 235                 240

Asp Val Thr Asn Ser Val Asn Ile Thr Phe Pro Asn Pro Asn Gln Tyr
                245                 250                 255

Lys Val Glu Phe Asn Thr Pro Asp Gln Ile Thr Thr Pro Tyr Ile
                260                 265                 270

Val Val Val Asn Gly His Ile Asp Pro Asn Ser Lys Gly Asp Leu Ala
```

```
                275                 280                 285
Leu Arg Ser Thr Leu Tyr Ser Asn Ile Ile Trp Arg Ser Met Ser Trp
290                 295                 300

Asp Asn Glu Val Ala Phe Asn Asn Gly Ser Gly Ser Gly Asp Gly Ile
305                 310                 315                 320

Asp Lys Pro Val Val Pro Glu Gln Pro Asp Glu Pro Gly Glu Ile Glu
                325                 330                 335

Pro Ile Pro Glu
            340

<210> SEQ ID NO 27
<211> LENGTH: 328
<212> TYPE: PRT
<213> ORGANISM: Staphylococcus aureus

<400> SEQUENCE: 27

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
                 20                  25                  30

Tyr Gly Phe Ser Val Pro Asn Ser Ala Val Lys Gly Asp Thr Phe Lys
             35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

Ile Asp Ser Asp Gly Asn Val Ile Tyr Thr Phe Thr Asp Tyr Val Asn
                 85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Ser Asn Ile Ile Trp Arg
        275                 280                 285

Ser Met Ser Trp Asp Asn Glu Val Ala Phe Asn Asn Gly Ser Gly Ser
    290                 295                 300

Gly Asp Gly Ile Asp Lys Pro Val Val Pro Glu Gln Pro Asp Glu Pro
```

```
                305                 310                 315                 320
Gly Glu Ile Glu Pro Ile Pro Glu
                325

<210> SEQ ID NO 28
<211> LENGTH: 329
<212> TYPE: PRT
<213> ORGANISM: Staphylococcus aureus

<400> SEQUENCE: 28

Gly Thr Asp Ile Thr Asn Gln Leu Thr Asn Val Thr Gly Ile Asp
  1               5                  10                  15

Ser Gly Thr Thr Val Tyr Pro His Gln Ala Gly Tyr Val Lys Leu Asn
                 20                  25                  30

Tyr Gly Phe Ser Val Pro Asn Ser Ala Val Lys Gly Asp Thr Phe Lys
             35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

Ile Asp Ser Asp Gly Asn Val Ile Tyr Thr Phe Thr Asp Tyr Val Asn
                 85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Gly Ser Asn Ile Ile Trp
        275                 280                 285

Arg Ser Met Ser Trp Asp Asn Glu Val Ala Phe Asn Asn Gly Ser Gly
    290                 295                 300

Ser Gly Asp Gly Ile Asp Lys Pro Val Val Pro Glu Gln Pro Asp Glu
305                 310                 315                 320

Pro Gly Glu Ile Glu Pro Ile Pro Glu
                325

<210> SEQ ID NO 29
<211> LENGTH: 327
<212> TYPE: PRT
```

<213> ORGANISM: Staphylococcus aureus

<400> SEQUENCE: 29

```
Gly Thr Asp Ile Thr Asn Gln Leu Thr Asn Val Thr Gly Ile Asp
1               5                   10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Asn Ile Ile Trp Arg Ser
        275                 280                 285

Met Ser Trp Asp Asn Glu Val Ala Phe Asn Asn Gly Ser Gly Ser Gly
    290                 295                 300

Asp Gly Ile Asp Lys Pro Val Val Pro Glu Gln Pro Asp Glu Pro Gly
305                 310                 315                 320

Glu Ile Glu Pro Ile Pro Glu
                325
```

<210> SEQ ID NO 30
<211> LENGTH: 327
<212> TYPE: PRT
<213> ORGANISM: Staphylococcus aureus

<400> SEQUENCE: 30

```
Gly Thr Asp Ile Thr Asn Gln Leu Thr Asn Val Thr Gly Ile Asp
1               5                   10                  15

Ser Gly Thr Thr Val Tyr Pro His Gln Ala Gly Tyr Val Lys Leu Asn
            20                  25                  30
```

Tyr Gly Phe Ser Val Pro Asn Ser Ala Val Lys Gly Asp Thr Phe Lys
                35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
                100                 105                 110

Pro Glu Asn Val Lys Lys Thr Gly Asn Val Thr Leu Ala Thr Gly Ile
                115                 120                 125

Gly Ser Thr Thr Ala Asn Lys Thr Val Leu Val Asp Tyr Glu Lys Tyr
                130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
                180                 185                 190

Asp Ser Asn Ala Leu Ile Asp Gln Gln Asn Thr Ser Ile Lys Val Tyr
                195                 200                 205

Lys Val Asp Asn Ala Ala Asp Leu Ser Glu Ser Tyr Phe Val Asn Pro
                210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
                260                 265                 270

Gly Asp Leu Ala Leu Arg Ser Thr Leu Tyr Gly Ile Ile Trp Arg Ser
                275                 280                 285

Met Ser Trp Asp Asn Glu Val Ala Phe Asn Asn Gly Ser Gly Ser Gly
                290                 295                 300

Asp Gly Ile Asp Lys Pro Val Val Pro Glu Gln Pro Asp Glu Pro Gly
305                 310                 315                 320

Glu Ile Glu Pro Ile Pro Glu
                325

<210> SEQ ID NO 31
<211> LENGTH: 327
<212> TYPE: PRT
<213> ORGANISM: Staphylococcus aureus

<400> SEQUENCE: 31

Gly Thr Asp Ile Thr Asn Gln Leu Thr Asn Val Thr Val Gly Ile Asp
 1               5                  10                  15

Ser Gly Thr Thr Val Tyr Pro His Gln Ala Gly Tyr Val Lys Leu Asn
                20                  25                  30

Tyr Gly Phe Ser Val Pro Asn Ser Ala Val Lys Gly Asp Thr Phe Lys
                35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

```
Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Ser Asn Ile Ile Trp Arg Ser
        275                 280                 285

Met Ser Trp Asp Asn Glu Val Ala Phe Asn Asn Gly Ser Gly Ser Gly
290                 295                 300

Asp Gly Ile Asp Lys Pro Val Val Pro Glu Gln Pro Asp Gly Pro Gly
305                 310                 315                 320

Glu Ile Glu Pro Ile Pro Glu
                325

<210> SEQ ID NO 32
<211> LENGTH: 327
<212> TYPE: PRT
<213> ORGANISM: Staphylococcus aureus

<400> SEQUENCE: 32

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
                20                  25                  30

Tyr Gly Phe Ser Val Pro Asn Ser Ala Val Lys Gly Asp Thr Phe Lys
            35                  40                  45

Ile Thr Val Pro Lys Glu Leu Asn Leu Asn Gly Val Thr Ser Thr Ala
        50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125
```

-continued

```
Gly Ser Thr Thr Ala Asn Lys Thr Val Leu Val Asp Tyr Glu Lys Tyr
            130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Asn Ser Asn Ile Ile Trp Arg Ser
        275                 280                 285

Met Ser Trp Asp Asn Glu Val Ala Phe Asn Asn Gly Ser Gly Ser Gly
290                 295                 300

Asp Gly Ile Asp Lys Pro Val Val Pro Glu Gln Pro Asp Glu Pro Gly
305                 310                 315                 320

Glu Ile Glu Pro Ile Pro Glu
                325

<210> SEQ ID NO 33
<211> LENGTH: 326
<212> TYPE: PRT
<213> ORGANISM: Staphylococcus aureus

<400> SEQUENCE: 33

Gly Thr Asp Ile Thr Asn Gln Leu Thr Asn Val Thr Val Gly Ile Asp
 1               5                  10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175
```

```
Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
            195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
            245                 250                 255

Thr Pro Tyr Ile Val Val Asn Gly His Ile Asp Pro Asn Ser Lys
            260                 265                 270

Gly Asp Leu Ala Leu Arg Ser Asn Ser Asn Ile Ile Trp Arg Ser Met
            275                 280                 285

Ser Trp Asp Asn Glu Val Ala Phe Asn Asn Gly Ser Gly Ser Gly Asp
            290                 295                 300

Gly Ile Asp Lys Pro Val Val Pro Glu Gln Pro Asp Glu Pro Gly Glu
305                 310                 315                 320

Ile Glu Pro Ile Pro Glu
            325

<210> SEQ ID NO 34
<211> LENGTH: 326
<212> TYPE: PRT
<213> ORGANISM: Staphylococcus aureus

<400> SEQUENCE: 34

Gly Thr Asp Ile Thr Asn Gln Leu Thr Asn Val Thr Val Gly Ile Asp
 1               5                   10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
            85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
            115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
            165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
            195                 200                 205

Lys Val Asp Asn Ala Ala Asp Leu Ser Glu Ser Tyr Phe Val Asn Pro
210                 215                 220
```

```
Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
            245                 250                 255

Thr Pro Tyr Ile Val Val Asn Gly His Ile Asp Pro Asn Ser Lys
        260                 265                 270

Gly Asp Leu Ala Leu Arg Ser Thr Ser Asn Ile Ile Trp Arg Ser Met
    275                 280                 285

Ser Trp Asp Asn Glu Val Ala Phe Asn Gly Ser Gly Ser Gly Asp
290                 295                 300

Gly Ile Asp Lys Pro Val Val Pro Glu Gln Pro Asp Glu Pro Gly Glu
305                 310                 315                 320

Ile Glu Pro Ile Pro Glu
                325

<210> SEQ ID NO 35
<211> LENGTH: 326
<212> TYPE: PRT
<213> ORGANISM: Staphylococcus aureus

<400> SEQUENCE: 35

Gly Thr Asp Ile Thr Asn Gln Leu Thr Asn Val Thr Val Gly Ile Asp
1               5                   10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
            245                 250                 255

Thr Pro Tyr Ile Val Val Asn Gly His Ile Asp Pro Asn Ser Lys
        260                 265                 270
```

```
Gly Asp Leu Ala Leu Arg Ser Thr Leu Tyr Ile Ile Trp Arg Ser Met
            275                 280                 285

Ser Trp Asp Asn Glu Val Ala Phe Asn Asn Gly Ser Gly Ser Gly Asp
        290                 295                 300

Gly Ile Asp Lys Pro Val Val Pro Glu Gln Pro Asp Glu Pro Gly Glu
305                 310                 315                 320

Ile Glu Pro Ile Pro Glu
                325

<210> SEQ ID NO 36
<211> LENGTH: 325
<212> TYPE: PRT
<213> ORGANISM: Staphylococcus aureus

<400> SEQUENCE: 36

Gly Thr Asp Ile Thr Asn Gln Leu Thr Asn Val Thr Gly Ile Asp
1               5                   10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Gly Trp Arg Ser Met Ser
        275                 280                 285

Trp Asp Asn Glu Val Ala Phe Asn Asn Gly Ser Gly Ser Gly Asp Gly
    290                 295                 300

Ile Asp Lys Pro Val Val Pro Glu Gln Pro Asp Glu Pro Gly Glu Ile
305                 310                 315                 320
```

```
Glu Pro Ile Pro Glu
            325

<210> SEQ ID NO 37
<211> LENGTH: 325
<212> TYPE: PRT
<213> ORGANISM: Staphylococcus aureus

<400> SEQUENCE: 37

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
                 20                  25                  30

Tyr Gly Phe Ser Val Pro Asn Ser Ala Val Lys Gly Asp Thr Phe Lys
             35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

Ile Asp Ser Asp Gly Asn Val Ile Tyr Thr Phe Thr Asp Tyr Val Asn
                 85                  90                  95

Thr Lys Asp Asp Val Lys Ala Thr Leu Thr Met Pro Ala Tyr Ile Asp
                100                 105                 110

Pro Glu Asn Val Lys Lys Thr Gly Asn Val Thr Leu Ala Thr Gly Ile
            115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Tyr Ile Trp Arg Ser Met Ser
        275                 280                 285

Trp Asp Asn Glu Val Ala Phe Asn Asn Gly Ser Gly Ser Gly Asp Gly
290                 295                 300

Ile Asp Lys Pro Val Val Pro Glu Gln Pro Asp Glu Pro Gly Glu Ile
305                 310                 315                 320

Glu Pro Ile Pro Glu
            325

<210> SEQ ID NO 38
<211> LENGTH: 325
<212> TYPE: PRT
<213> ORGANISM: Staphylococcus aureus
```

```
<400> SEQUENCE: 38

Gly Thr Asp Ile Thr Asn Gln Leu Thr Asn Val Thr Val Gly Ile Asp
1               5                   10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Thr Leu Ile Ile Trp Arg Ser Met Ser
        275                 280                 285

Trp Asp Asn Glu Val Ala Phe Asn Asn Gly Ser Gly Ser Gly Asp Gly
290                 295                 300

Ile Asp Lys Pro Val Val Pro Glu Gln Pro Asp Glu Pro Gly Glu Ile
305                 310                 315                 320

Glu Pro Ile Pro Glu
                325

<210> SEQ ID NO 39
<211> LENGTH: 325
<212> TYPE: PRT
<213> ORGANISM: Staphylococcus aureus

<400> SEQUENCE: 39

Gly Thr Asp Ile Thr Asn Gln Leu Thr Asn Val Thr Val Gly Ile Asp
1               5                   10                  15

Ser Gly Thr Thr Val Tyr Pro His Gln Ala Gly Tyr Val Lys Leu Asn
            20                  25                  30
```

```
Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
               100                 105                 110

Pro Glu Asn Val Lys Lys Thr Gly Asn Val Thr Leu Ala Thr Gly Ile
               115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                    165                 170                 175

Asp Asn Val Ile Ala Pro Val Leu Thr Gly Asn Leu Lys Pro Asn Thr
                180                 185                 190

Asp Ser Asn Ala Leu Ile Asp Gln Gln Asn Thr Ser Ile Lys Val Tyr
            195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
                260                 265                 270

Gly Asp Leu Ala Leu Arg Ser Thr Asn Ile Ile Trp Arg Ser Met Ser
            275                 280                 285

Trp Asp Asn Glu Val Ala Phe Asn Asn Gly Ser Gly Ser Gly Asp Gly
290                 295                 300

Ile Asp Lys Pro Val Val Pro Glu Gln Pro Asp Glu Pro Gly Glu Ile
305                 310                 315                 320

Glu Pro Ile Pro Glu
                325

<210> SEQ ID NO 40
<211> LENGTH: 325
<212> TYPE: PRT
<213> ORGANISM: Staphylococcus aureus

<400> SEQUENCE: 40

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
                 20                  25                  30

Tyr Gly Phe Ser Val Pro Asn Ser Ala Val Lys Gly Asp Thr Phe Lys
         35                  40                  45

Ile Thr Val Pro Lys Glu Leu Asn Leu Asn Gly Val Thr Ser Thr Ala
 50                  55                  60

Lys Val Pro Pro Ile Met Ala Gly Asp Gln Val Leu Ala Asn Gly Val
 65                  70                  75                  80
```

```
Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
            260                 265                 270

Gly Asp Leu Ala Leu Arg Ser Ser Asn Ile Ile Trp Arg Ser Met Ser
        275                 280                 285

Trp Asp Asn Glu Val Ala Phe Asn Asn Gly Ser Gly Ser Gly Asp Gly
    290                 295                 300

Ile Asp Lys Pro Val Val Pro Glu Gln Pro Asp Glu Pro Gly Glu Ile
305                 310                 315                 320

Glu Pro Ile Pro Glu
                325

<210> SEQ ID NO 41
<211> LENGTH: 325
<212> TYPE: PRT
<213> ORGANISM: Staphylococcus aureus

<400> SEQUENCE: 41

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
                20                  25                  30

Tyr Gly Phe Ser Val Pro Asn Ser Ala Val Lys Gly Asp Thr Phe Lys
            35                  40                  45

Ile Thr Val Pro Lys Glu Leu Asn Leu Asn Gly Val Thr Ser Thr Ala
        50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125
```

```
Gly Ser Thr Thr Ala Asn Lys Thr Val Leu Val Asp Tyr Glu Lys Tyr
            130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Asn Gly His Ile Asp Pro Asn Ser Lys
                260                 265                 270

Gly Asp Leu Ala Leu Arg Asn Ser Asn Ile Ile Trp Arg Ser Met Ser
            275                 280                 285

Trp Asp Asn Glu Val Ala Phe Asn Asn Gly Ser Gly Ser Asp Gly
            290                 295                 300

Ile Asp Lys Pro Val Val Pro Glu Gln Pro Asp Glu Pro Gly Glu Ile
305                 310                 315                 320

Glu Pro Ile Pro Glu
                325

<210> SEQ ID NO 42
<211> LENGTH: 324
<212> TYPE: PRT
<213> ORGANISM: Staphylococcus aureus

<400> SEQUENCE: 42

Gly Thr Asp Ile Thr Asn Gln Leu Thr Asn Val Thr Val Gly Ile Asp
  1               5                  10                  15

Ser Gly Thr Thr Val Tyr Pro His Gln Ala Gly Tyr Val Lys Leu Asn
             20                  25                  30

Tyr Gly Phe Ser Val Pro Asn Ser Ala Val Lys Gly Asp Thr Phe Lys
         35                  40                  45

Ile Thr Val Pro Lys Glu Leu Asn Leu Asn Gly Val Thr Ser Thr Ala
     50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
             85                  90                  95

Thr Lys Asp Asp Val Lys Ala Thr Leu Thr Met Pro Ala Tyr Ile Asp
                100                 105                 110

Pro Glu Asn Val Lys Lys Thr Gly Asn Val Thr Leu Ala Thr Gly Ile
            115                 120                 125

Gly Ser Thr Thr Ala Asn Lys Thr Val Leu Val Asp Tyr Glu Lys Tyr
            130                 135                 140

Gly Lys Phe Tyr Asn Leu Ser Ile Lys Gly Thr Ile Asp Gln Ile Asp
145                 150                 155                 160

Lys Thr Asn Asn Thr Tyr Arg Gln Thr Ile Tyr Val Asn Pro Ser Gly
                165                 170                 175
```

-continued

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
                245                 250                 255

Thr Pro Tyr Ile Val Val Val Asn Gly His Ile Asp Pro Asn Ser Lys
            260                 265                 270

Gly Asp Leu Ala Leu Arg Ser Thr Ile Ile Trp Arg Ser Met Ser Trp
        275                 280                 285

Asp Asn Glu Val Ala Phe Asn Asn Gly Ser Gly Ser Gly Asp Gly Ile
    290                 295                 300

Asp Lys Pro Val Val Pro Glu Gln Pro Asp Glu Pro Gly Glu Ile Glu
305                 310                 315                 320

Pro Ile Pro Glu

<210> SEQ ID NO 43
<211> LENGTH: 323
<212> TYPE: PRT
<213> ORGANISM: Staphylococcus aureus

<400> SEQUENCE: 43

Gly Thr Asp Ile Thr Asn Gln Leu Thr Asn Val Thr Val Gly Ile Asp
1               5                   10                  15

Ser Gly Thr Thr Val Tyr Pro His Gln Ala Gly Tyr Val Lys Leu Asn
            20                  25                  30

Tyr Gly Phe Ser Val Pro Asn Ser Ala Val Lys Gly Asp Thr Phe Lys
        35                  40                  45

Ile Thr Val Pro Lys Glu Leu Asn Leu Asn Gly Val Thr Ser Thr Ala
    50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
            85                  90                  95

Thr Lys Asp Asp Val Lys Ala Thr Leu Thr Met Pro Ala Tyr Ile Asp
        100                 105                 110

Pro Glu Asn Val Lys Lys Thr Gly Asn Val Thr Leu Ala Thr Gly Ile
    115                 120                 125

Gly Ser Thr Thr Ala Asn Lys Thr Val Leu Val Asp Tyr Glu Lys Tyr
130                 135                 140

Gly Lys Phe Tyr Asn Leu Ser Ile Lys Gly Thr Ile Asp Gln Ile Asp
            145                 150                 155                 160

Lys Thr Asn Asn Thr Tyr Arg Gln Thr Ile Tyr Val Asn Pro Ser Gly
            165                 170                 175

Asp Asn Val Ile Ala Pro Val Leu Thr Gly Asn Leu Lys Pro Asn Thr
        180                 185                 190

Asp Ser Asn Ala Leu Ile Asp Gln Gln Asn Thr Ser Ile Lys Val Tyr
    195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
            245                 250                 255

Thr Pro Tyr Ile Val Val Val Asn Gly His Ile Asp Pro Asn Ser Lys
        260                 265                 270

Gly Asp Leu Ala Leu Arg Ser Ile Ile Trp Arg Ser Met Ser Trp Asp
    275                 280                 285

Asn Glu Val Ala Phe Asn Asn Gly Ser Gly Ser Gly Asp Gly Ile Asp
            290                 295                 300

Lys Pro Val Val Pro Glu Gln Pro Asp Glu Pro Gly Glu Ile Glu Pro
305                 310                 315                 320

Ile Pro Glu

<210> SEQ ID NO 44
<211> LENGTH: 322
<212> TYPE: PRT
<213> ORGANISM: Staphylococcus aureus

<400> SEQUENCE: 44

Gly Thr Asp Ile Thr Asn Gln Leu Thr Asn Val Thr Val Gly Ile Asp
1               5                   10                  15

Ser Gly Thr Thr Val Tyr Pro His Gln Ala Gly Tyr Val Lys Leu Asn
                20                  25                  30

Tyr Gly Phe Ser Val Pro Asn Ser Ala Val Lys Gly Asp Thr Phe Lys
            35                  40                  45

Ile Thr Val Pro Lys Glu Leu Asn Leu Asn Gly Val Thr Ser Thr Ala
50                  55                  60

Lys Val Pro Pro Ile Met Ala Gly Asp Gln Val Leu Ala Asn Gly Val
65                  70                  75                  80

Ile Asp Ser Asp Gly Asn Val Ile Tyr Thr Phe Thr Asp Tyr Val Asn
                85                  90                  95

Thr Lys Asp Asp Val Lys Ala Thr Leu Thr Met Pro Ala Tyr Ile Asp
            100                 105                 110

Pro Glu Asn Val Lys Lys Thr Gly Asn Val Thr Leu Ala Thr Gly Ile
        115                 120                 125

Gly Ser Thr Thr Ala Asn Lys Thr Val Leu Val Asp Tyr Glu Lys Tyr
    130                 135                 140

Gly Lys Phe Tyr Asn Leu Ser Ile Lys Gly Thr Ile Gln Ile Asp
145                 150                 155                 160

Lys Thr Asn Asn Thr Tyr Arg Gln Thr Ile Tyr Val Asn Pro Ser Gly
                165                 170                 175

Asp Asn Val Ile Ala Pro Val Leu Thr Gly Asn Leu Lys Pro Asn Thr
            180                 185                 190

Asp Ser Asn Ala Leu Ile Asp Gln Gln Asn Thr Ser Ile Lys Val Tyr
        195                 200                 205

Lys Val Asp Asn Ala Ala Asp Leu Ser Glu Ser Tyr Phe Val Asn Pro
    210                 215                 220

Glu Asn Phe Glu Asp Val Thr Asn Ser Val Asn Ile Thr Phe Pro Asn
225                 230                 235                 240

Pro Asn Gln Tyr Lys Val Glu Phe Asn Thr Pro Asp Asp Gln Ile Thr
            245                 250                 255

Thr Pro Tyr Ile Val Val Val Asn Gly His Ile Asp Pro Asn Ser Lys
        260                 265                 270

-continued

```
Gly Asp Leu Ala Leu Arg Ser Ile Trp Arg Ser Met Ser Trp Asp Asn
            275                 280                 285

Glu Val Ala Phe Asn Asn Gly Ser Gly Ser Gly Asp Gly Ile Asp Lys
        290                 295                 300

Pro Val Val Pro Glu Gln Pro Asp Glu Pro Gly Glu Ile Glu Pro Ile
305                 310                 315                 320

Pro Glu

<210> SEQ ID NO 45
<211> LENGTH: 20
<212> TYPE: PRT
<213> ORGANISM: Staphylococcus aureus

<400> SEQUENCE: 45

Asp Leu Ala Leu Arg Ser Thr Leu Tyr Gly His Asn Ser Asn Ile Ile
1               5                   10                  15

Trp Arg Ser Met
            20
```